(12) United States Patent
Singh et al.

(10) Patent No.: US 11,427,541 B2
(45) Date of Patent: Aug. 30, 2022

(54) SALT FORMS OF A COMPLEMENT COMPONENT C5A RECEPTOR

(71) Applicant: CHEMOCENTRYX, INC., Mountain View, CA (US)

(72) Inventors: Rajinder Singh, Belmont, CA (US); Kwok Yau, Sunnyvale, CA (US); Yibin Zeng, Foster City, CA (US); Penglie Zhang, Foster City, CA (US); Rebecca M. Lui, Mountain View, CA (US); Ju Yang, Palo Alto, CA (US); Howard S. Roth, Sunnyvale, CA (US)

(73) Assignee: ChemoCentryx, Inc., San Carlos, CA (US)

( * ) Notice: Subject to any disclaimer, the term of this patent is extended or adjusted under 35 U.S.C. 154(b) by 86 days.

(21) Appl. No.: 17/091,044

(22) Filed: Nov. 6, 2020

(65) Prior Publication Data
US 2021/0139427 A1    May 13, 2021

Related U.S. Application Data

(60) Provisional application No. 62/932,658, filed on Nov. 8, 2019.

(51) Int. Cl.
| | | |
|---|---|---|
| C07D 211/60 | (2006.01) | |
| A61K 9/08 | (2006.01) | |
| A61K 9/00 | (2006.01) | |

(52) U.S. Cl.
CPC .......... *C07D 211/60* (2013.01); *A61K 9/0019* (2013.01); *A61K 9/08* (2013.01); *C07B 2200/13* (2013.01)

(58) Field of Classification Search
CPC ...... C07D 211/60; A61K 9/0019; A61K 9/08; C07B 2200/13
See application file for complete search history.

(56) References Cited

U.S. PATENT DOCUMENTS

| | | |
|---|---|---|
| 7,923,564 B2 | 4/2011 | Thygesen et al. |
| 8,445,515 B2 | 5/2013 | Fan et al. |
| 8,906,938 B2 | 12/2014 | Fan et al. |
| 9,126,939 B2 | 9/2015 | Fan et al. |
| 9,573,897 B2 | 2/2017 | Fan et al. |
| 10,035,768 B2 | 7/2018 | Fan et al. |
| 10,660,897 B2 | 5/2020 | Fan et al. |
| 11,026,935 B2 | 5/2021 | Singh et al. |
| 11,149,009 B2 * | 10/2021 | Li .................. C07D 405/12 |
| 2010/0311753 A1 | 12/2010 | Fan et al. |
| 2011/0275639 A1 | 11/2011 | Fan et al. |
| 2015/0141425 A1 | 5/2015 | Fan et al. |
| 2017/0065604 A1 | 3/2017 | Fan et al. |
| 2017/0114017 A1 | 4/2017 | Fan et al. |
| 2019/0062275 A1 | 2/2019 | Fan et al. |
| 2019/0134020 A1 | 5/2019 | Deng et al. |
| 2021/0139426 A1 | 5/2021 | Yau et al. |

FOREIGN PATENT DOCUMENTS

| | | |
|---|---|---|
| WO | 2010/075257 A1 | 1/2010 |
| WO | 2016/053890 A1 | 4/2016 |
| WO | 2019/236820 A1 | 12/2019 |

OTHER PUBLICATIONS

International Search Report and Written Opinion dated Feb. 3, 2021 corresponding to PCT/US2020/059280 filed Nov. 6, 2020; 9 pages.
International Search Report and Written Opinion dated Feb. 8, 2021 corresponding to PCT/US2020/059287 filed Nov. 6, 2020; 9 pages.
International Search Report and Written Opinion dated Mar. 18, 2021 corresponding to PCT/US2020/059291 filed Nov. 6, 2020; 14 pages.
Anonymously Disclosed IP.com Prior Art Database Technical Disclosure [IP.com No. IPCOM000255250D with an IP.com Electronic Publication Date of Sep. 12, 2018] submitted in a Third Party Observed filed Jul. 27, 2021 corresponding to PCT/US2020/059287 with additional comments; 6 pages.
Pubchem, SID 237279170, Available Date: Feb. 13, 2015 [retrieved on Jan. 5, 2021]; Retrived form the Internet <URL: https://pubchem.ncbi.nlm.nih.gov/substance /237279170>; 8 pages.
U.S. Appl. No. 17/091,001, filed Nov. 6, 2020, Yau et al.
U.S. Appl. No. 17/091,019, filed Nov. 6, 2020, Singh et al.

\* cited by examiner

*Primary Examiner* — Timothy R Rozof
(74) *Attorney, Agent, or Firm* — Mintz Levin Cohn Ferris Glovsky and Popeo PC

(57) ABSTRACT

Provided herein are salt forms of a complement component 5a receptor having the formula of Compound 1

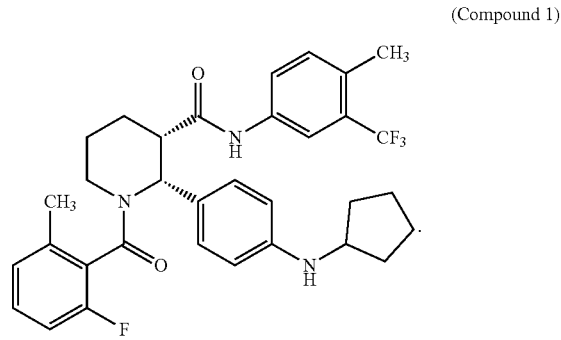

(Compound 1)

Also provided herein are pharmaceutical compositions and methods of treatment using the salt forms of Compound 1, described herein.

32 Claims, 26 Drawing Sheets

SALT FORMS OF A COMPLEMENT COMPONENT C5A RECEPTOR

CROSS-REFERENCES TO RELATED APPLICATIONS

This application claims the benefit of priority under 35 U.S.C § 119(e) to U.S. Provisional Application Ser. No. 62/932,658 filed Nov. 8, 2019, the disclosure of which is incorporated herein by reference in its entirety.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The complement system plays a central role in the clearance of immune complexes and in immune responses to infectious agents, foreign antigens, virus infected cells and tumor cells. Inappropriate or excessive activation of the complement system can lead to harmful, and even potentially life-threatening consequences due to severe inflammation and resulting tissue destruction. These consequences are clinically manifested in various disorders including septic shock; myocardial, as well as, intestinal ischemia/reperfusion injury; graft rejection; organ failure; nephritis; pathological inflammation; and autoimmune diseases.

The complement system is composed of a group of proteins that are normally present in the serum in an inactive state. Activation of the complement system encompasses mainly three distinct pathways, i.e., the classical, the alternative, and the lectin pathway (V. M. Holers, In *Clinical Immunology: Principles and Practice*, ed. R. R. Rich, Mosby Press; 1996, 363-391): 1) The classical pathway is a calcium/magnesium-dependent cascade, which is normally activated by the formation of antigen-antibody complexes. It can also be activated in an antibody-independent manner by the binding of C-reactive protein, complexed with ligand, and by many pathogens including gram-negative bacteria. 2) The alternative pathway is a magnesium-dependent cascade which is activated by deposition and activation of C3 on certain susceptible surfaces (e.g. cell wall polysaccharides of yeast and bacteria, and certain biopolymer materials). 3) The lectin pathway involves the initial binding of mannose-binding lectin and the subsequent activation of C2 and C4, which are common to the classical pathway (Matsushita, M. et al., *J. Exp. Med.* 176: 1497-1502 (1992); Suankratay, C. et al., *J. Immunol.* 160: 3006-3013 (1998)).

The activation of the complement pathway generates biologically active fragments of complement proteins, e.g. C3a, C4a and C5a anaphylatoxins and C5b-9 membrane attack complexes (MAC), all which mediate inflammatory responses by affecting leukocyte chemotaxis; activating macrophages, neutrophils, platelets, mast cells and endothelial cells; and increasing vascular permeability, cytolysis and tissue injury.

Complement C5a is one of the most potent proinflammatory mediators of the complement system. (The anaphylactic C5a peptide is 100 times more potent, on a molar basis, in eliciting inflammatory responses than C3a.) C5a is the activated form of C5 (190 kD, molecular weight). C5a is present in human serum at approximately 80 µg/ml (Kohler, P. F. et al., *J. Immunol.* 99: 1211-1216 (1967)). It is composed of two polypeptide chains, α and β, with approximate molecular weights of 115 kD and 75 kD, respectively (Tack, B. F. et al., *Biochemistry* 18: 1490-1497 (1979)). Biosynthesized as a single-chain promolecule, C5 is enzymatically cleaved into a two-chain structure during processing and secretion. After cleavage, the two chains are held together by at least one disulphide bond as well as noncovalent interactions (Ooi, Y. M. et al., *J. Immunol.* 124: 2494-2498 (1980)).

Recent work has identified (2R,3S)-2-(4-(cyclopentylamino)phenyl)-1-(2-fluoro-6-methylbenzoyl)-N-(4-methyl-3-(trifluoromethyl)phenyl)piperidine-3-carboxamide, Compound 1

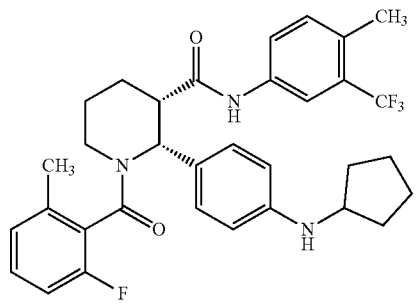 [SMILES: Cc1ccc(NC(=O)[C@H]2CCCN(C(=O)c3c(C)cccc3F)[C@H]2c2ccc(NC3CCCC3)cc2)cc1C(F)(F)F]

as useful for treating C5a mediated diseases. Despite the disclosure of this compound, the efficient delivery of biologically relevant amounts of Compound 1 remains challenging. Moreover, no salt forms of this compound have been reported.

Salt forms may improve important biological characteristics such as solubility, dissolution rate, and bioavailability, thereby improving the therapeutic efficacy of this compound. As such, there exists a need to provide salt forms of Compound 1 that may offer advantageous pharmacokinetic properties. The present disclosure addresses these needs and provides related advantages as well.

BRIEF SUMMARY OF THE INVENTION

The present disclosure provides salt forms of Compound 1, (2R,3S)-2-(4-(cyclopentylamino)phenyl)-1-(2-fluoro-6-methylbenzoyl)-N-(4-methyl-3-(trifluoromethyl)phenyl)piperidine-3-carboxamide,

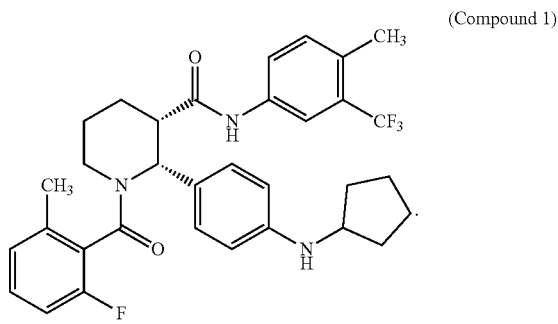 [SMILES: Cc1ccc(NC(=O)[C@H]2CCCN(C(=O)c3c(C)cccc3F)[C@H]2c2ccc(NC3CCCC3)cc2)cc1C(F)(F)F]

(Compound 1)

In some aspects, provided herein is a besylate salt of Compound 1. In some embodiments, the besylate salt of Compound 1 is a single crystalline form which is substantially free of other crystalline or amorphous forms. In some embodiments, the single crystalline form is besylate salt Form I of Compound 1. In some embodiments, the single crystalline form is besylate salt Form II of Compound 1.

In some aspects, provided herein is a tosylate salt of Compound 1. In some embodiments, the tosylate salt of Compound 1 is a single crystalline form which is substantially free of other crystalline or amorphous forms. In some embodiments, the single crystalline form is tosylate salt Form I of Compound 1.

In some aspects, provided herein is a napadisylate salt of Compound 1. In some embodiments, the napadisylate salt of Compound 1 is a single crystalline form which is substantially free of other crystalline or amorphous forms. In some embodiments, the single crystalline form is napadisylate salt Form I of Compound 1.

In some aspects, provided herein is a napsylate salt of Compound 1. In some embodiments, the napsylate salt of Compound 1 is a single crystalline form which is substantially free of other crystalline or amorphous forms. In some embodiments, the single crystalline form is napsylate salt Form I of Compound 1.

In some aspects, provided herein is a camsylate salt of Compound 1. In some embodiments, the camsylate salt of Compound 1 is a single crystalline form which is substantially free of other crystalline or amorphous forms. In some embodiments, the single crystalline form is camsylate salt Form I of Compound 1.

In some aspects, provided herein is a edisylate salt of Compound 1. In some embodiments, the edisylate salt of Compound 1 is a single crystalline form which is substantially free of other crystalline or amorphous forms. In some embodiments, the single crystalline form is edisylate salt Form I of Compound 1.

Each of the provided salt forms can be further characterized as described herein.

In further aspects, provided herein are pharmaceutical compositions of the salt forms of Compound 1 described herein.

In additional aspects, provided herein are methods of treating an individual suffering from or susceptible to a disease or disorder involving pathologic activation of C5a receptors, comprising administering to the individual an effective amount of a salt form of Compound 1 described herein.

DETAILED DESCRIPTION OF THE INVENTION

I. General

Figure 1:
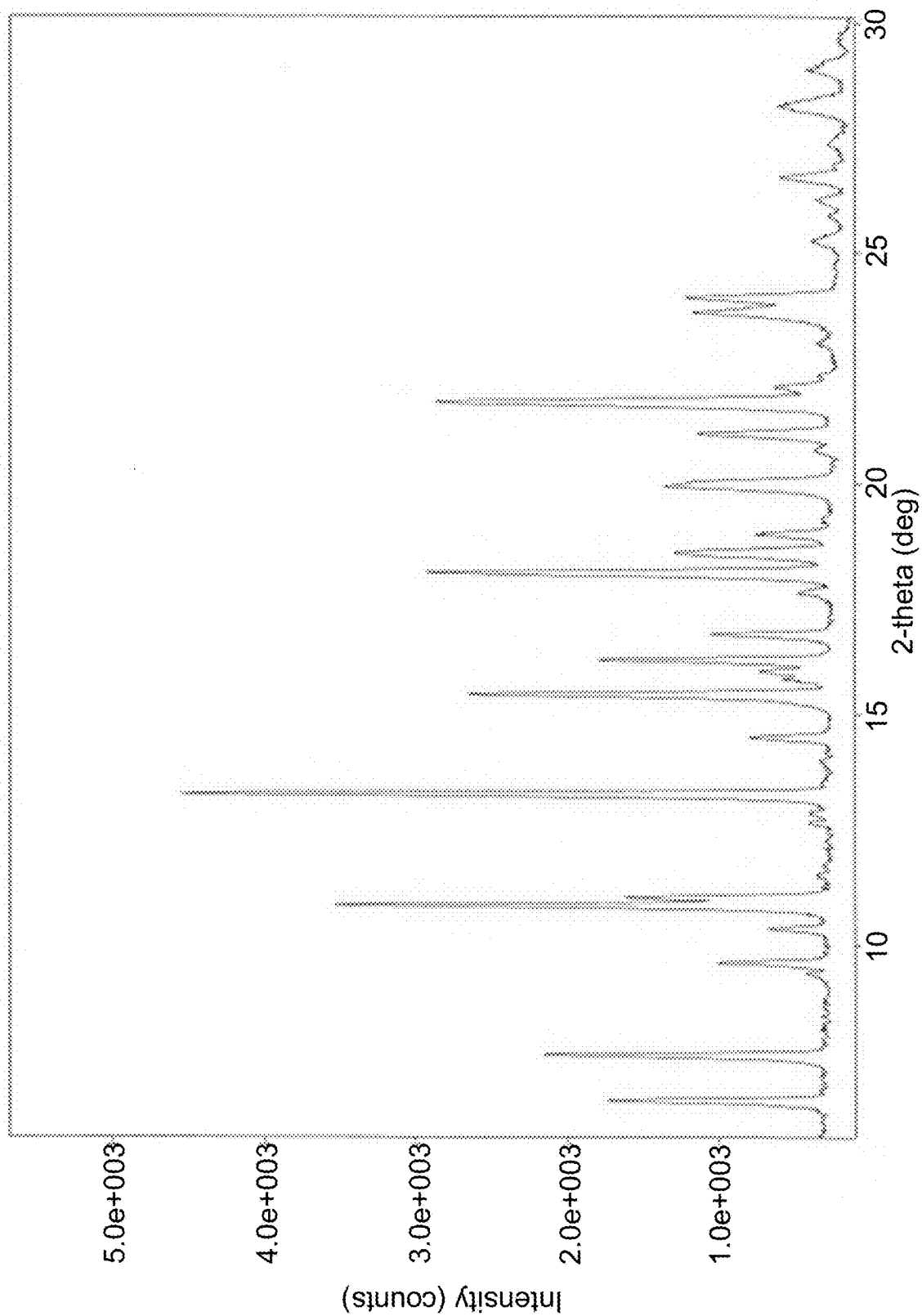
FIG. 1 shows X-ray powder diffraction (XRPD) patterns of besylate salt Form I of Compound 1.

The present disclosure provides salt forms of Compound 1. These forms advantageously increases solubility and bioavailability of the compound, providing an opportunity to prepare, for example, pharmaceutical formulations that can deliver biologically relevant amounts of Compound 1 without the need for administering excessive volumes of liquid or an excessive number of capsules.

II. Definitions

The terms "about" and "around," as used herein to modify a numerical value, indicate a close range around that explicit value. If "X" were the value, "about X" or "around X" would indicate a value from 0.9X to 1.1X, and more preferably, a value from 0.95X to 1.05X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X."

"Compound 1" is a chemical compound having an IUPAC name of (2R,3 S)-2-(4-(cyclopentylamino)phenyl)-1-(2-fluoro-6-methylbenzoyl)-N-(4-methyl-3-(trifluoromethyl) phenyl)piperidine-3-carboxamide, and the structure shown below:

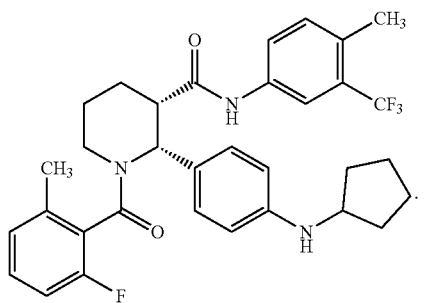

(Compound 1)

"Substantially free" refers to an amount of 10% or less of another form, preferably 8%, 5%, 4%, 3%, 2%, 1%, 0.5%, or less of another form.

The neutral form of Compound 1 may be regenerated by contacting the salt with a base or acid and isolating the parent compound in the conventional manner. The parent form of Compound 1 differs from the various salt forms in certain physical properties, such as (but not limited to) solubility in polar solvents, but otherwise the salts are equivalent to the parent form of Compound 1 for the purposes of the present disclosure.

The term "treating" or "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms).

As used herein, a condition is considered "responsive to C5a receptor modulation" if modulation of C5a receptor activity results in the reduction of inappropriate activity of a C5a receptor.

The term "individual" refers to mammals, which includes primates (especially humans), domesticated companion animals (such as dogs, cats, horses, and the like) and livestock (such as cattle, pigs, sheep, and the like), with dosages as described herein. In some embodiments, the term "individual" refers to a human.

III. Detailed Description of Embodiments

Provided herein are salt forms of Compound 1, pharmaceutical compositions comprising the same, methods of their use, and methods of preparing the salt forms.

A. Salt Forms of Compound 1

The present disclosure provides various salt forms of Compound 1 including a besylate salt, a tosylate salt, a napadisylate salt, a napsylate salt, a camsylate salt, and an edisylate salt. In certain embodiments, a single crystalline form of a besylate salt, a tosylate salt, a napadisylate salt, a napsylate salt, a camsylate salt, or an edisylate salt is provided. The single crystalline forms of the described salts are, in certain embodiments, substantially free of other crystalline or amorphous forms.

In some embodiments the besylate salt of Compound 1 has the formula:

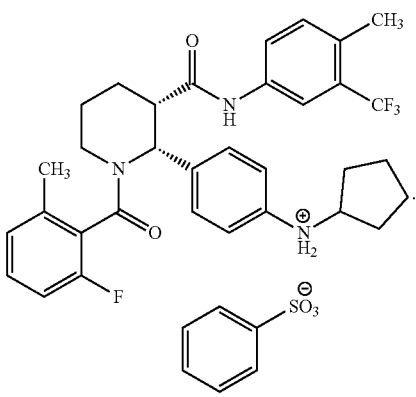

In some embodiments the tosylate salt of Compound 1 has the formula:

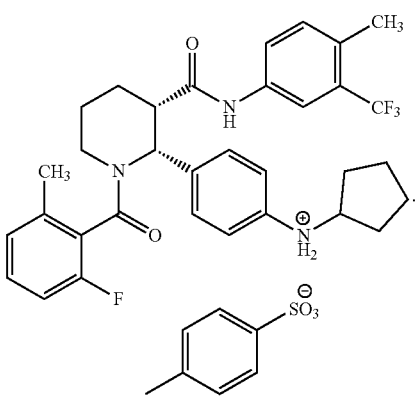

In some embodiments the napadisylate salt of Compound 1 has the formula:

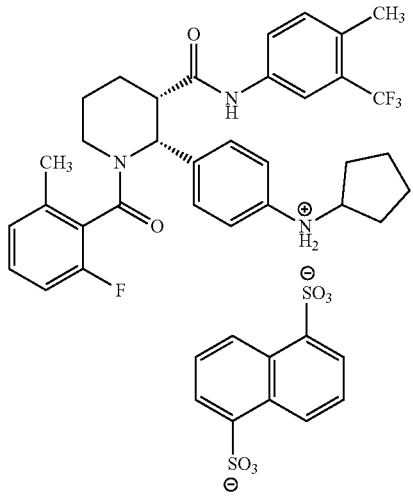

In some embodiments the napsylate salt of Compound 1 has the formula:

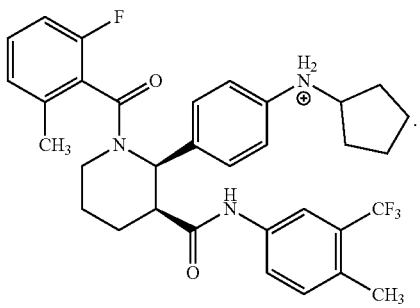

In some embodiments the camsylate salt of Compound 1 has the formula:

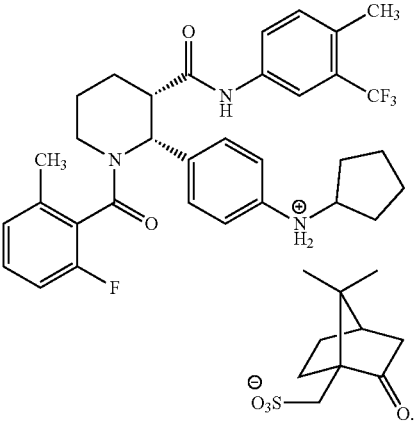

In some embodiments the edisylate salt of Compound 1 has the formula:

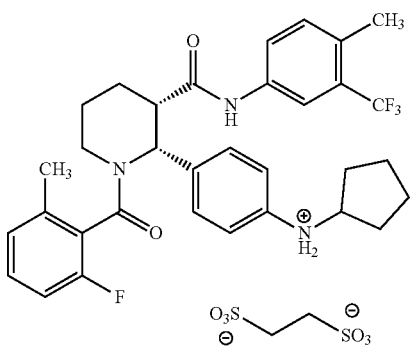

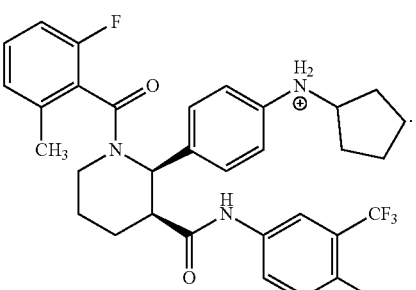

Particular salts disclosed herein can exist in one or more polymorphic forms. Individual polymorphic forms of the described salts are identified as Form I, Form II, etc.

i. A Besylate Salt of Compound 1 (Form I)

In some aspects, provided herein is besylate salt Form I of Compound 1

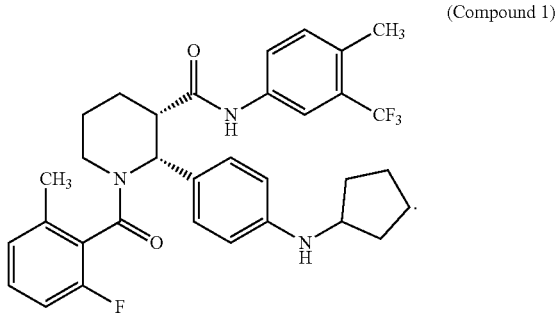 [SMILES: Cc1ccc(NC(=O)[C@H]2CCCN(C(=O)c3c(C)cccc3F)[C@H]2c2ccc(NC3CCCC3)cc2)cc1C(F)(F)F]

(Compound 1)

which is substantially free of other crystalline or amorphous forms of Compound 1.

In some embodiments, Form I of the besylate salt of Compound 1 is characterized by an X-ray powder diffraction pattern comprising peaks at 10.9, 13.3, 16.2, 17.6 and 21.8 degrees 2θ (±0.2 degrees 2θ). In some embodiments, Form I of the besylate salt of Compound 1 is further characterized by an X-ray powder diffraction pattern comprising peaks at 6.6, 7.6, 14.5, 16.2, and 28.2 degrees 2θ (±0.2 degrees 2θ). In some embodiments, Form I of the besylate salt of Compound 1 is characterized by an X-ray powder diffraction pattern substantially in accordance with FIG. 1.

Differential scanning calorimetry (DSC) can also be used to characterize Form I of the besylate salt of Compound 1 described herein. In some embodiments, Form I of the besylate salt of Compound 1 is characterized by a differential scanning calorimetry thermogram (DSC) comprising an endothermic peak at around 207.2° C. In some embodiments, Form I of the besylate salt of Compound 1 is characterized by a melting point onset of about 200.6° C. as determined by differential scanning calorimetry thermogram (DSC). In some embodiments, Form I of the besylate salt of Compound 1 is characterized by a differential scanning calorimetry (DSC) thermogram substantially in accordance with FIG. 2.

Thermal gravimetric analysis (TGA) is another technique that can be used to characterize Form I of the besylate salt of Compound 1 described herein. In some embodiments, Form I of the besylate salt of Compound 1 is characterized by a weight loss of about 0.14% upon heating to around 202.9° C., as measured by thermal gravimetric analysis (TGA). In some embodiments, Form I of the besylate salt of Compound 1 is characterized by a thermal gravimetric analysis (TGA) thermogram substantially in accordance with FIG. 2.

Dynamic vapor sorption (DVS) is an additional method that can be used to characterize Form I of the besylate salt of Compound 1 described herein. In some embodiments, Form I of the besylate salt of Compound 1 is characterized by a weight gain of about 0.5% after undergoing a dynamic vapor sorption cycle (DVS) from about 0% relative humidity (RH) to about 75% RH at 25° C. In some embodiments, Form I of the besylate salt of Compound 1 is characterized by a weight gain of about 0.73% after undergoing a dynamic vapor sorption (DVS) cycle from about 5% relative humidity (RH) to about 95% RH at 25° C. In some embodiments, Form I of the besylate salt of Compound 1 is characterized by a dynamic vapor sorption (DVS) plot substantially in accordance with FIG. 3.

Microscopy can also be used to characterize Form I of the besylate salt of Compound 1 described herein. In some embodiments, scanning electron microscopy (SEM) is used. In some embodiments, Form I of the besylate salt of Compound 1 is characterized by an SEM image having predominantly prismatic or anhedral particles. In some embodiments, the particles are about 1 μm to 73 μm, as determined by SEM. In some embodiments, Form I of the besylate salt of Compound 1 is characterized by scanning electron microscopy (SEM) images substantially in accordance with FIG. 4.

Figure 5:
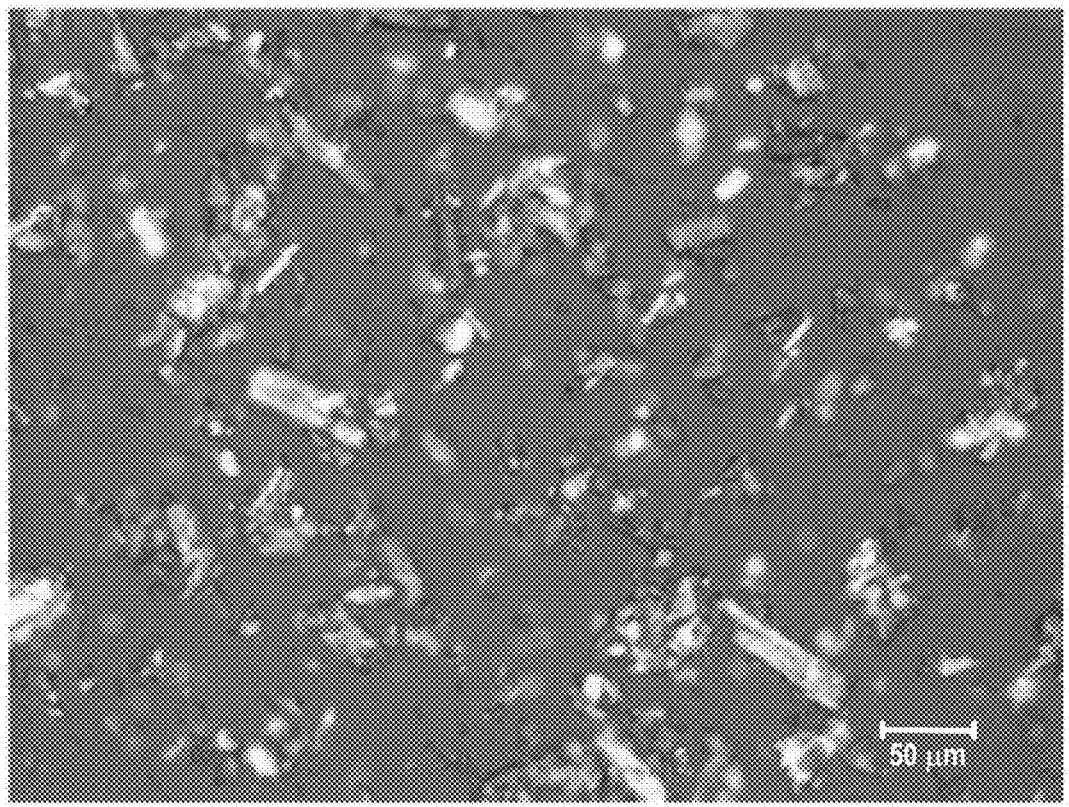
FIG. 5 shows a representative polarized light microscopy (PLM) image of besylate salt Form I of Compound 1. The magnification shown is 20×.

Polarized light microscopy (PLM) is another technique that can be used to characterize Form I of the besylate salt of Compound 1 described herein. In some embodiments, Form I of the besylate salt of Compound 1 is characterized by particles ranging in size from about 2.5 to 83 μm as determined by polarized light microscope (PLM). In some embodiments, Form I of the besylate salt of Compound 1 is characterized by polarized light microscope (PLM) profile substantially as shown in FIG. 5.

ii. A Besylate Salt of Compound 1 (Form II)

In some aspects, provided herein is besylate salt Form II of Compound 1

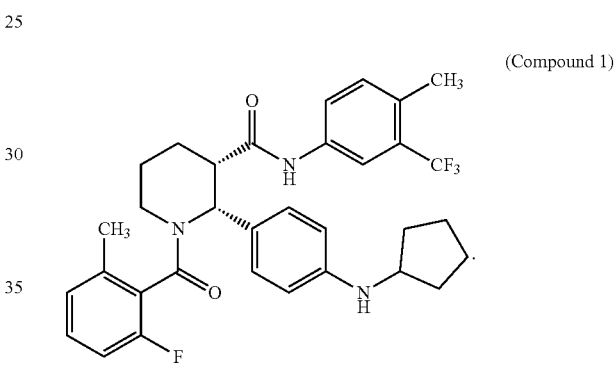

(Compound 1)

which is substantially free of other crystalline or amorphous forms of Compound 1.

In some embodiments, Form II of the besylate salt of Compound 1 is characterized by an X-ray powder diffraction pattern comprising peaks at 3.6, 7.1, 12.3, 12.8, and 16.7 degrees 2θ (±0.2 degrees 2θ). In some embodiments, Form II of the besylate salt of Compound 1 is characterized by an X-ray powder diffraction pattern substantially in accordance with FIG. 6.

Differential scanning calorimetry (DSC) can also be used to characterize Form II of the besylate salt of Compound 1 described herein. In some embodiments, Form II of the besylate salt of Compound 1 is characterized by a differential scanning calorimetry thermogram (DSC) comprising an endothermic peak at around 187.2° C. In some embodiments, Form II of the besylate salt of Compound 1 is characterized by a melting point onset of about 180.5° C. as determined by differential scanning calorimetry thermogram (DSC). In some embodiments, Form II of the besylate salt of Compound 1 is characterized by a differential scanning calorimetry (DSC) thermogram substantially in accordance with FIG. 7.

Thermal gravimetric analysis (TGA) is another technique that can be used to characterize Form II of the besylate salt of Compound 1 described herein. In some embodiments, Form II of the besylate salt of Compound 1 is characterized by a weight loss of about 0.095% upon heating to around 189.5° C., as measured by thermal gravimetric analysis (TGA). In some embodiments, Form II of the besylate salt of Compound 1 is characterized by a thermal gravimetric analysis (TGA) thermogram substantially in accordance with FIG. 7.

iii. A Tosylate Salt of Compound 1 (Form I)

In some aspects, provided herein is tosylate salt Form I of Compound 1

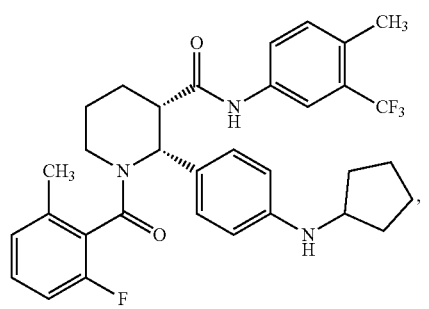

(Compound 1)

which is substantially free of other crystalline or amorphous forms of Compound 1.

In some embodiments, tosylate salt Form I of Compound 1 is characterized by an X-ray powder diffraction pattern comprising peaks at 7.6, 10.8, 13.1, 16.5, 19.7, 21.6 degrees 2θ (±0.2 degrees 2θ). In some embodiments, tosylate salt Form I of Compound 1 is further characterized by an X-ray powder diffraction pattern comprising peaks at 6.6, 15.3, 16.0, and 27.8 degrees 2θ (±0.2 degrees 2θ). In some embodiments, tosylate salt Form I of Compound 1 is characterized by an X-ray powder diffraction pattern substantially in accordance with FIG. 8.

Differential scanning calorimetry (DSC) can also be used to characterize tosylate salt Form I of Compound 1 described herein. In some embodiments, tosylate salt Form I of Compound 1 is characterized by a differential scanning calorimetry thermogram (DSC) comprising an endothermic peak at around 209.8° C. In some embodiments, tosylate salt Form I of Compound 1 is characterized by a melting point onset of about 206.1° C. as determined by differential scanning calorimetry thermogram (DSC). In some embodiments, tosylate salt Form I of Compound 1 is characterized by a differential scanning calorimetry (DSC) thermogram substantially in accordance with FIG. 9.

Thermal gravimetric analysis (TGA) is another technique that can be used to characterize Form I of the tosylate salt of Compound 1 described herein. In some embodiments, Form I of the tosylate salt of Compound 1 is characterized by a weight loss of about 0.19% upon heating to around 204.2° C., as measured by thermal gravimetric analysis (TGA). In some embodiments, Form I of the tosylate salt of Compound 1 is characterized by a thermal gravimetric analysis (TGA) thermogram substantially in accordance with FIG. 9.

Dynamic vapor sorption (DVS) is an additional method that can be used to characterize tosylate salt Form I of Compound 1 described herein. In some embodiments, tosylate salt Form I of Compound 1 is characterized by a weight gain of about 0.58% after undergoing a dynamic vapor sorption cycle (DVS) from about 0% relative humidity (RH) to about 75% RH at 25° C. In some embodiments, tosylate salt Form I of Compound 1 is characterized by a weight gain of about 0.83% after undergoing a dynamic vapor sorption (DVS) cycle from about 5% relative humidity (RH) to about 95% RH at 25° C. In some embodiments, tosylate salt Form I of Compound 1 is characterized by a dynamic vapor sorption (DVS) plot substantially in accordance with FIG. 10.

Microscopy can also be used to characterize tosylate salt Form I of Compound 1 described herein. In some embodiments, scanning electron microscopy (SEM) is used. In some embodiments, tosylate salt Form I of Compound 1 is characterized by an SEM image having predominantly blade, rod, or equant particles. In some embodiments, the particles are about 1 μm to 500 μm, as determined by SEM. In some embodiments, tosylate salt Form I of Compound 1 is characterized by scanning electron microscopy (SEM) images substantially in accordance with FIG. 11.

Figure 12:
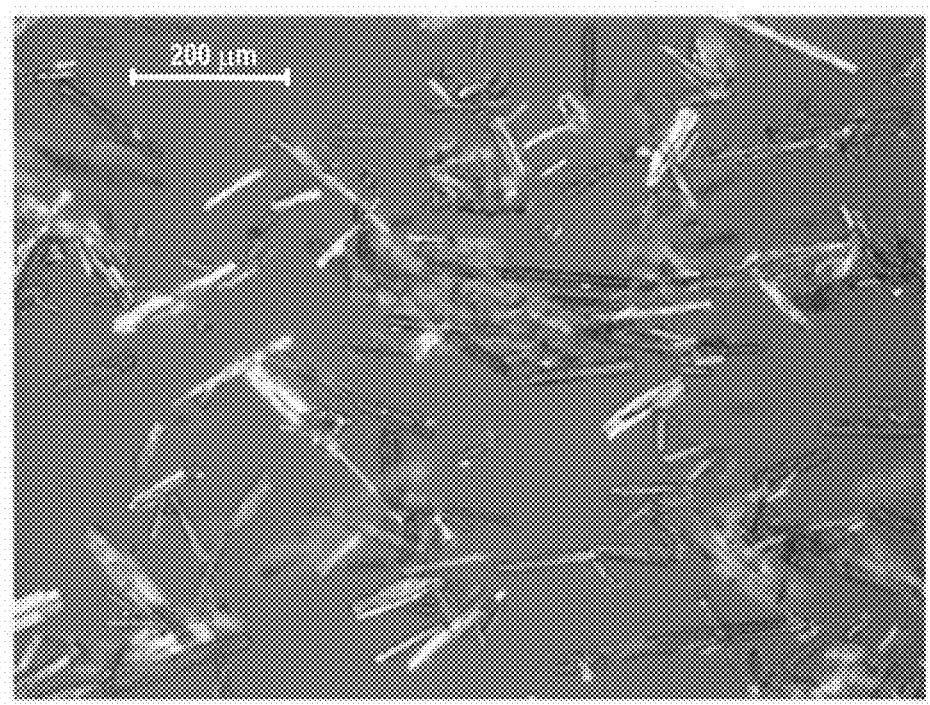
FIG. 12 shows a representative polarized light microscopy (PLM) image of tosylate salt Form I of Compound 1. The magnification shown is 10×.

Polarized light microscopy (PLM) is another technique that can be used to characterize tosylate salt Form I of Compound 1 described herein. In some embodiments, tosylate salt Form I of Compound 1 is characterized by particles ranging in size from about 2.5 to 440 μm as determined by polarized light microscope (PLM). In some embodiments, tosylate salt Form I of Compound 1 is characterized by polarized light microscope (PLM) profile substantially as shown in FIG. 12.

iv. A Napadisylate Salt of Compound 1 (Form I)

In some aspects, provided herein is napadisylate salt Form I of Compound 1

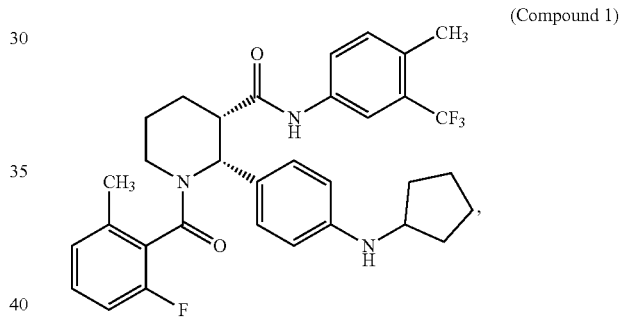

(Compound 1)

which is substantially free of other crystalline or amorphous forms of Compound 1.

In some embodiments, napadisylate salt Form I of Compound 1 is characterized by an X-ray powder diffraction pattern comprising peaks at 6.5, 7.0, 12.4, 14.7, 15.2, and 18.0 degrees 2θ (±0.2 degrees 2θ). In some embodiments, napadisylate salt Form I of Compound 1 is further characterized by an X-ray powder diffraction pattern comprising peaks at 9.6, 11.2, 18.6, and 20.4 degrees 2θ (±0.2 degrees 2θ). In some embodiments, napadisylate salt Form I of Compound 1 is characterized by an X-ray powder diffraction pattern substantially in accordance with FIG. 13.

Differential scanning calorimetry (DSC) can also be used to characterize napadisylate salt Form I of Compound 1 described herein. In some embodiments, napadisylate salt Form I of Compound 1 is characterized by a differential scanning calorimetry thermogram (DSC) comprising an endothermic peak at around 232.8° C. In some embodiments, napadisylate salt Form I of Compound 1 is characterized by a melting point onset of about 222.7° C. as determined by differential scanning calorimetry thermogram (DSC). In some embodiments, napadisylate salt Form I of Compound 1 is characterized by a differential scanning calorimetry (DSC) thermogram substantially in accordance with FIG. 14.

Thermal gravimetric analysis (TGA) is another technique that can be used to characterize Form I of the napadisylate salt of Compound 1 described herein. In some embodiments, Form I of the napadisylate salt of Compound 1 is characterized by a weight loss of about 2.0% upon heating to around 233.1° C., as measured by thermal gravimetric analysis (TGA). In some embodiments, Form I of the napadisylate salt of Compound 1 is characterized by a thermal gravimetric analysis (TGA) thermogram substantially in accordance with FIG. 14.

Dynamic vapor sorption (DVS) is an additional method that can be used to characterize napadisylate salt Form I of Compound 1 described herein. In some embodiments, napadisylate salt Form I of Compound 1 is characterized by a weight gain of about 0.6% after undergoing a dynamic vapor sorption cycle (DVS) from about 0% relative humidity (RH) to about 55% RH at 25° C. In some embodiments, napadisylate salt Form I of Compound 1 is characterized by a weight gain of about 1.42% after undergoing a dynamic vapor sorption (DVS) cycle from about 5% relative humidity (RH) to about 95% RH at 25° C. In some embodiments, napadisylate salt Form I of Compound 1 is characterized by a dynamic vapor sorption (DVS) plot substantially in accordance with FIG. 15.

Microscopy can also be used to characterize napadisylate salt Form I of Compound 1 described herein. In some embodiments, scanning electron microscopy (SEM) is used. In some embodiments, napadisylate salt Form I of Compound 1 is characterized by an SEM image having predominantly blade, rod or equant particles. In some embodiments, the particles are about 1 µm to 150 µm, as determined by SEM. In some embodiments, napadisylate salt Form I of Compound 1 is characterized by scanning electron microscopy (SEM) images substantially in accordance with FIG. 16.

Figure 17:
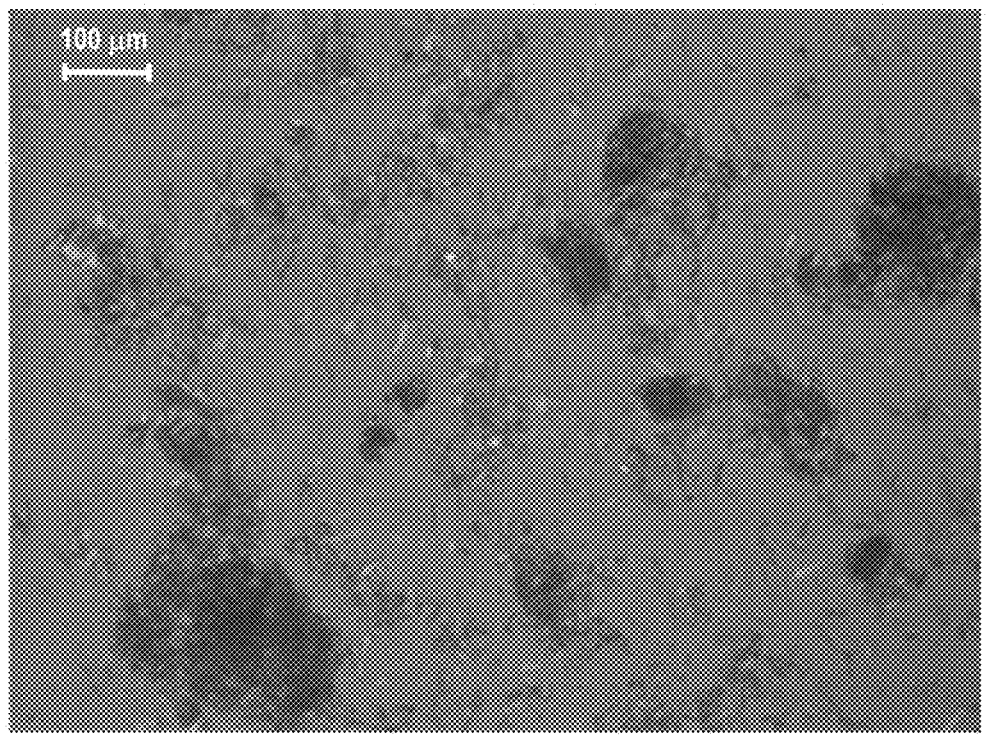
FIG. 17 shows a representative polarized light microscopy (PLM) image of napadisylate salt Form I of Compound 1. The magnification shown is 20×.

Polarized light microscopy (PLM) is another technique that can be used to characterize napadisylate salt Form I of Compound 1 described herein. In some embodiments, napadisylate salt Form I of Compound 1 is characterized by particles ranging in size from about 1.3 to 75 µm as determined by polarized light microscope (PLM). In some embodiments, napadisylate salt Form I of Compound 1 is characterized by polarized light microscope (PLM) profile substantially as shown in FIG. 17.

v. A Napsylate Salt of Compound 1 (Form I)

In some aspects, provided herein is napsylate salt Form I of Compound 1

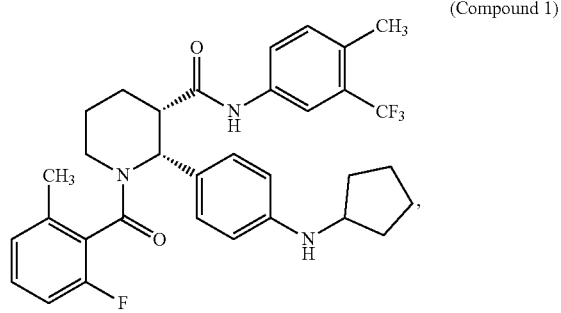 [SMILES: Cc1ccc(NC(=O)[C@H]2CCCN(C(=O)c3c(C)cccc3F)[C@H]2c2ccc(NC3CCCC3)cc2)cc1C(F)(F)F]

(Compound 1)

which is substantially free of other crystalline or amorphous forms of Compound 1.

In some embodiments, napsylate salt Form I of Compound 1 is characterized by an X-ray powder diffraction pattern comprising peaks at 6.5, 7.7, 10.4, 12.9, and 16.1 degrees 2θ (±0.2 degrees 2θ). In some embodiments, napsylate salt Form I of Compound 1 is further characterized by an X-ray powder diffraction pattern comprising peaks at 15.4, 15.5, 17.8, and 20.8 degrees 2θ (±0.2 degrees 2θ). In some embodiments, napsylate salt Form I of Compound 1 is characterized by an X-ray powder diffraction pattern substantially in accordance with FIG. 18.

Differential scanning calorimetry (DSC) can also be used to characterize napsylate salt Form I of Compound 1 described herein. In some embodiments, napsylate salt Form I of Compound 1 is characterized by a differential scanning calorimetry thermogram (DSC) comprising an endothermic peak at around 218.3° C. In some embodiments, napsylate salt Form I of Compound 1 is characterized by a melting point onset of about 211.7° C. as determined by differential scanning calorimetry thermogram (DSC). In some embodiments, napsylate salt Form I of Compound 1 is characterized by a differential scanning calorimetry (DSC) thermogram substantially in accordance with FIG. 19.

Thermal gravimetric analysis (TGA) is another technique that can be used to characterize Form I of the napsylate salt of Compound 1 described herein. In some embodiments, Form I of the napsylate salt of Compound 1 is characterized by a weight loss of about 0.49% upon heating to around 217° C., as measured by thermal gravimetric analysis (TGA). In some embodiments, Form I of the napsylate salt of Compound 1 is characterized by a thermal gravimetric analysis (TGA) thermogram substantially in accordance with FIG. 19.

Dynamic vapor sorption (DVS) is an additional method that can be used to characterize napsylate salt Form I of Compound 1 described herein. In some embodiments, napsylate salt Form I of Compound 1 is characterized by a weight gain of about 0.2% after undergoing a dynamic vapor sorption cycle (DVS) from about 0% relative humidity (RH) to about 55% RH at 25° C. In some embodiments, napsylate salt Form I of Compound 1 is characterized by a weight gain of about 0.65% after undergoing a dynamic vapor sorption (DVS) cycle from about 5% relative humidity (RH) to about 95% RH at 25° C. In some embodiments, napsylate salt Form I of Compound 1 is characterized by a dynamic vapor sorption (DVS) plot substantially in accordance with FIG. 20.

Microscopy can also be used to characterize napsylate salt Form I of Compound 1 described herein. In some embodiments, scanning electron microscopy (SEM) is used. In some embodiments, napsylate salt Form I of Compound 1 is characterized by an SEM image having predominantly blade, rod, and equant particles. In some embodiments, the particles are about 1 µm to 150 µm, as determined by SEM. In some embodiments, napsylate salt Form I of Compound 1 is characterized by scanning electron microscopy (SEM) images substantially in accordance with FIG. 21.

Figure 22:
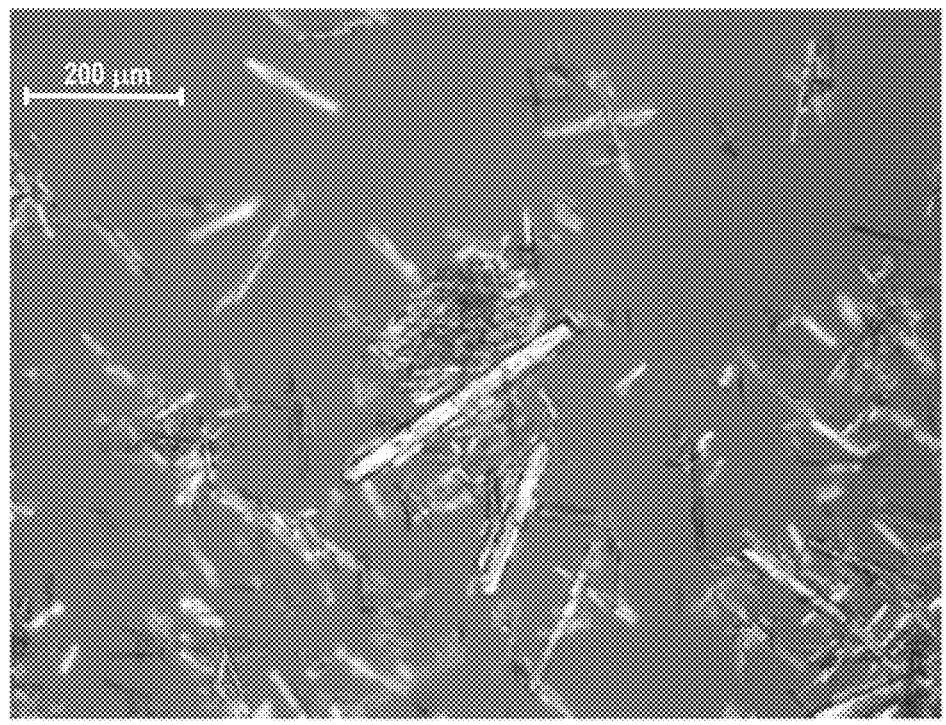
FIG. 22 shows a representative polarized light microscopy (PLM) image of napsylate salt Form I of Compound 1. The magnification shown is 10×.

Polarized light microscopy (PLM) is another technique that can be used to characterize napsylate salt Form I of Compound 1 described herein. In some embodiments, napsylate salt Form I of Compound 1 is characterized by particles ranging in size from about 5 to 470 µm as determined by polarized light microscope (PLM). In some embodiments, napsylate salt Form I of Compound 1 is characterized by polarized light microscope (PLM) profile substantially as shown in FIG. 22.

vi. A Camsylate Salt of Compound 1 (Form I)

In some aspects, provided herein is a camsylate salt Form I of Compound 1

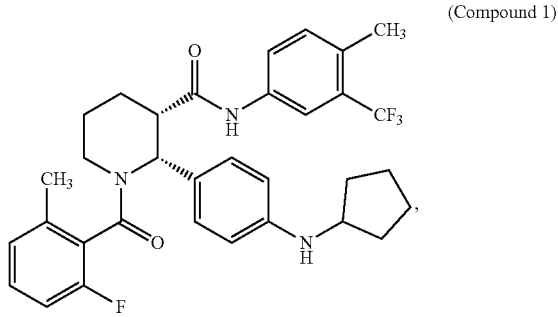 [SMILES: Cc1ccc(NC(=O)[C@H]2CCCN(C(=O)c3c(C)cccc3F)[C@H]2c2ccc(NC3CCCC3)cc2)cc1C(F)(F)F]

(Compound 1)

which is substantially free of other crystalline or amorphous forms of Compound 1.

In some embodiments, camsylate salt Form I of Compound 1 is characterized by an X-ray powder diffraction pattern comprising peaks at 6.3, 7.9, 10.8, 12.2, and 16.1 degrees 2θ (±0.2 degrees 2θ). In some embodiments, camsylate salt Form I of Compound 1 is further characterized by an X-ray powder diffraction pattern comprising peaks at 7.4, 8.5, 13.6, 17.0, and 18.5 degrees 2θ (±0.2 degrees 2θ). In some embodiments, camsylate salt Form I of Compound 1 is characterized by an X-ray powder diffraction pattern substantially in accordance with FIG. 23.

Differential scanning calorimetry (DSC) can also be used to characterize camsylate salt Form I of Compound 1 described herein. In some embodiments, camsylate salt Form I of Compound 1 is characterized by a differential scanning calorimetry thermogram (DSC) comprising an endothermic peak at around 209.8° C. In some embodiments, camsylate salt Form I of Compound 1 is characterized by a melting point onset of about 202.8° C. as determined by differential scanning calorimetry thermogram (DSC). In some embodiments, camsylate salt Form I of Compound 1 is characterized by a differential scanning calorimetry (DSC) thermogram substantially in accordance with FIG. 24.

Thermal gravimetric analysis (TGA) is another technique that can be used to characterize Form I of the camsylate salt of Compound 1 described herein. In some embodiments, Form I of the camsylate salt of Compound 1 is characterized by a weight loss of about 0.23% upon heating to around 205.0° C., as measured by thermal gravimetric analysis (TGA). In some embodiments, Form I of the camsylate salt of Compound 1 is characterized by a thermal gravimetric analysis (TGA) thermogram substantially in accordance with FIG. 24.

Dynamic vapor sorption (DVS) is an additional method that can be used to characterize camsylate salt Form I of Compound 1 described herein. In some embodiments, camsylate salt Form I of Compound 1 is characterized by a weight gain of about 0.35% after undergoing a dynamic vapor sorption cycle (DVS) from about 0% relative humidity (RH) to about 65% RH at 25° C. In some embodiments, camsylate salt Form I of Compound 1 is characterized by a weight gain of about 0.96% after undergoing a dynamic vapor sorption (DVS) cycle from about 5% relative humidity (RH) to about 95% RH at 25° C. In some embodiments, camsylate salt Form I of Compound 1 is characterized by a dynamic vapor sorption (DVS) plot substantially in accordance with FIG. 25.

Microscopy can also be used to characterize camsylate salt Form I of Compound 1 described herein. In some embodiments, scanning electron microscopy (SEM) is used. In some embodiments, camsylate salt Form I of Compound 1 is characterized by an SEM image having predominantly blunt-ended blade and rod particles. In some embodiments, the particles are about <μm to 77 μm, as determined by SEM. In some embodiments, camsylate salt Form I of Compound 1 is characterized by scanning electron microscopy (SEM) images substantially in accordance with FIG. 26.

Figure 27:
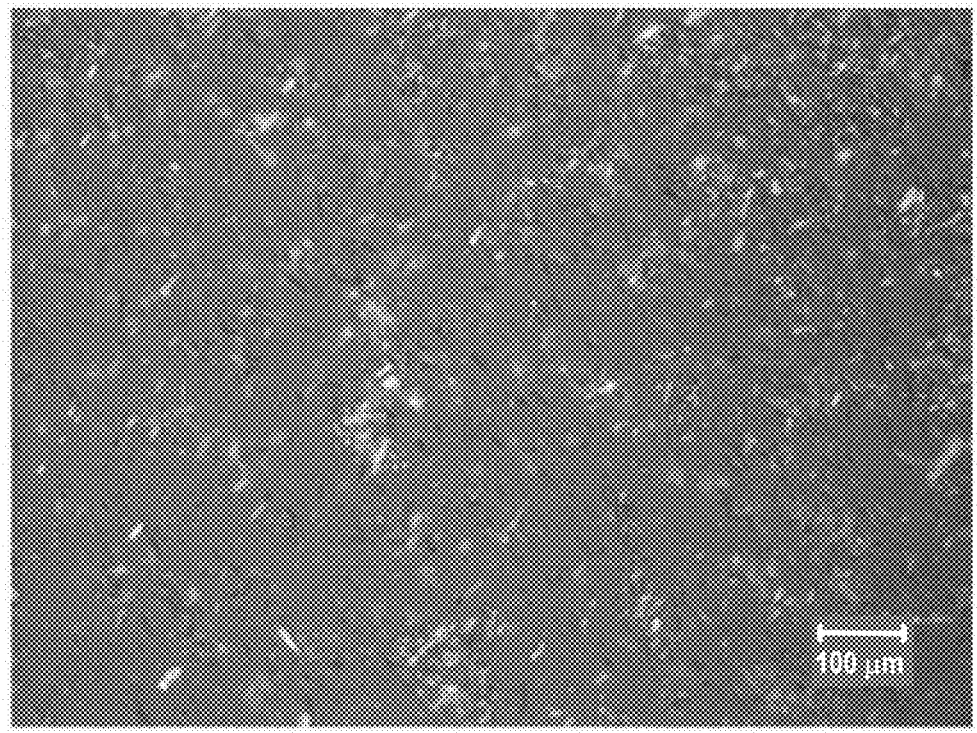
FIG. 27 shows a representative polarized light microscopy (PLM) image of camsylate salt Form I of Compound 1. The magnification shown is 10×.

Polarized light microscopy (PLM) is another technique that can be used to characterize camsylate salt Form I of Compound 1 described herein. In some embodiments, camsylate salt Form I of Compound 1 is characterized by particles ranging in size from about 2.5 to 84 μm as determined by polarized light microscope (PLM). In some embodiments, camsylate salt Form I of Compound 1 is characterized by polarized light microscope (PLM) profile substantially as shown in FIG. 27.

vii. A Edisylate Salt of Compound 1 (Form I)

In some aspects, provided herein is a edisylate salt Form I of Compound 1

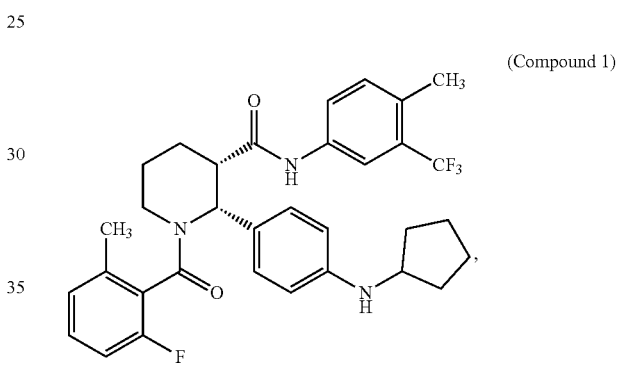

(Compound 1)

which is substantially free of other crystalline or amorphous forms of Compound 1.

In some embodiments, edisylate salt Form I of Compound 1 is characterized by an X-ray powder diffraction pattern comprising peaks at 3.4, 5.6, 12.9, 15.3, 18.1, and 20.8 degrees 2θ (±0.2 degrees 2θ). In some embodiments, edisylate salt Form I of Compound 1 is further characterized by an X-ray powder diffraction pattern comprising peaks at 7.3, 10.7, 14.5, 15.6, 19.1 and 19.7 degrees 2θ (±0.2 degrees 2θ). In some embodiments, edisylate salt Form I of Compound 1 is characterized by an X-ray powder diffraction pattern substantially in accordance with FIG. 28.

Differential scanning calorimetry (DSC) can also be used to characterize edisylate salt Form I of Compound 1 described herein. In some embodiments, edisylate salt Form I of Compound 1 is characterized by a differential scanning calorimetry thermogram (DSC) comprising an endothermic peak at around 213.3° C. In some embodiments, edisylate salt Form I of Compound 1 is characterized by a melting point onset of about 205.2° C. as determined by differential scanning calorimetry thermogram (DSC). In some embodiments, edisylate salt Form I of Compound 1 is characterized by a differential scanning calorimetry (DSC) thermogram substantially in accordance with FIG. 29.

B. Pharmaceutical Compositions

Provided herein are pharmaceutical compositions comprising a salt form of Compound 1 described herein or liquid pharmaceutical compositions prepared using a salt form of Compound 1 described herein. Pharmaceutical compositions will include one or more pharmaceutically acceptable excipients.

The pharmaceutical compositions containing the salt forms of Compound 1 described herein may be in a form suitable for oral use, for example, as tablets, troches, lozenges, liquid formulations, aqueous or oily suspensions, dispersible powders or granules, emulsions and self emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain a salt form of Compound 1 in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein a salt form of Compound 1 is mixed with an inert solid diluent, for example, calcium carbonate, calcium phosphate or kaolin, or as soft gelatin capsules wherein a salt form of Compound 1 is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions for oral use contain a salt form of Compound 1 in admixture with excipients suitable for the manufacture of aqueous suspensions. Such excipients are suspending agents, for example sodium carboxymethylcellulose, methylcellulose, hydroxy-propylmethylcellulose, hydroxy-propylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate as well as other poloxamers (e.g. Poloxamer F-68). The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Accordingly, provided herein is aqueous suspension comprising a salt form of Compound 1 and at least one excipient. In some embodiments, the at least one excipient is at least one suspending agent and/or at least one wetting agent as described above.

Oily suspensions for oral use may be formulated by suspending a salt form of Compound 1 in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

The pharmaceutical compositions may be in the form of a sterile injectable or infusable aqueous or oleagenous solution or suspension. This solution or suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution, isotonic sodium chloride solution, isotonic aqueous buffer solutions, as well as mixtures of saline, a disintegrating agent such as PEG (e.g. PEG 200, PEG 400, PEG 800, etc), and nonionic surfactants such as Tween80. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables and infusables. Compositions for injectable or infusable administration optionally include a local anesthetic such as lignocaine to ease pain at the site of the injection. Ingredients can be supplied pre-mixed or supplied separately, with mixing of the ingredients occurring shortly before use. In some embodiments, mixing shortly before use is desirable to take advantage of the high initial solubility of the salt forms of Compound 1 described herein in certain liquid formulation mixtures.

Injectable or infusible compositions includes, but is not limited to, intravenous administration, intramuscular administration as well as subcutaneous or intrasternal injection. Accordingly, in some embodiments, provided herein is an injectable or infusible solution comprising Compound 1 and at least one wetting agent or solvent, wherein the intravenous pharmaceutical composition is prepared using a salt form of Compound 1 described herein. In some embodiments, the injectable or infusible solution is prepared for intravenous administration. In some embodiments, the injectable or infusible solution is prepared for intramuscular administration. In some embodiments, the injectable or infusible solution is prepared for subcutaneous injection. In some embodiments, the injectable or infusible solution is prepared for intrasternal injection. In some embodiments, the at least one wetting agent or solvent in the injectable or infusible pharmaceutical composition includes saline, a disintegrating agent, and nonionic surfactant.

Injectable or infusible compositions can be prepared at any time that is convenient for the medical practitioner or user; this includes shortly before use or well in advance of use. In some embodiments, the composition is prepared shortly before use. Shortly before use includes 0-24 hours before use, 0-10 hours before use, 0-5 hours before use, or 0-1 hours before use. In some embodiments, the injectable or infusible composition is prepared 0-5 hours before use. Well in advance typically refers to one or more days before use. Accordingly, also provided herein are methods of preparing injectable or infusible solution. The method including, dissolving a salt form of Compound 1 with the at least one wetting agent or solvent to prepare an injectable or infusible solution; and administering the injectable or infusible solution to a subject in need thereof.

Dispersible powders and granules suitable for preparation of an aqueous oral formulations or oral suspensions by the addition of water provide a salt form of Compound 1 in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The compounds of the present invention may also be administered in the form of suppositories for rectal administration of the drug. These compositions can be prepared by mixing a salt form of Compound 1 with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of this invention may also be coupled a carrier that is a suitable polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the invention may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like. In one embodiment of the invention, the compound of the invention is coupled to a polymer or semipermeable polymer matrix that is formed as a stent or stent-graft device.

C. Methods of Treatment

Also provided herein are methods of treating individuals suffering from conditions that are responsive to C5a receptor modulation.

In some aspects provided herein are methods of treating an individual suffering from or susceptible to a disease or disorder involving pathologic activation of C5a receptors, comprising administering to the individual an effective amount of a salt form of Compound 1 or a pharmaceutical formulation including Compound 1 as described herein.

In some embodiments, the salt forms of Compound 1 described herein are used for treating patients suffering from conditions that are responsive to C5a receptor modulation. Conditions that can be Treated by C5a Modulation:

Autoimmune disorders—e.g., Rheumatoid arthritis, systemic lupus erythematosus, Guillain-Barre syndrome, pancreatitis, C3 glomerulopathy (C3G), hidradenitis suppurativa (HS), lupus nephritis, lupus glomerulonephritis, immunoglobulin A (IgA) nephropathy, psoriasis, Crohn's disease, vasculitis, irritable bowel syndrome, dermatomyositis, multiple sclerosis, bronchial asthma, pemphigus, pemphigoid, scleroderma, myasthenia gravis, autoimmune hemolytic and thrombocytopenic states, Goodpasture's syndrome (and associated glomerulonephritis and pulmonary hemorrhage), immunovasculitis, tissue graft rejection, hyperacute rejection of transplanted organs; and the like.

Inflammatory disorders and related conditions—e.g., Neutropenia, sepsis, septic shock, Alzheimer's disease, multiple sclerosis, stroke, inflammatory bowel disease (IBD), age-related macular degeneration (AMD, both wet and dry forms), inflammation associated with severe burns, lung injury, and ischemia-reperfusion injury, osteoarthritis, as well as acute (adult) respiratory distress syndrome (ARDS), chronic pulmonary obstructive disorder (COPD), systemic inflammatory response syndrome (SIRS), atopic dermatitis, psoriasis, chronic urticaria and multiple organ dysfunction syndrome (MODS). Also included are pathologic sequellae associated with insulin-dependent diabetes mellitus (including diabetic retinopathy), lupus nephropathy, Heyman nephritis, membranous nephritis and other forms of glomerulonephritis, contact sensitivity responses, and inflammation resulting from contact of blood with artificial surfaces that can cause complement activation, as occurs, for example, during extracorporeal circulation of blood (e.g., during hemodialysis or via a heart-lung machine, for example, in association with vascular surgery such as coronary artery bypass grafting or heart valve replacement), or in association with contact with other artificial vessel or container surfaces (e.g., ventricular assist devices, artificial heart machines, transfusion tubing, blood storage bags, plasmapheresis, plateletpheresis, and the like). Also included are diseases related to ischemia/reperfusion injury, such as those resulting from transplants, including solid organ transplant, and syndromes such as ischemic reperfusion injury, ischemic colitis and cardiac ischemia. The salt forms of Compound 1 described herein may also be useful in the treatment of age-related macular degeneration (Hageman et al, *P.N.A.S.* 102: 7227-7232, 2005).

Cardiovascular and Cerebrovascular Disorders—e.g., myocardial infarction, coronary thrombosis, vascular occlusion, post-surgical vascular reocclusion, atherosclerosis, traumatic central nervous system injury, and ischemic heart disease. In one embodiment, an effective amount of a salt form of Compound 1 described herein may be administered to a patient at risk for myocardial infarction or thrombosis (i.e., a patient who has one or more recognized risk factor for myocardial infarction or thrombosis, such as, but not limited to, obesity, smoking, high blood pressure, hypercholesterolemia, previous or genetic history of myocardial infarction or thrombosis) in order reduce the risk of myocardial infarction or thrombosis.

Diseases of Vasculitis—Vasculitic diseases are characterized by inflammation of the vessels. Infiltration of leukocytes leads to destruction of the vessel walls, and the complement pathway is believed to play a major role in initiating leukocyte migration as well as the resultant damage manifested at the site of inflammation (Vasculitis, Second Edition, Edited by Ball and Bridges, Oxford University Press, pp 47-53, 2008). The salt forms of Compound 1 described herein can be used to treat vasculitis, including anti-neutrophil cytoplasmic antibody associate vasculitis (or ANCA-associated vasculitis, which includes microscopic polyangiitis, eosinophilic granulomatosis with polyangitis, and granulomatosis with polyangiitis, which is also known as Wegener's disease), Churg-Strauss syndrome, Henoch-Schonlein purpura, polyateritis nodosa, Rapidly Progressive Glomerulonephritis (RPGN), cryoglobulinaemia, giant cell arteritis (GCA), Behcet's disease and Takayasu's arteritis (TAK).

HIV infection and AIDS—the salt forms of Compound 1 described herein may be used to inhibit HIV infection, delay AIDS progression or decrease the severity of symptoms or HIV infection and AIDS.

Neurodegenerative disorders and related diseases—Within further embodiments, the salt forms of Compound 1 described herein may be used to treat Alzheimer's disease, multiple sclerosis, and cognitive function decline associated with cardiopulmonary bypass surgery and related procedures.

Cancers—The salt forms of Compound 1 described herein are also useful for the treatment of cancers and precancerous conditions in a subject. Specific cancers that can be treated include, but are not limited to, sarcomas, carcinomas, and mixed tumors. Exemplary conditions that may be treated according to the present invention include fibrosarcomas, liposarcomas, chondrosarcomas, osteogenic sarcomas, angiosarcomas, lymphangiosarcomas, synoviomas, mesotheliomas, meningiomas, leukemias, lymphomas, leiomyosarcomas, rhabdomyosarcomas, squamous cell carcinomas, basal cell carcinomas, adenocarcinomas, papillary carcinomas, cystadenocarcinomas, bronchogenic carcinomas, melanomas, renal cell carcinomas, hepatocellular carcinomas, transitional cell carcinomas, choriocarcinomas, seminomas, embryonal carcinomas, wilm's tumors, pleomorphic adenomas, liver cell papillomas, renal tubular adenomas, cystadenomas, papillomas, adenomas, leiomyomas, rhabdomyomas, hemangiomas, lymphangiomas, osteomas, chondromas, lipomas and fibromas.

In some embodiments, the salt forms of Compound 1 described herein can be used for the treatment of diseases selected from the group consisting of sepsis (and associated disorders), COPD, rheumatoid arthritis, lupus nephritis and multiple sclerosis.

In some embodiments, the salt forms of Compound 1 described herein can be used for the treatment of diseases selected from the group consisting of anti-neutrophil cytoplasmic antibody associate (ANCA) vasculitis, C3 glomerulopathy, hidradenitis suppurativa, and lupus nephritis.

Treatment methods provided herein include, in general, administration to a patient an effective amount of a salt form of Compound 1. Suitable patients include those patients suffering from or susceptible to (i.e., prophylactic treatment) a disorder or disease identified herein. Typical patients for treatment as described herein include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a patient an effective amount of the salt form of Compound 1 described herein. The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). In some embodiments, the salt forms of Compound 1 described herein is administered to a patient (e.g., a human) orally. In some embodiments, the salt forms of Compound 1 described herein is administered to a patient (e.g., a human) intravenously, intramuscularly, or via subcutaneous or intrasternal injection. The effective amount may be an amount sufficient to modulate C5a receptor activity and/or an amount sufficient to reduce or alleviate the symptoms presented by the patient. Preferably, the amount administered is sufficient to yield a plasma concentration of the compound (or its active metabolite, if the compound is a pro-drug) high enough to detectably inhibit white blood cell (e.g., neutrophil) chemotaxis in vitro.

For treatment of most disorders via oral administration, a person of skill in the art may determine the appropriate frequency of administration. In some embodiments, a frequency of administration of 4 times daily or less is preferred. In some embodiments, a dosage regimen of 2 times daily is used. In some embodiments, once daily administration is used. The patient may be administered a salt form of Compound 1 in a fed or fasted state. In some embodiments, the patient takes the salt form of Compound 1 with food. In some embodiments, the patient takes the salt form of Compound 1 without food.

For treatment of most disorders via intravenous, intramuscular administration or via subcutaneous or intrasternal injection, a person of skill in the art may determine the appropriate frequency of administration. In some embodiments, the frequency of administration is about once every two weeks. In some embodiments, the frequency of administration is about once every week. In some embodiments, the frequency of administration is about three times a week. In some embodiments, the frequency of administration is about 2 to 5 times a week. In some embodiments, the frequency of administration is about once every other day. In some embodiments, the frequency of administration is about once a day.

It will be understood, however, that the specific dose level and treatment regimen for any particular patient will depend upon a variety of factors including the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

Dosage levels of the order of from about 0.1 mg to about 140 mg per kilogram of body weight per day are useful in the treatment or preventions of conditions involving pathogenic C5a activity (about 0.5 mg to about 7 g per human patient per day). The amount of the salt form of Compound 1 that may be combined with the carrier materials to produce a single dosage form will vary depending upon the host treated and the particular mode of administration. Dosage unit forms will generally contain between from about 1 mg to about 500 mg of the salt form of Compound 1. When administered orally, transdermally, intravenously, or subcutaneously, it is preferred that sufficient amount of the salt form of Compound 1 be administered to achieve a serum concentration of 5 ng (nanograms)/mL-10 μg (micrograms)/mL serum, more preferably sufficient compound to achieve a serum concentration of 20 ng-1 μg/ml serum should be administered, most preferably sufficient compound to achieve a serum concentration of 50 ng/ml-200 ng/ml serum should be administered. For direct injection into the synovium (for the treatment of arthritis) sufficient amounts of the salt form of Compound 1 should be administered to achieve a local concentration of approximately 1 micromolar.

D. Combination Therapy

The presently disclosed methods may include combination therapy with one or more additional therapeutic agents that are used in the treatment, prevention, suppression or amelioration of the diseases or conditions involving pathologic activation of C5a receptors. Such one or more additional therapeutic agents may be administered, by a route and in an amount commonly used therefor, contemporaneously or sequentially with the salt forms of Compound 1 described herein. When a salt form of Compound 1 described herein is used contemporaneously with the additional therapeutic agent, a pharmaceutical composition containing such other drugs in addition to the salt form of Compound 1 is preferred. Accordingly, the pharmaceutical compositions of the present disclosure include those that also contain one or more other active ingredients or therapeutic agents, in addition to the salt forms of Compound 1 described herein.

Examples of the one or more additional therapeutic agents are corticosteroids, steroids, immunosuppressants, Immunoglobulin G agonists, Dipeptidyl peptidase IV inhibitors, Lymphocyte function antigen-3 receptor antagonists, Interleukin-2 ligands, Interleukin-1 beta ligand inhibitors, IL-2 receptor alpha subunit inhibitors, HGF gene stimulators, IL-6 antagonists, IL-5 antagonists, Alpha 1 antitrypsin stimulators, Cannabinoid receptor antagonists, Histone deacetylase inhibitors, AKT protein kinase inhibitors, CD20 inhibitors, Abl tyrosine kinase inhibitors, JAK tyrosine kinase inhibitors, TNF alpha ligand inhibitors, Hemoglobin modulators, TNF antagonists, proteasome inhibitors, CD3 modulators, Hsp 70 family inhibitors, Immunoglobulin agonists, CD30 antagonists, tubulin antagonists, Sphingosine-1-phosphate receptor-1 agonists, connective tissue growth factor ligand inhibitors, caspase inhibitors, adrenocorticotrophic hormone ligands, Btk tyrosine kinase inhibitors, Complement C1s subcomponent inhibitors, Erythropoietin receptor agonists, B-lymphocyte stimulator ligand inhibitors, Cyclin-dependent kinase-2 inhibitors, P-selectin glycoprotein ligand-1 stimulators, mTOR inhibitors, Elongation factor 2 inhibitors, Cell adhesion molecule inhibitors, Factor XIII agonists, Calcineurin inhibitors, Immunoglobulin G1 agonists, Inosine monophosphate dehydrogenase inhibitors, Complement C1s subcomponent inhibitors, Thymidine kinase modulators, Cytotoxic T-lymphocyte protein-4 modulators, Angiotensin II receptor antagonists, Angiotensin II receptor modulators, TNF superfamily receptor 12A antagonists, CD52 antagonists, Adenosine deaminase inhibitors, T-cell differentiation antigen CD6 inhibitors, FGF-7 ligands, dihydroorotate dehydrogenase inhibitors, Syk tyrosine kinase inhibitors, Interferon type I receptor antagonists, Interferon alpha ligand inhibitors, Macrophage migration inhibitory factor inhibitors, Integrin alpha-V/beta-6 antagonists, Cysteine protease stimulators, p38 MAP kinase inhibitors, TP53 gene inhibitors, Shiga like toxin I inhibitors, Fucosyltransferase 6 stimulators, Interleukin 22 ligands, IRS1 gene inhibitors, Protein kinase C stimulators, Protein kinase C alpha inhibitors, CD74 antagonists, Immunoglobulin gamma Fc receptor IIB antagonists, T-cell antigen CD7 inhibitors, CD95 antagonists, N acetylmannosamine kinase stimulators, Cardiotrophin-1 ligands, Leukocyte elastase inhibitors, CD40 ligand receptor antagonists, CD40 ligand modulators, IL-17 antagonists, TLR-2 antagonists, Mannan-binding lectin serine protease-2 (MASP-2) inhibitors, Factor B inhibitors, Factor D inhibitors, C3aR modulators, C5aR2 modulators, T cell receptor antagonists, PD-1 inhibitors, PD-L1 inhibitors, TIGIT inhibitors, TIM-3 inhibitors, LAG-3 inhibitors, VISTA inhibitors, STING agonists, IDO inhibitors, adenosine receptor modulators, CD39 inhibitors, CD73 inhibitors, antagonists of the chemokine receptors, especially CXCR1, CXCR2, CXCR3, CXCR4, CXCR7, CCR1, CCR2, CCR3, CCR4, CCR5, CCR7, CCR7, CCR9, CX3CR1 and CXCR6, and combinations thereof.

In some embodiments, the additional therapeutic agent used in the therapeutic methods herein, is selected from the group consisting of obinutuzumab, rituximab, ocrelizumab, tositumomab, obinutuzumab, ibritumomab, cyclophosphamide, prednisone, hydrocortisone, hydrocortisone acetate, cortisone acetate, tixocortol pivalate, prednisolone, methylprednisolone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-valerate, halometasone, alclometasone dipropionate, beclomethasone, betamethasone valerate, betamethasone dipropionate, prednicarbate, clobetasone-17-butyrate, clobetasol-17-propionate, fluocortolone caproate, fluocortolone pivalate, fluprednidene acetate, hydrocortisone-17-butyrate, hydrocortisone-17-aceponate, hydrocortisone-17-buteprate, ciclesonide and prednicarbate, GB-0998, immuglo, begelomab, alefacept, aldesleukin, gevokizumab, daclizumab, basiliximab, inolimomab, beperminogene perplasmid, sirukumab, tocilizumab, clazakizumab, mepolizumab, fingolimod, panobinostat, triciribine, nilotinib, imatinib, tofacitinib, momelotinib, peficitinib, itacitinib, infliximab, PEG-bHb-CO, etanercept, ixazomib, bortezomib, muromonab, otelixizumab, gusperimus, brentuximab vedotin, Ponesimod, KRP-203, FG-3019, emricasan, corticotropin, ibrutinib, cinryze, conestat, methoxy polyethylene glycol-epoetin beta, belimumab, blisibimod, atacicept, seliciclib, neihulizumab, everolimus, sirolimus, denileukin diftitox, LMB-2, natalizumab, catridecacog, ciclosporin, tacrolimus, voclosporin, voclosporin, canakinumab, mycophenolate, mizoribine, CE-1145, TK-DLI, abatacept, belatacept, olmesartan medoxomil, sparsentan, TXA-127, BIIB- 023, alemtuzumab, pentostatin, itolizumab, palifermin, leflunomide, PRO-140, cenicriviroc, fostamatinib, anifrolumab, sifalimumab, BAX-069, BG-00011, losmapimod, QPI-1002, ShigamAbs, TZ-101, F-652, reparixin, ladarixin, PTX-9908, aganirsen, APH-703, sotrastaurin, sotrastaurin, milatuzumab, SM-101, T-Guard, APG-101, DEX-M74, cardiotrophin-1, tiprelestat, ASKP-1240, BMS-986004, HPH-116, KD-025, OPN-305, TOL-101, defibrotide, pomalidomide, Thymoglobulin, laquinimod, remestemcel-L, Equine antithymocyte immunoglobulin, Stempeucel, LIV-Gamma, Octagam 10%, t2c-001, 99mTc-sestamibi, Clairyg, Prosorba, pomalidomide, laquinimod, teplizumab, FCRx, solnatide, foralumab, ATIR-101, BPX-501, ACP-01, ALLO-ASC-DFU, irbesartan+propagermanium, ApoCell, cannabidiol, RGI-2001, saratin, anti-CD3 bivalent antibody-diphtheria toxin conjugate, NOX-100, LT-1951, OMS721, ALN-CC5, ACH-4471, AMY-101, Acthar gel, and CD4+CD25+ regulatory T-cells, MEDI7814, P32, P59, pembrolizumab, nivolumab, atezolizumab, avelumab, durvalumab, CCX354, CCX721, CCX9588, CCX140, CCX872, CCX598, CCX6239, CCX587, CCX624, CCX282, CCX025, CCX507, CCX430, CCX765, CCX758, CCX771, CCX662, CCX650, and combinations thereof.

E. Methods of Preparation

Crude Compound 1 can be prepared as described previously. See, for example, WO2010/075257 and WO2016/053890, the contents of each are incorporated by reference in their entirety for all purposes.

The various salt forms described herein can be prepared as described in the provided Examples. It is understood that there may be more than one crystallization method that will yield the described tosylate, besylate, napsylate, napadisylate, camsylate, and edisylate salt forms.

IV. Examples

The following examples are provided to help illustrate the described invention and are not intended to limit the scope of what the inventors regard as their invention.

Example 1: A Besylate Salt of Compound 1 (Form I)

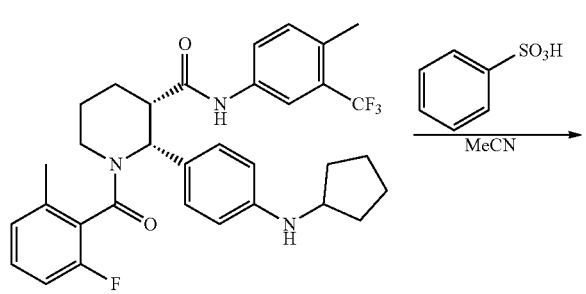

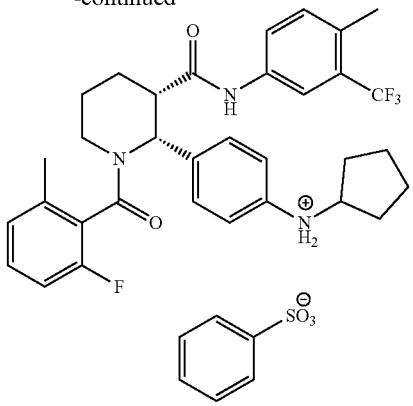

A 3-L round bottom flask equipped with a magnetic stirrer was charged with (2R,3S)-2-(4-(cyclopentylamino)phenyl)-1-(2-fluoro-6-methylbenzoyl)-N-(4-methyl-3-(trifluoromethyl)phenyl)piperidine-3-carboxamide (Compound 1, 250 g, 430 mmol) and MeCN (1.84 L, 8 vol). The resulting mixture was stirred and heated to 75° C. (internal temperature) for 30 min to form a clear solution, and filtered through polyethylene frit filter and rinsed with MeCN (230 mL). To this solution at 60° C. was slowly added a pre-filtered solution of benzenesulfonic acid hydrate (77.9 g, 442 mmol (based on monohydrate), 1.03 eq) in MeCN (276 mL, 3 vol) over 10 min and rinsed with MeCN (92 mL) (internal temperature dropped to 55° C.). The resulting solution was cooled to 50° C., seeded with besylate crystals of Compound 1 (~100 mg) and slowly cooled to 45° C. over 1 h. The resulting mixture was slowly cooled to RT and stirred for 42 h. The solid was collected by filtration, washed with MeCN (230 mL×2), air-dried and then dried in an oven under vacuum at 50° C. overnight (48 h) to afford N-cyclopentyl-4-((2R,3S)-1-(2-fluoro-6-methylbenzoyl)-3-((4-methyl-3-(trifluoromethyl)phenyl)-carbamoyl)piperidin-2-yl)benzenaminium benzenesulfonate as off-white crystals, with a recovery yield of 266.5 g (84%). $^1$H NMR (400 MHz, DMSO-d$_6$) (RT) δ 10.44 (s, 1H), 7.90-7.83 (m, 1H), 7.65-6.95 (m, 14H), 6.42-6.34 (m, 1H), 6.05-5.00 (br, 1H), 3.85-3.70 (m, 1H), 3.22-3.00 (m, 3H), 2.38-2.28 (m, 4H), 2.20-1.40 (m, 15H); (65° C.) δ 10.22 (d, J=8.4 Hz, 1H), 7.85 (d, J=8.4 Hz, 1H), 7.68-6.70 (m, 15H), 6.44-6.35 (m, 1H), 3.72-3.65 (m, 1H), 3.25-2.98 (m, 3H), 2.40-2.28 (m, 4H), 2.22-1.40 (m, 15H). MS: (ES) m/z calculated for $C_{33}H_{36}F_4N_3O_2$ [M+H]$^+$ 582.3, found 582.2. A plot of the XRPD is shown in FIG. 1, and Table 1, below, summarizes significant peaks observed in the XRPD plot. HPLC (both achiral analytical and chiral): >99%. Elemental Analysis consistent with formula of $C_{39}H_{41}F_4N_3O_5S$, KF: 0.66%.

TABLE 1

Significant Peaks in the besylate salt of Compound 1 (Form I)
Significant Peaks
2-theta (deg)

| | |
|---|---|
| 6.66 | 18.06 |
| 7.65 | 18.50 |
| 9.62 | 18.90 |
| 10.36 | 19.94 |
| 10.88 | 21.10 |
| 11.04 | 21.78 |
| 13.28 | 22.10 |
| 14.50 | 23.72 |
| 15.42 | 24.04 |

TABLE 1-continued

Significant Peaks in the besylate salt of Compound 1 (Form I)
Significant Peaks
2-theta (deg)

| | |
|---|---|
| 15.77 | 25.24 |
| 15.94 | 26.18 |
| 16.18 | 26.64 |
| 16.74 | 28.20 |
| 17.62 | 28.98 |

Figure 2:
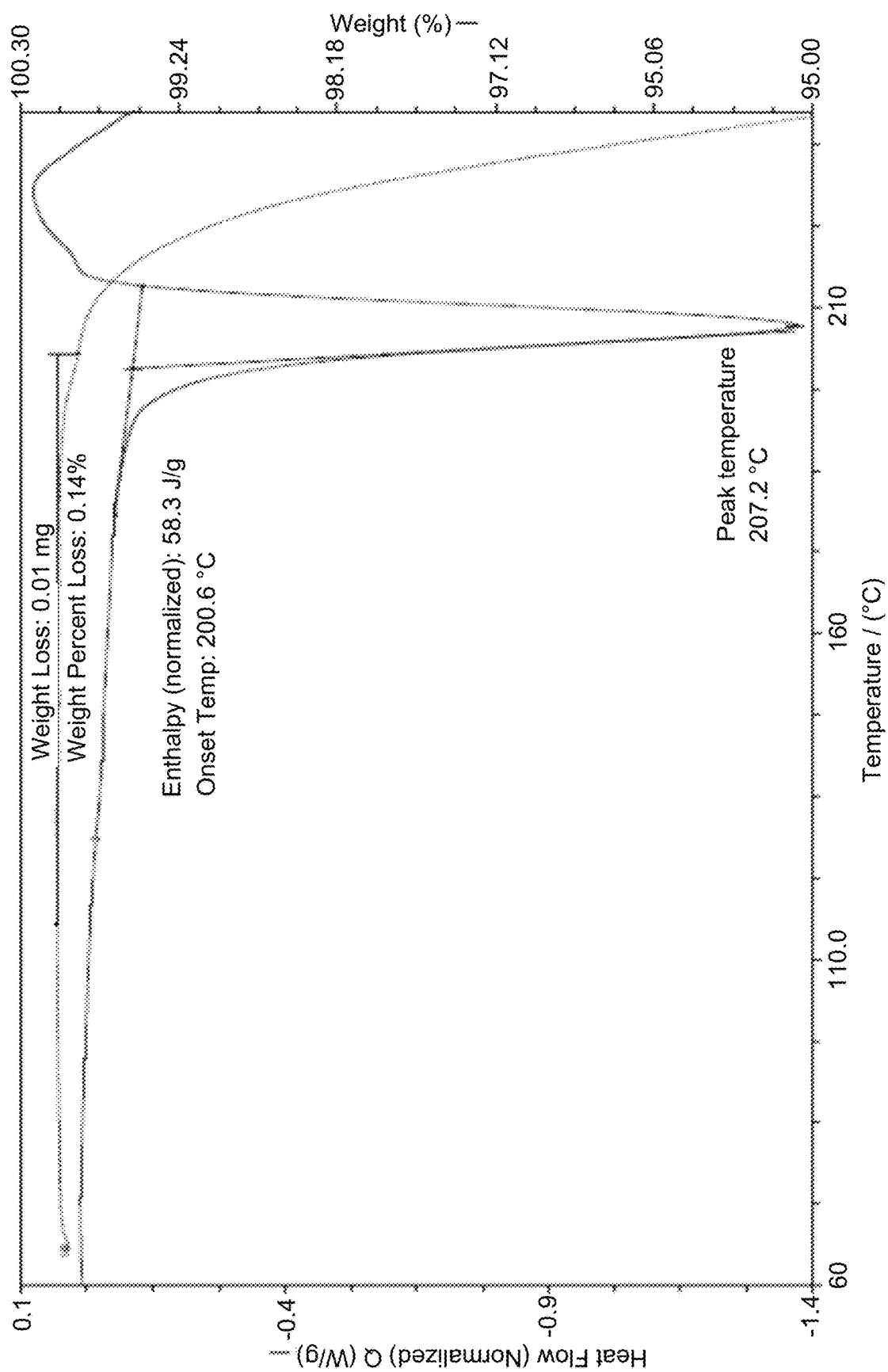
FIG. 2 shows the differential scanning calorimetry (DSC) thermogram as well as the thermal gravimetric analysis (TGA) of besylate salt Form I of Compound 1.

Differential scanning calorimetry (DSC) was performed on the collected crystals using a DSC25 from TA Instruments~Waters LLC. Sample was weighed into a standard aluminum pan and sealed by a standard aluminum lid with pinhole. The measurement was completed by using 10° C./min scanning rate, under a nitrogen purge. DSC analysis determined that the melting point (onset) is about 200.6° C. (DSC). The DSC plot also exhibits an endothermic peak at around 207.2° C. A plot of the DSC thermogram is shown in FIG. 2.

TGA data was collected on a TA instrument Q500 TGA. Each sample was loaded onto a pre-tared platinum crucible; the balance and furnace were purged with nitrogen prior to the analysis with a flow rate set as 40±5 and 60±5 mL/min, respectively. The heating process was programmed to start at the ambient temperature with a 10° C./min ramp. The TGA analysis determined that besylate salt Form I of Compound 1 exhibits about a 0.14% weight loss upon heating to around 202.9° C. A plot of the TGA thermogram is shown in FIG. 2 (upper trace).

To evaluate the hygroscopicity and physical stability of the collected crystals under different humidity, dynamic vapor sorption (DVS) data was collected at 25° C. after the sample was pre-equilibrated at 0% RH to remove unbounded water. DVS was measured using a VTI SGA-100 Vapor Sorption Analyzer. Sorption and desorption data was collected over a range from 5% to 95% RH at 10% RH increments under a nitrogen purge. The equilibrium criterion used for analysis was less than 0.0100% weight change in 5 minutes with a maximum equilibrium time of 3 hours. Parameters for DVS test are listed in Table 2.

TABLE 2

Parameters for DVS test

| Parameters | Value |
|---|---|
| Temperature | 25° C. |
| dm/dt | 0.0100% |
| Min. dm/dt stability duration | 5 min |
| Max. equilibrium time | 3 hours |
| RH range | 5% RH-95% RH-5% RH |
| Humidity increment | 10% RH |
| RH step size | 19 |

Figure 3:
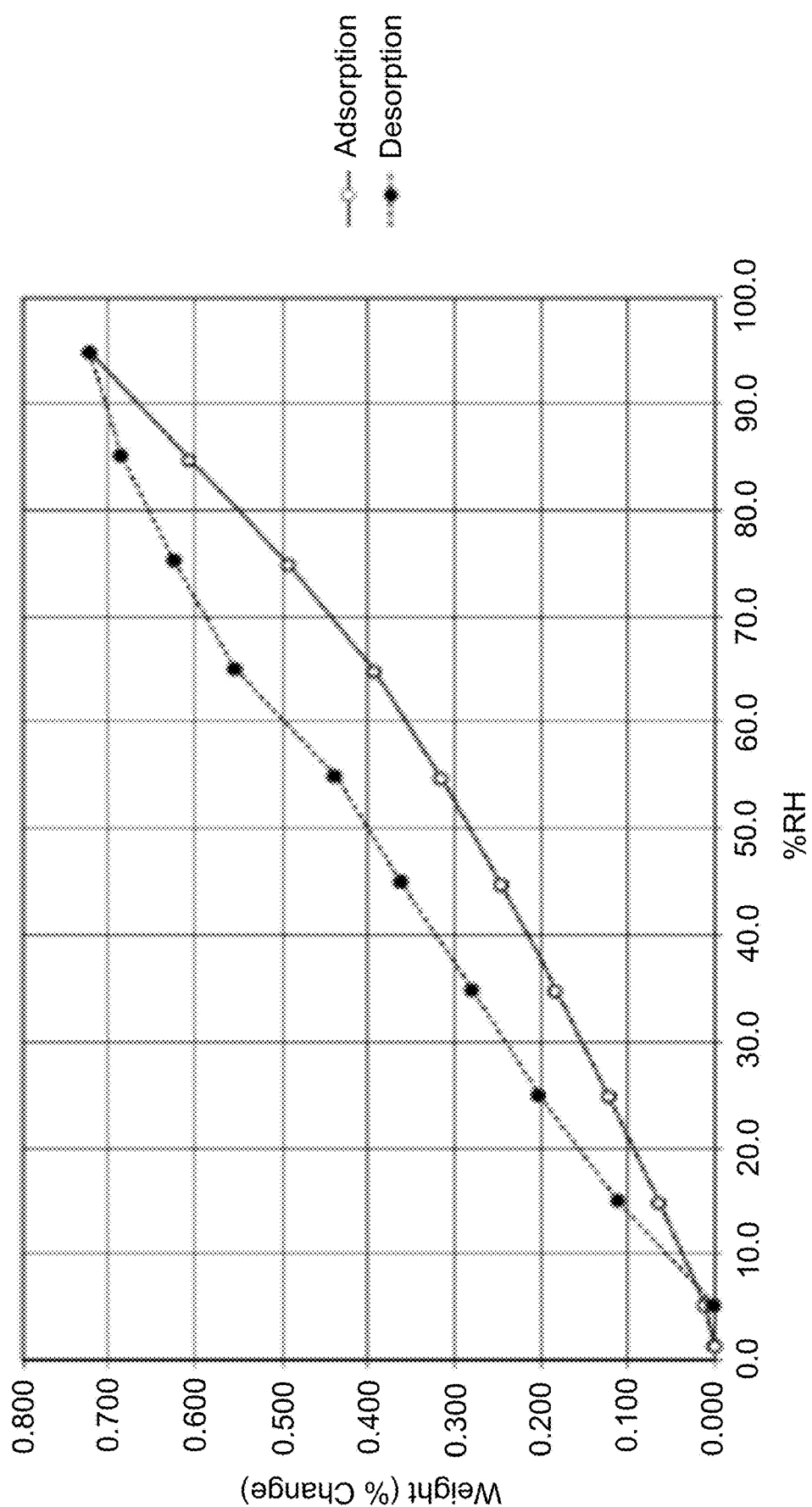
FIG. 3 shows dynamic vapor sorption (DVS) plot of besylate salt Form I of Compound 1.

A plot of the DVS measurement is shown in FIG. 3. A 0.73% weight change from 5% to 95% relative humidity (RH) was measured. A weight change of about 0.5% from about 0% relative humidity (RH) to about 75% relative humidity was also measured. No change in XRPD was observed before and after the DVS measurement (data not shown).

Figure 4:
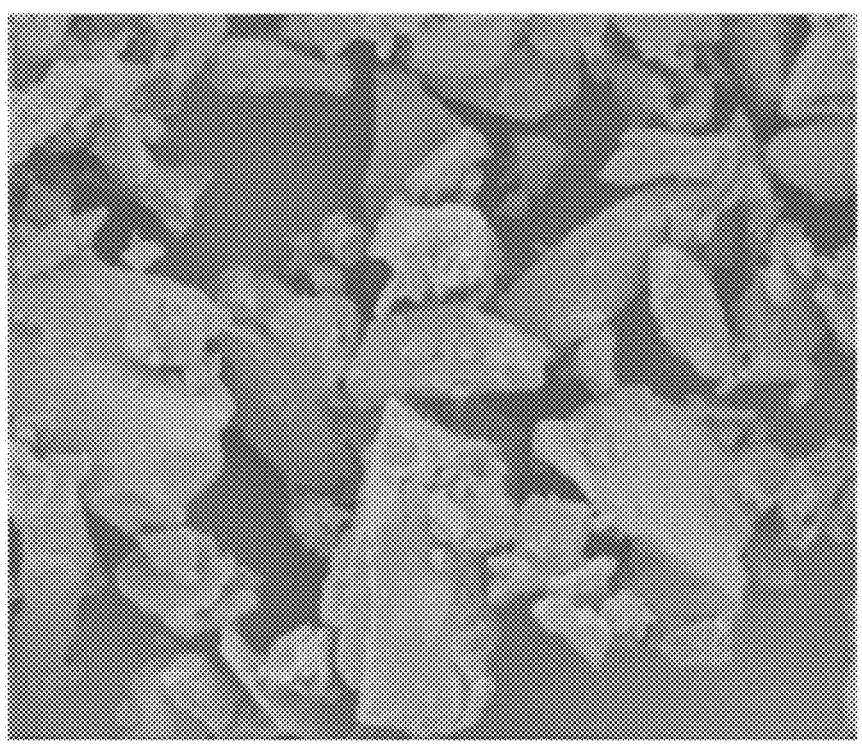
FIG. 4 shows a representative scanning electron microscopy (SEM) image of besylate salt Form I of Compound 1. The magnification shown is 5,000×.

The collected crystals were observed under magnification using a FEI Quanta 200 scanning electron microscope equipped with an Everhart Thornley (ET) detector. Images were collected and analyzed using xTm (v. 2.01) and XT Docu (v. 3.2) software, respectively. The magnification was verified using a National Institute of Standards and Technology (NIST)-Traceable standard. The samples were prepared for analysis by placing a small amount on a carbon adhesive tab supported on an aluminum mount. The sample was then sputter coated twice (in different orientations) with Au/Pd using a Cressington 108 auto Sputter Coater at approximately 20 mA and 0.13 mbar (Ar) for 75 seconds. A representative image of the crystals is shown in FIG. 4. When observed under magnification the crystals were prismatic or anhedral ranging in size from ~1 to 73 µm.

The collected crystals were observed under magnification using polarized light microscopy (a Leica DM LP microscope equipped with a Spot Insight color camera). Different objectives were used with crossed polarized and a first order red compensator to view the sample. Sample was placed on a glass slide, a #1.5 cover glass was placed over the sample, and a drop of mineral oil was added. Images were acquired at ambient temperature using Spot Advanced software (v. 4.5.9). Micrometer bar was inserted onto the image as a reference for size. Representative images of the crystals are shown in FIG. 5. When observed under magnification the crystals were acicular, blades, and anhedral ranging in size from ~2.5 to 83 µm.

The stability of the collected crystals were tested by storing the crystals at 40° C. and 75% relative humidity for 45 days. These conditions did not result in any appreciable decomposition as shown by HPLC, LCMS and NMR analysis (data not shown). Heating at 55° C. in a vacuum oven for 24 h or 75° C. for 1 week (open to air) did not result in any appreciable decomposition as shown by HPLC, LCMS and NMR analysis (data now shown). The physical forms of both samples remained the same based on XRPD take before and after the tests (data not shown).

Example 2: A Besylate Salt of Compound 1 (Form II)

Figure 6:
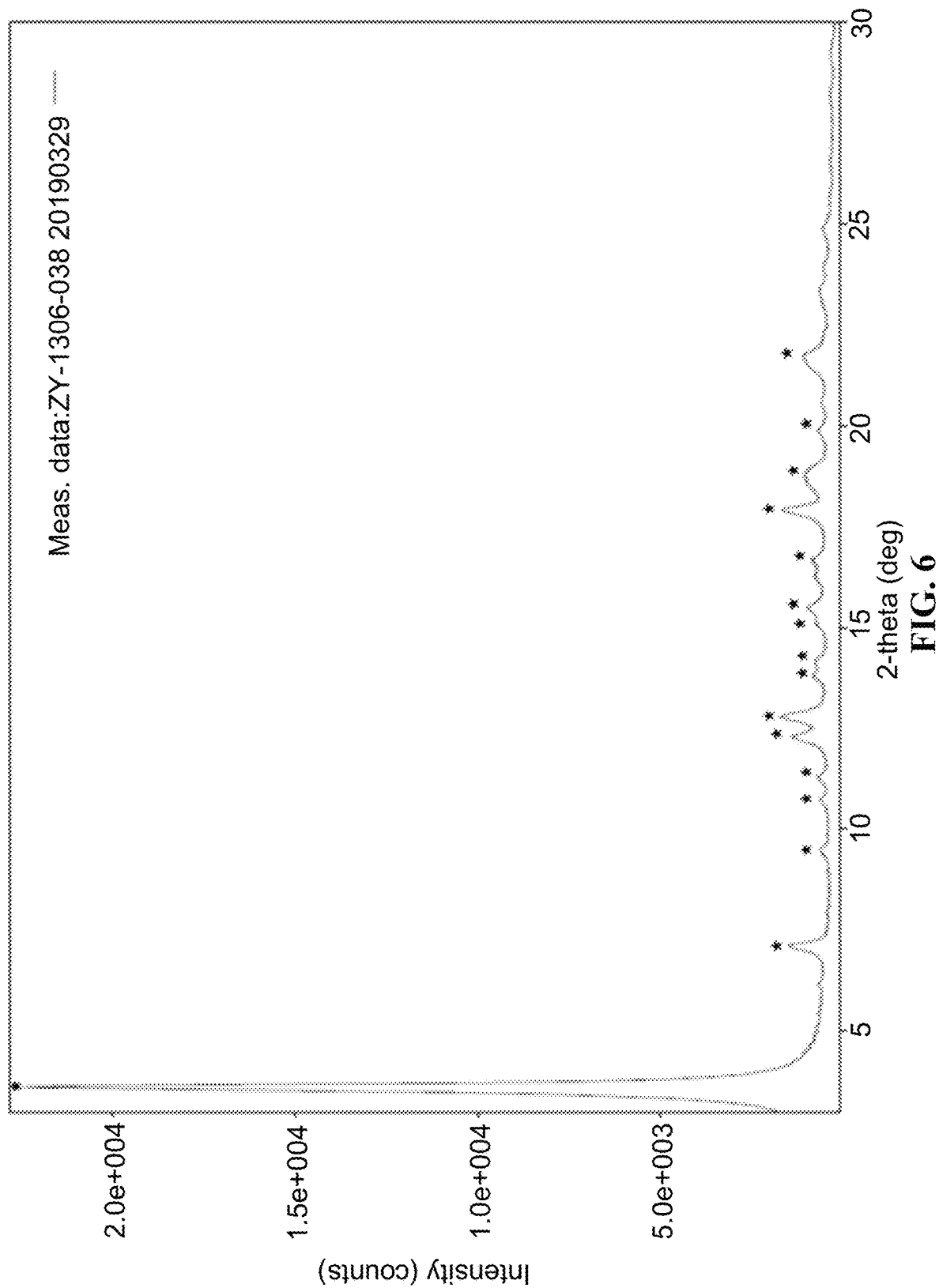
FIG. 6 shows X-ray powder diffraction (XRPD) patterns of besylate salt Form II of Compound 1.

A 250-mL round bottom flask equipped with a magnetic stirrer was charged with (2R,3S)-2-(4-(cyclopentylamino) phenyl)-1-(2-fluoro-6-methylbenzoyl)-N-(4-methyl-3-(trifluoromethyl)phenyl)piperidine-3-carboxamide (Compound 1, 5.18 g, 8.9 mmol) and MeCN (70 mL, 14 vol). The resulting mixture was stirred and heated to 70° C. (hot plate temperature) for 20 min to form a clear solution and then cooled to 65° C. (hot plate temperature). To this solution was slowly added a solution of benzenesulfonic acid hydrate (1.73 g, 9.81 mmol (based on monohydrate), 1.1 eq) in DI $H_2O$ (1.5 mL) and MeCN (15 mL) over 3 min and rinsed with MeCN (10 mL). The resulting solution was stirred at the same temperature for 15 min and then filtered through polyethylene frit filter and rinsed with MeCN (10 mL). The resulting solution was stirred at 65° C. (hot plate temperature) for 30 min slowly cooled down to RT and stirred overnight (18 h). The resulting solution was seeded with besylate crystals of Compound 1 (~50 mg) and stirred at the same temperature for 2 h. The solid was collected by filtration, washed with MeCN (15 mL×2), air-dried (1 h) and then dried under high-vacuum overnight (18 h) to afford N-cyclopentyl-4-((2R,3S)-1-(2-fluoro-6-methylbenzoyl)-3-((4-methyl-3-(trifluoromethyl)phenyl)-carbamoyl)piperidin-2-yl)benzenaminium benzenesulfonate as off-white crystals, with a recovery yield of 2 g (30%). $^1$H NMR (400 MHz, DMSO-$d_6$) δ 10.44 (s, 1H), 7.90-7.83 (m, 1H), 7.65-7.25 (m, 10H), 7.18-7.07 (m, 3H), 6.42-6.34 (m, 1H), 4.85-4.00 (br, 2H), 3.85-3.70 (m, 1H), 3.22-3.00 (m, 3H), 2.38-2.28 (m, 4H), 2.20-1.40 (m, 15H); (65° C.) δ 10.22 (d, J=8.4 Hz, 1H), 7.85 (d, J=8.4 Hz, 1H), 7.68-7.56 (m, 3H), 7.44-7.20 (m, 6H), 7.18-6.70 (m, 4H), 6.44-6.35 (m, 1H), 6.20-5.20 (br, 2H), 3.72-3.65 (m, 1H), 3.25-2.98 (m, 3H), 2.40-2.28 (m, 4H), 2.22-1.40 (m, 15H). MS: (ES) m/z calculated for $C_{33}H_{36}F_4N_3O_2$ [M+H]$^+$ 582.3, found 582.2. A plot of the XRPD is shown in FIG. 6, and Table 3, below, summarizes significant peaks observed in the XRPD plot. HPLC: >99%. Elemental Analysis consistent with formula of $C_{39}H_{41}F_4N_3O_5S$, KF: 0.42%.

TABLE 3

Significant Peaks in the besylate salt of Compound 1 (Form I)
Significant Peaks
2-theta (deg)

| | |
|---|---|
| 3.62 | 15.12 |
| 7.12 | 15.48 |
| 9.48 | 16.22 |
| 10.74 | 16.66 |
| 11.32 | 17.92 |
| 12.30 | 18.74 |
| 12.80 | 18.88 |
| 13.84 | 21.72 |
| 14.10 | |

Figure 7:
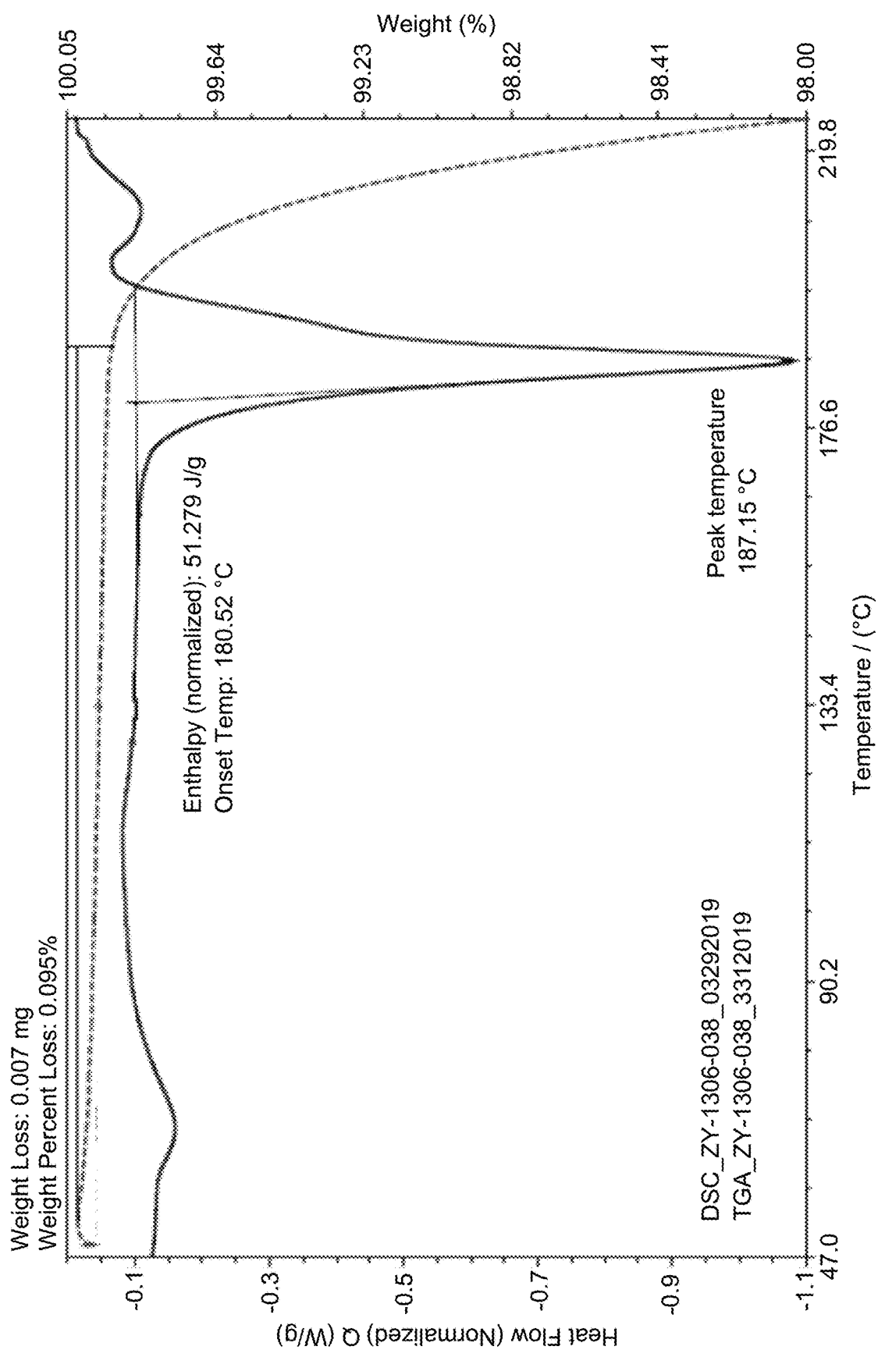
FIG. 7 shows the differential scanning calorimetry (DSC) thermogram as well as the thermal gravimetric analysis (TGA) of besylate salt Form II of Compound 1.

Differential scanning calorimetry (DSC) was performed as described in Example 1. DSC analysis determined that the melting point (onset) is about 180.5° C. (DSC). The DSC plot also exhibits an endothermic peak at around 187.2° C. A plot of the DSC thermogram is shown in FIG. 7 (lower trace).

TGA was performed as described in Example 1. The TGA analysis determined that besylate salt Form II of Compound 1 exhibits about a 0.095% weight loss upon heating to around 189.5° C. A plot of the TGA thermogram is shown in FIG. 7 (upper trace).

Example 3: A Tosylate Salt of Compound 1 (Form I)

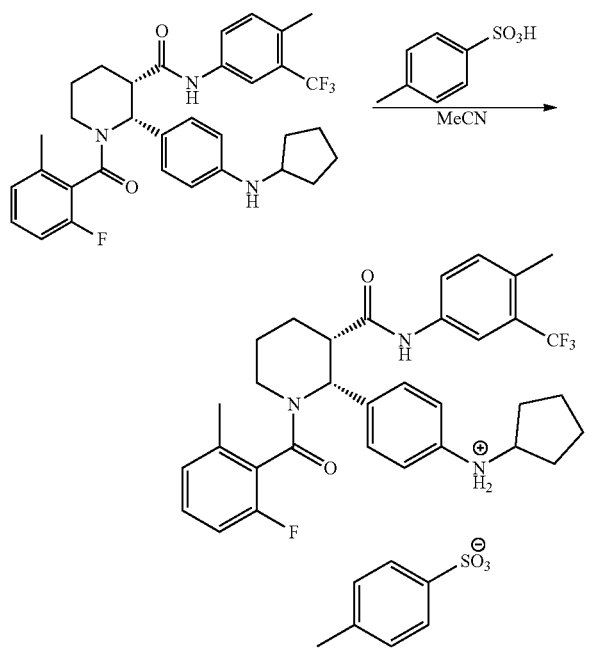

Figure 8:
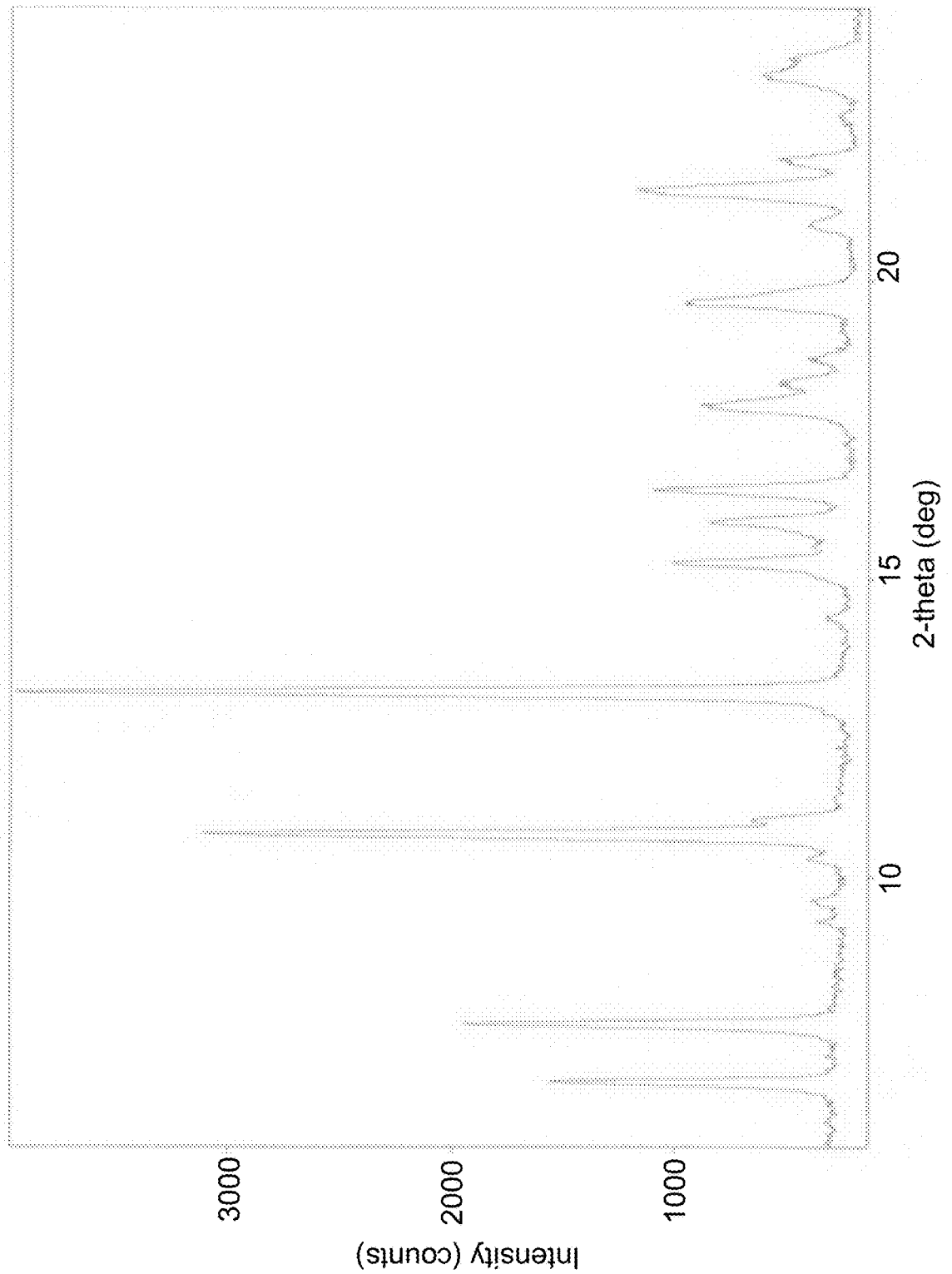
FIG. 8 shows X-ray powder diffraction (XRPD) patterns of tosylate salt Form I of Compound 1.

A 5-L three neck flask equipped with an overhead stirrer was charged with (2R,3S)-2-(4-(cyclopentylamino)phenyl)-1-(2-fluoro-6-methylbenzoyl)-N-(4-methyl-3-(trifluoromethyl)phenyl)piperidine-3-carboxamide (Compound 1, 261.2 g, 449.1 mmol) and MeCN (2 L, 8 vol). The resulting mixture was stirred and heated to 75° C. (internal temperature) for 20 min to form a clear solution. The solution was cooled to 65° C. (internal temperature), and a solution of para-toluenesulfonic acid hydrate (1.25 hydrate corrected by KF analysis, 89.1 g, 458 mmol, 1.02 eq) in deionized $H_2O$ (45 mL, 0.5 vol) was added slowly over 20 min and rinsed with MeCN (45 mL×2) (maintaining the internal temperature between 60 to 65° C.). The resulting solution was stirred at the same temperature for 15 min and then filtered through polyethylene frit filter and rinsed with MeCN (200 mL). The filtrate was cooled to 45° C. and seeded with tosylate crystals of Compound 1 (~100 mg) and stirred at the same temperature for 1 h. The resulting mixture was slowly cooled to RT and stirred overnight (18 h). The solid was collected by filtration, washed with MeCN (250 mL×2), air-dried (1 h) and then dried in an oven under vacuum at 50° C. overnight (24 h) to afford N-cyclopentyl-4-((2R,3S)-1-(2-fluoro-6-methylbenzoyl)-3-((4-methyl-3-(trifluoromethyl)phenyl)-carbamoyl)piperidin-2-yl)benzenaminium 4-methylbenzenesulfonate as off-white crystals, with a recovery yield of 297.3 g (87%). $^1$H NMR (400 MHz, DMSO-d$_6$) δ 10.45 (s, 1H), 7.89-7.85 (m, 1H), 7.65-7.53 (m, 1H), 7.53-7.41 (m, 4H), 7.38-7.27 (m, 2H), 7.20-7.00 (m, 5H), 6.42-6.36 (m, 1H), 5.10-4.35 (br, 2H), 3.85-3.70 (m, 1H), 3.20-3.01 (m, 3H), 2.40-2.30 (m, 4H), 2.27 (s, 3H), 2.20-1.40 (m, 15H); (65° C.) δ 10.23 (d, J=8.4 Hz, 1H), 7.85 (dd, J=8.8, 2.0 Hz, 1H), 7.68-7.56 (m, 1H), 7.49 (J=8.0 Hz, 2H), 7.44-6.89 (m, 11H), 6.43-6.37 (m, 1H), 3.81-3.73 (m, 1H), 3.26-2.99 (m, 3H), 2.40-2.30 (m, 5H), 2.28 (s, 3H), 1.98-1.40 (m, 14H). MS: (ES) m/z calculated for $C_{33}H_{36}F_4N_3O_2$ [M+H]$^+$ 582.3, found 582.2. A plot of the XRPD is shown in FIG. 8, and Table 4, below, summarizes significant peaks observed in the XRPD plot. HPLC (both achiral analytical and chiral): >99%. Elemental Analysis consistent with formula of $C_{40}H_{43}F_4N_3O_5S$, KF: 0.85%.

TABLE 4

Significant Peaks in tosylate salt Form I of Compound 1
Significant Peaks
2-theta (deg)

| | |
|---|---|
| 6.60 | 18.34 |
| 7.58 | 18.75 |
| 9.28 | 19.68 |
| 9.62 | 21.00 |
| 10.36 | 21.56 |
| 10.76 | 22.08 |
| 11.00 | 23.54 |
| 13.12 | 23.79 |
| 14.38 | 25.06 |
| 15.32 | 26.35 |
| 15.98 | 27.82 |
| 16.54 | 28.60 |
| 17.92 | |

Figure 9:
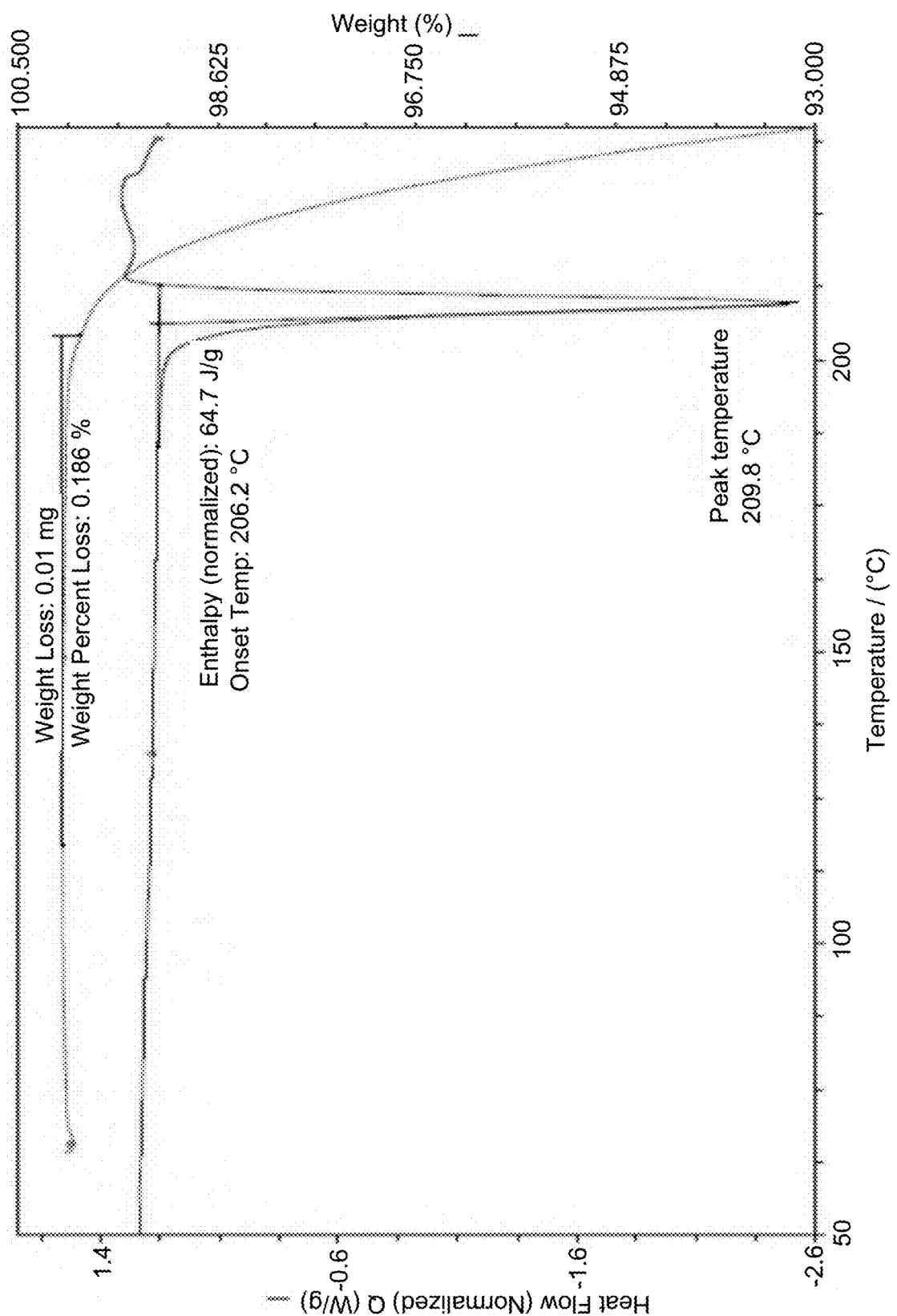
FIG. 9 shows the differential scanning calorimetry (DSC) thermogram as well as the thermal gravimetric analysis (TGA) of tosylate salt Form I of Compound 1.

Differential scanning calorimetry (DSC) was performed as described in Example 1. DSC analysis determined that the melting point (onset) is about 206.2° C. (DSC). The DSC plot also exhibits an endothermic peak at around 209.8° C. A plot of the DSC thermogram is shown in FIG. 9 (lower trace).

TGA was performed as described in Example 1. The TGA analysis determined that tosylate salt Form I of Compound 1 exhibits about a 0.19% weight loss upon heating to around 204.2° C. A plot of the TGA thermogram is shown in FIG. 9 (upper trace).

Figure 10:
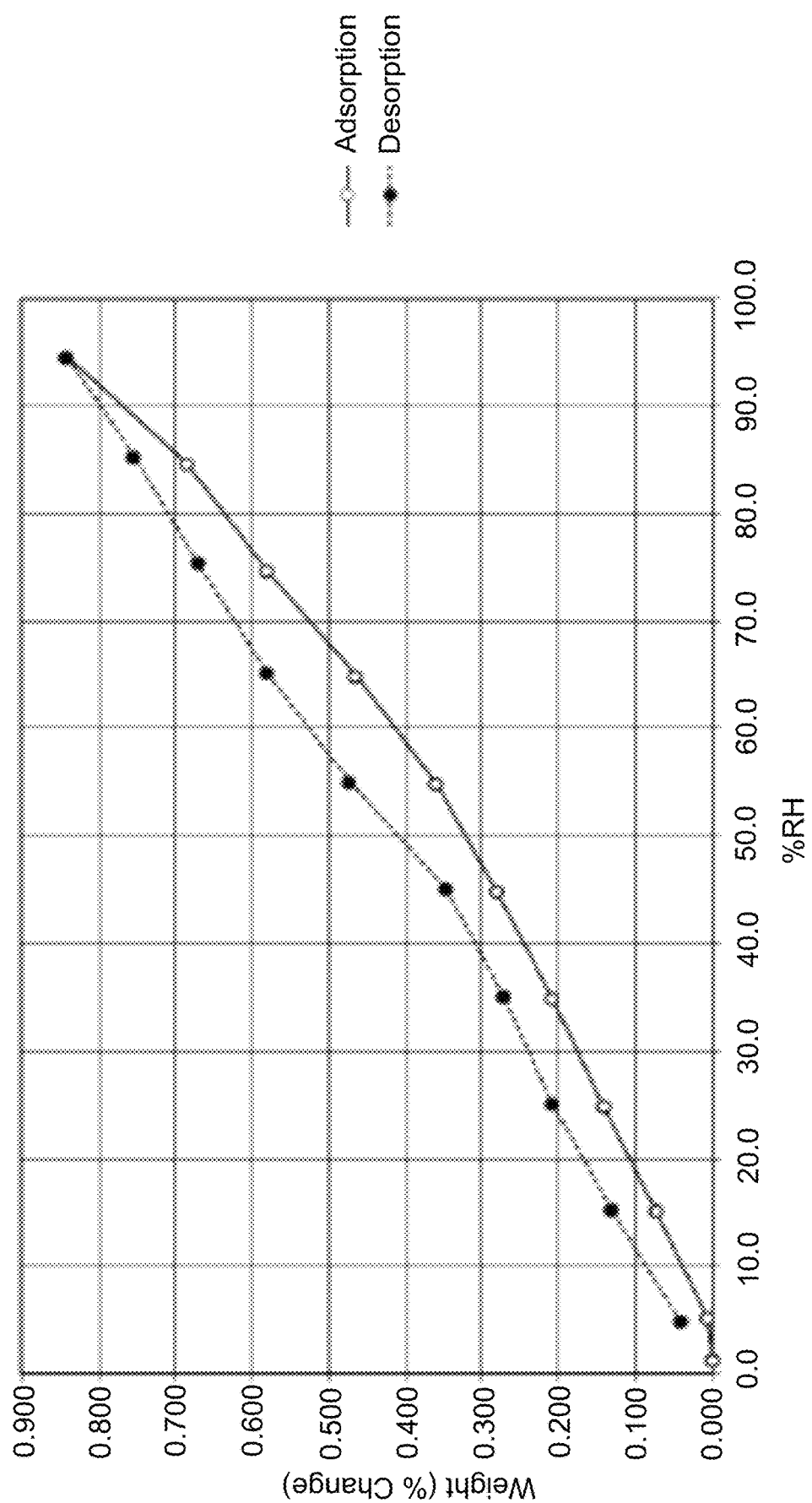
FIG. 10 shows dynamic vapor sorption (DVS) plot of tosylate salt Form I of Compound 1.

The hygroscopicity and physical stability of the collected crystals was measured using dynamic vapor sorption (DVS) as described in Example 1. A plot of the DVS measurement is shown in FIG. 10. A 0.83% weight change from 5% to 95% relative humidity (RH) was measured. A weight change of about 0.58% from about 0% relative humidity (RH) to about 75% relative humidity was also measured. No change in XRPD was observed before and after the DVS measurement (data not shown).

Figure 11:
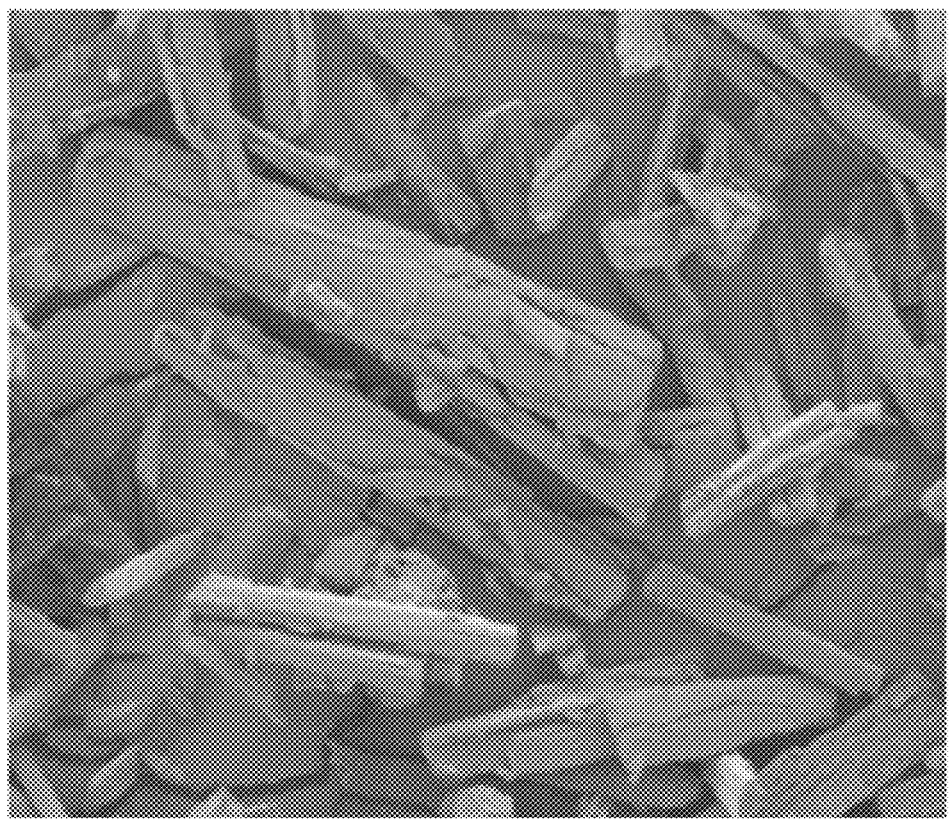
FIG. 11 shows a representative scanning electron microscopy (SEM) image of tosylate salt Form I of Compound 1. The magnification shown is 1,000×.

The collected crystals were observed using a scanning electron microscope (SEM) as described in Example 1. A representative image of the crystals is shown in FIG. 11. When observed under magnification the crystals were blades, rods, or equants ranging in size from ~1 to 500 μm.

The collected crystals were observed using polarized light microscopy (PLM) as described in Example 1. Representative images of the crystals are shown in FIG. 12. When observed under magnification the crystals were acicular, blades, and anhedral ranging in size from ~2.5 to 440 μm.

The stability of the collected crystals were tested by storing the crystals at 40° C. and 75% relative humidity for 45 days. These conditions did not result in any appreciable decomposition as shown by HPLC, LCMS and NMR analysis (data not shown). Heating at 55° C. in a vacuum oven for 24 h or 75° C. for 1 week (open to air) did not result in any appreciable decomposition as shown by HPLC, LCMS and NMR analysis (data now shown). The physical forms of both samples remained the same based on XRPD take before and after the tests (data not shown).

Example 4: A Napadisylate Salt of Compound 1 (Form I)

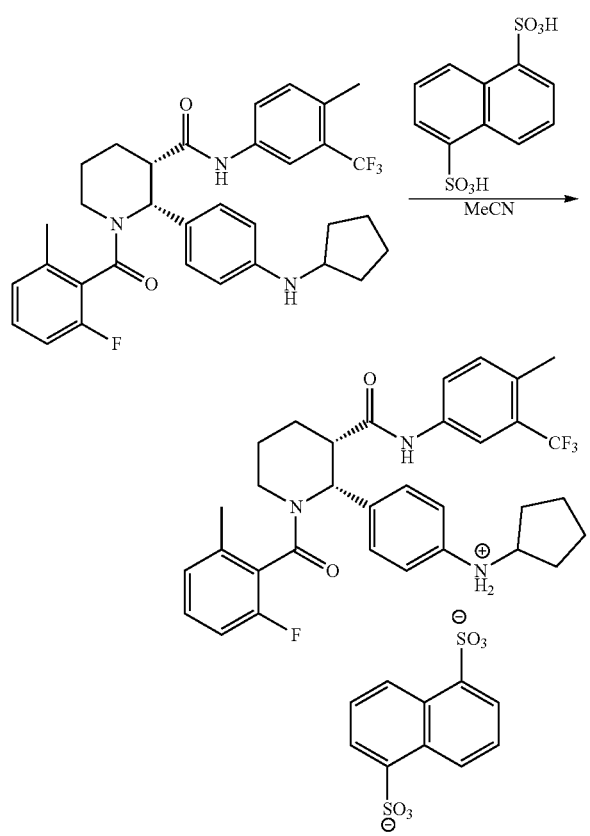

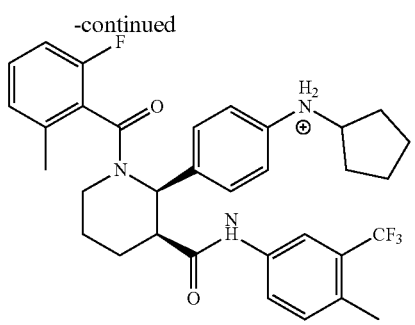

Figure 13:
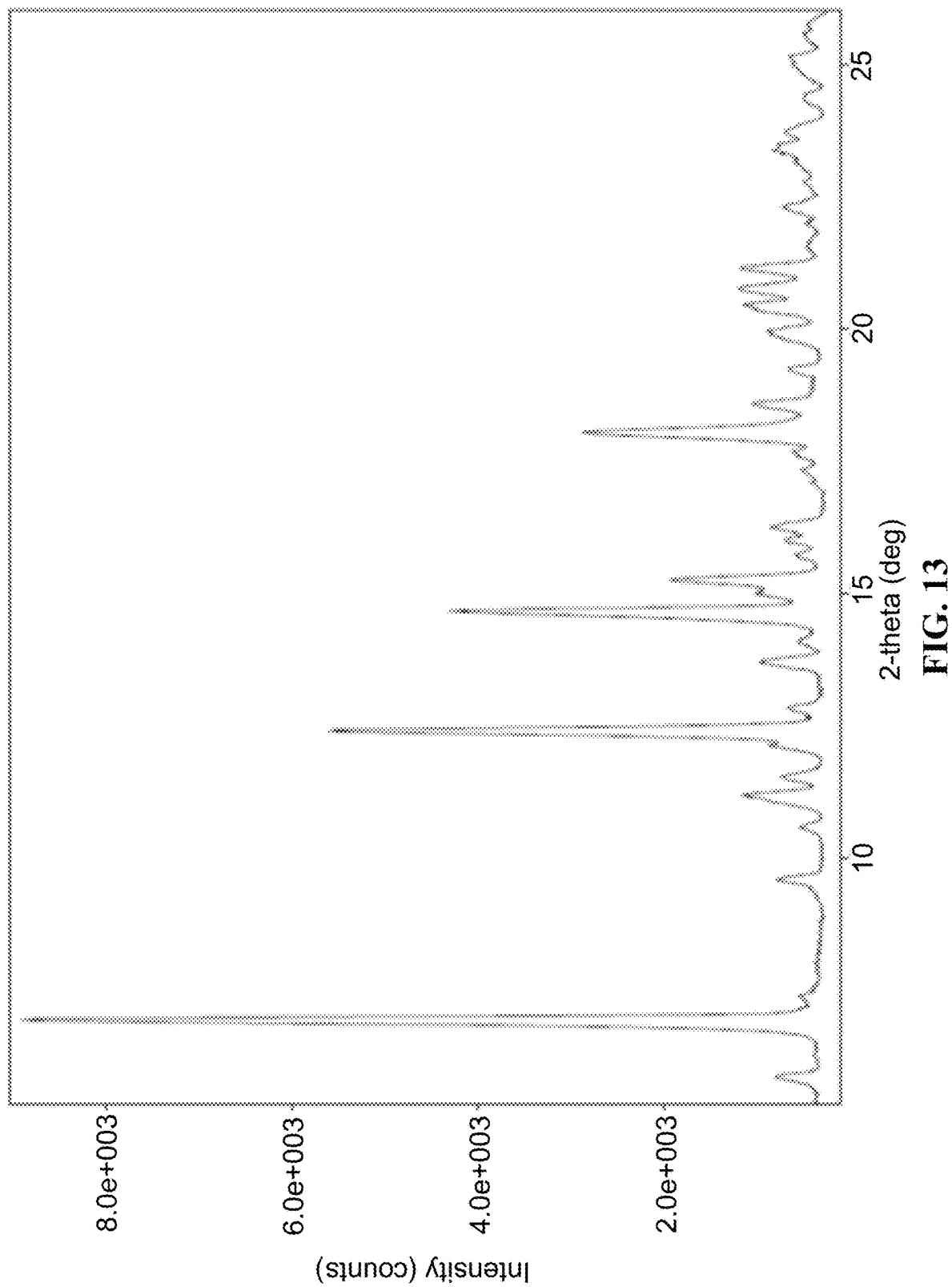
FIG. 13 shows X-ray powder diffraction (XRPD) patterns of napadisylate salt Form I of Compound 1.

A 5-L three neck flask equipped with an overhead stirrer was charged with (2R,3S)-2-(4-(cyclopentylamino)phenyl)-1-(2-fluoro-6-methylbenzoyl)-N-(4-methyl-3-(trifluoromethyl)phenyl)piperidine-3-carboxamide ((Compound 1, 261.2 g, 450 mmol) and MeCN (2 L, ~8 vol). The resulting mixture was stirred and heated to 75° C. (internal temperature) for 20 min to form a clear solution, cooled to 70° C. (inner temperature) and filtered through polyethylene frit filter and rinsed with MeCN (200 mL). To this solution was slowly added a pre-filtered solution of naphthalene-1,5-disulfonic acid hydrate (89.2 g, 247.5 mmol (based on 4 hydrate (KF)), 0.6 eq) in DI $H_2O$ (90 mL, 1 vol) and MeCN (270 mL) over 25 min (the reaction mixture became cloudy after ⅔ of the acid was added, at this point seeded with napadisylate crystals of Compound 1 (~100 mg)) and rinsed with 3% $H_2O$ in MeCN (50 mL) (inner temperature dropped to 65° C.). The resulting mixture was stirred at 70° C. for 40 min and the large chunk of solid formed was broken up manually by specula. The resulting mixture was slowly cooled to RT and stirred for 3 h. The solid was collected by filtration, washed with 3% $H_2O$ in MeCN (250 mL×2), MeCN (250 mL×2), air-dried (1 h) and then dried in an oven under vacuum at 50° C. overnight (30 h) to afford N-cyclopentyl-4-((2R,3S)-1-(2-fluoro-6-methylbenzoyl)-3-((4-methyl-3-(trifluoromethyl)phenyl)-carbamoyl)piperidin-2-yl)benzenaminium naphthalene-1,5-disulfonate as off-white crystals, with a recovery yield of 299.4 g (91%). $^1$H NMR (400 MHz, DMSO-$d_6$) (RT) δ 10.44 (s, 1H), 8.83 (d, J=8.8 Hz 1H), 7.95-7.80 (m, 2H), 7.65-7.28 (m, 6H), 7.19-7.00 (m, 3H), 6.43-6.34 (m, 1H), 4.55-3.95 (br, 2H), 3.85-3.68 (m, 1H), 3.25-2.99 (m, 3H), 2.38-2.00 (m, 5H), 1.90-1.40 (m, 14H); (65° C.) δ 10.21 (d, J=8.8 Hz, 1H), 8.90 (d, J=8.4 Hz, 1H), 7.93 (d, J=6.8 Hz, 1H), 7.89-7.82 (m, 1H), 7.68-7.58 (m, 1H), 7.46-7.20 (m, 5H), 7.16-6.70 (m, 4H), 6.44-6.35 (m, 1H), 5.80-5.20 (br, 1H), 3.80-3.64 (m, 1H), 3.22-2.98 (m, 3H), 2.40-2.00 (m, 6H), 1.96-1.40 (m, 13H). MS: (ES) m/z calculated for $C_{33}H_{36}F_4N_3O_2$ [M+H]$^+$ 582.3, found 582.2. A plot of the XRPD is shown in FIG. 13, and Table 5, below, summarizes significant peaks observed in the XRPD plot. HPLC: >99%. Elemental Analysis consistent with formular of $C_{38}H_{39}F_4N_3O_5S$; KF: 1.63%.

TABLE 5

Significant Peaks in napadisylate salt Form I of Compound 1
Significant Peaks
2-theta (deg)

| | |
|---|---|
| 5.86 | 18.04 |
| 6.94 | 18.58 |
| 9.58 | 19.24 |
| 10.58 | 19.95 |
| 11.18 | 20.46 |
| 11.54 | 20.76 |

TABLE 5-continued

Significant Peaks in napadisylate salt Form I of Compound 1

| Significant Peaks 2-theta (deg) | |
|---|---|
| 12.40 | 21.14 |
| 12.84 | 22.30 |
| 13.68 | 23.36 |
| 14.06 | 23.72 |
| 14.66 | 24.30 |
| 14.98 | 25.14 |
| 15.24 | 25.58 |
| 15.72 | 26.33 |
| 15.98 | 27.14 |
| 16.25 | 28.14 |
| 17.32 | 28.74 |
| 17.68 | 29.28 |

Figure 14:
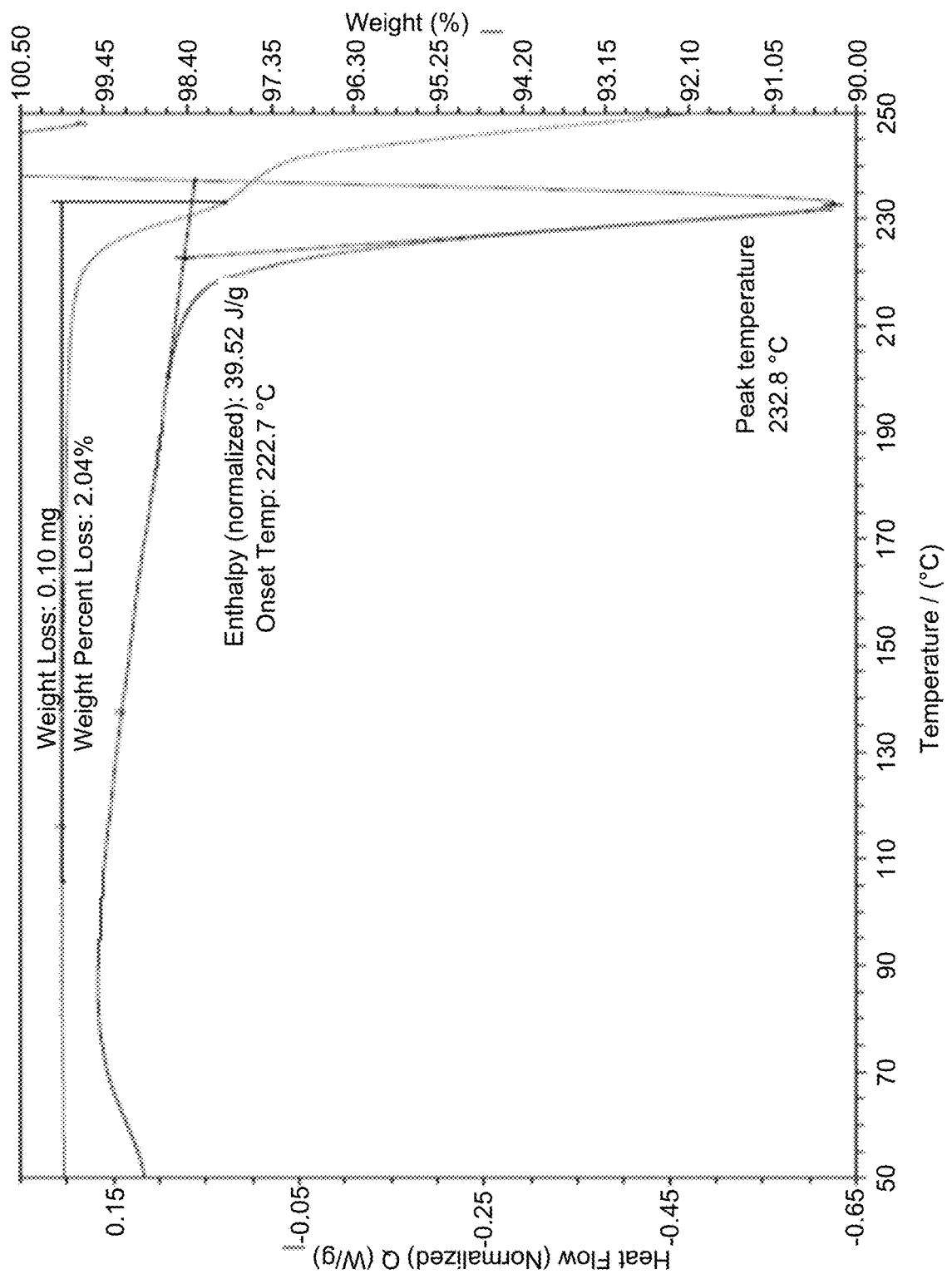
FIG. 14 shows the differential scanning calorimetry (DSC) thermogram as well as the thermal gravimetric analysis (TGA) of napadisylate salt Form I of Compound 1.

Differential scanning calorimetry (DSC) was performed as described in Example 1. DSC analysis determined that the onset and peak melting temperatures of the endothermic peak were 222.7° C. and 232.8° C., respectively. A plot of the DSC thermogram is shown in FIG. 14 (lower trace).

TGA was performed as described in Example 1. The TGA analysis determined that napadisylate salt Form I of Compound 1 exhibits about a 2.0% weight loss upon heating to around 233.1° C. A plot of the TGA thermogram is shown in FIG. 14 (upper trace).

Figure 15:
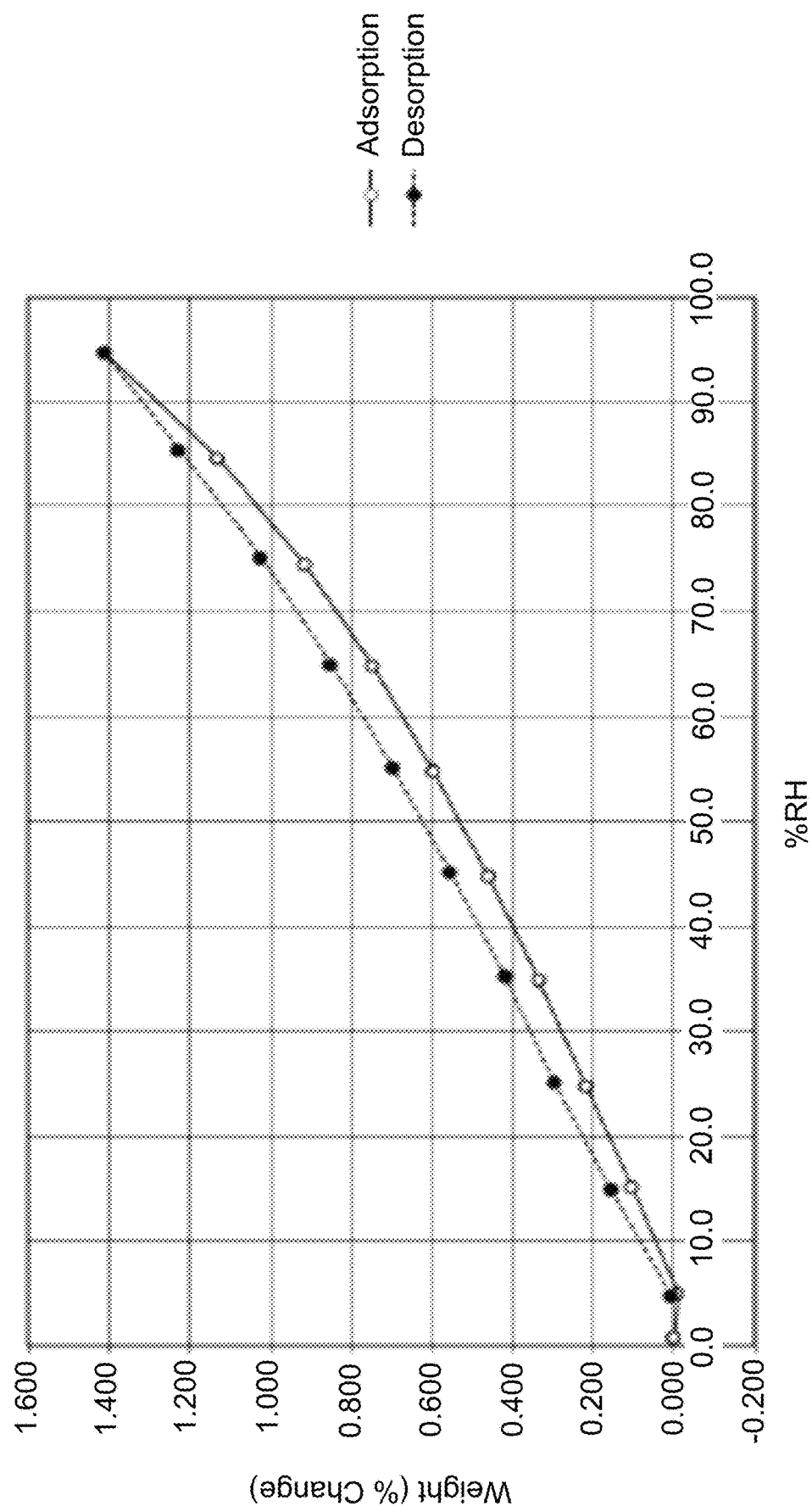
FIG. 15 shows dynamic vapor sorption (DVS) plot of napadisylate salt Form I of Compound 1.

The hygroscopicity and physical stability of the collected crystals was measured using dynamic vapor sorption (DVS) as described in Example 1. A plot of the DVS measurement is shown in FIG. 15. A 1.42% weight change from 5% to 95% relative humidity (RH) was measured. A weight change of about 0.6% from about 0% relative humidity (RH) to about 55% relative humidity was also measured. No change in XRPD was observed before and after the DVS measurement (data not shown).

Figure 16:
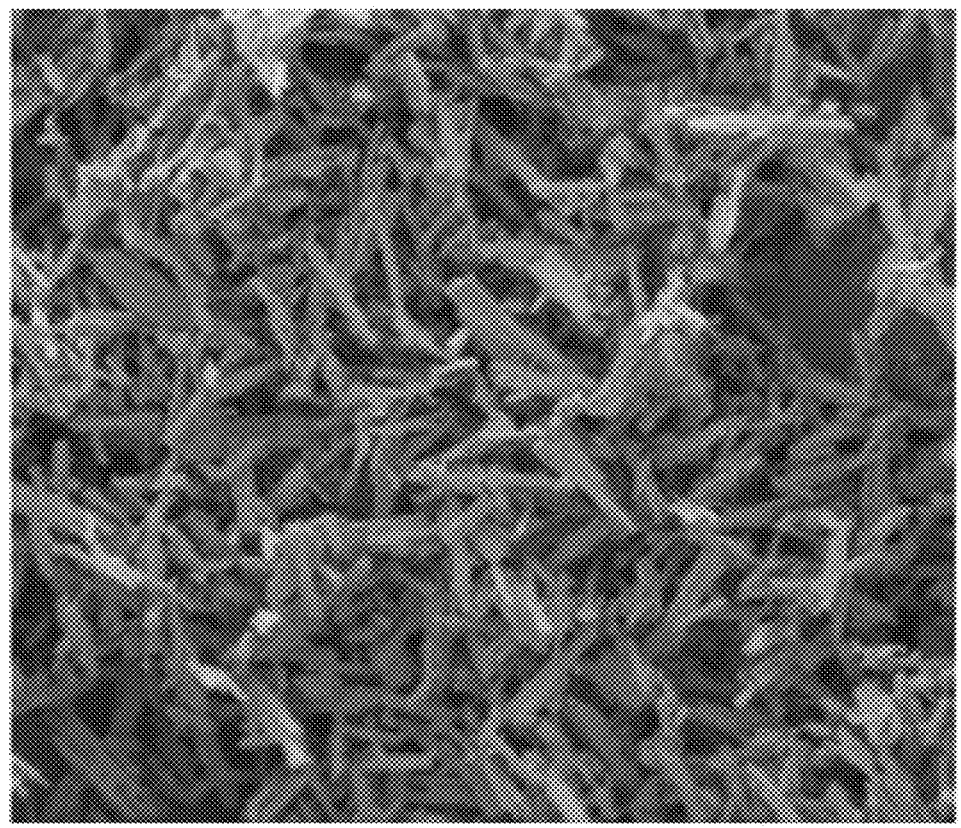
FIG. 16 shows a representative scanning electron microscopy (SEM) image of napadisylate salt Form I of Compound 1. The magnification shown is 2,500×.

The collected crystals were observed using a scanning electron microscope (SEM) as described in Example 1. A representative image of the crystals is shown in FIG. 16. When observed under magnification the crystals were blades, rods, and equants ranging in size from 1 to 150 µm.

The collected crystals were observed using polarized light microscopy (PLM) as described in Example 1. Representative images of the crystals are shown in FIG. 17. When observed under magnification the crystals were a circular, blade, or anhedral ranging in size from ~1.3 to 75 µm.

The stability of the collected crystals were tested by storing the crystals at 40° C. and 75% relative humidity for 45 days. These conditions did not result in any appreciable decomposition as shown by HPLC, LCMS and NMR analysis (data not shown). Heating at 55° C. in a vacuum oven for 24 h or 75° C. for 1 week (open to air) did not result in any appreciable decomposition as shown by HPLC, LCMS and NMR analysis (data now shown). The physical forms of both samples remained the same based on XRPD take before and after the tests (data not shown).

Example 5: A Napsylate Salt of Compound 1 (Form I)

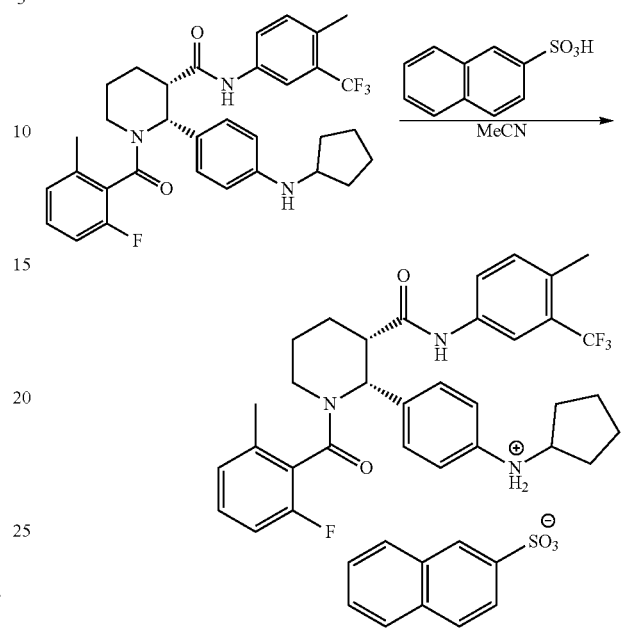

Figure 18:
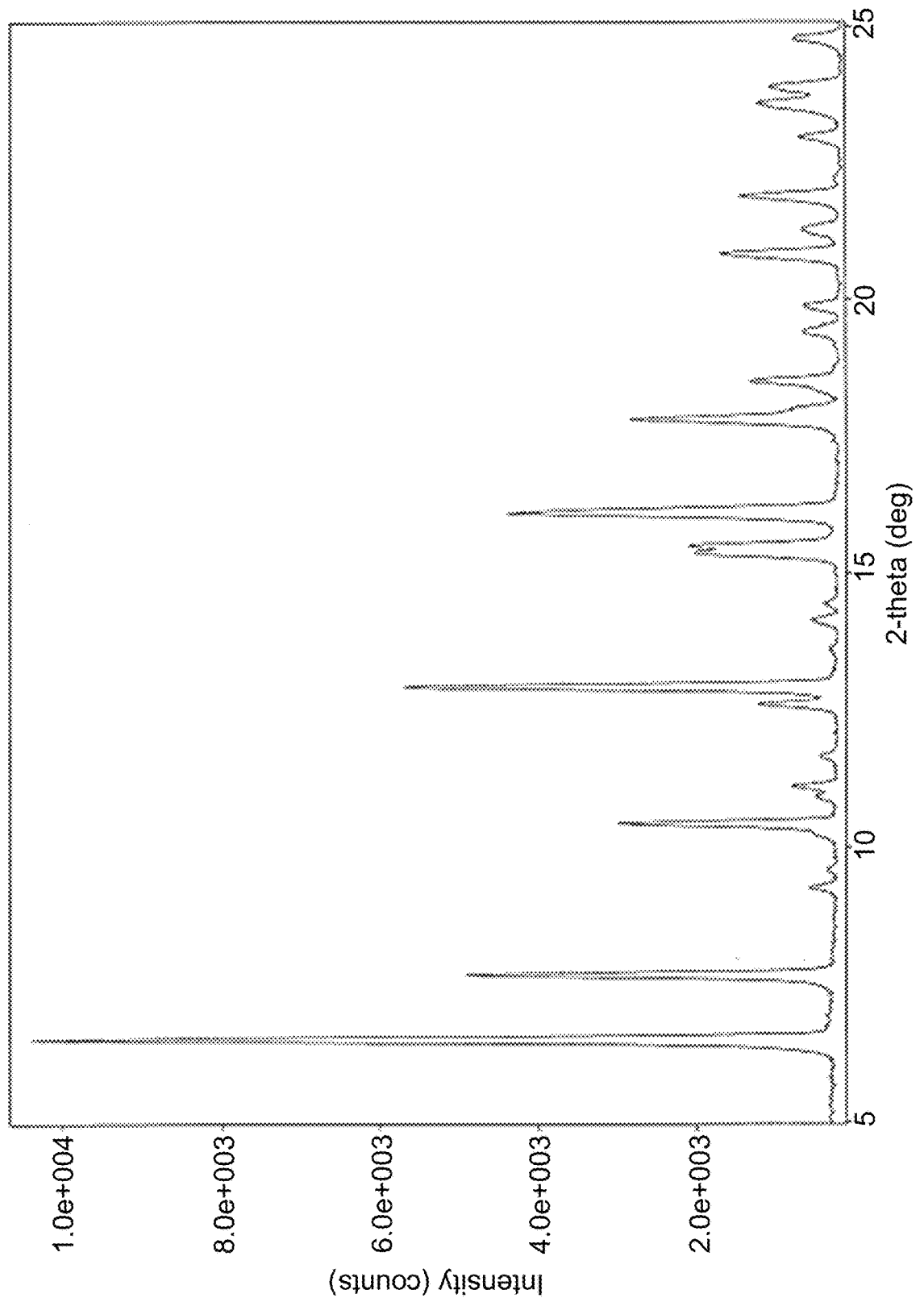
FIG. 18 shows X-ray powder diffraction (XRPD) patterns of napsylate salt Form I of Compound 1.

A 5-L three neck flask equipped with an overhead stirrer was charged with (2R,3S)-2-(4-(cyclopentylamino)phenyl)-1-(2-fluoro-6-methylbenzoyl)-N-(4-methyl-3-(trifluoromethyl)phenyl)piperidine-3-carboxamide (Compound 1, 263.3 g, 452.7 mmol) and MeCN (2 L, 8 vol). The resulting mixture was stirred and heated to 75° C. (inner temperature) for 15 min to form a clear solution, filtered through polyethylene frit filter and rinsed with MeCN (200 mL). To this solution at 70° C. (internal temperature) was added slowly a pre-filtered solution of 2-naphthalenesulfonic acid hydrate (108 g, 466.2 mmol (based on 1.3 hydrate, KF), 1.03 eq) in deionized $H_2O$ (54 mL, 0.5 vol) and MeCN (300 mL) over 25 min and rinsed with MeCN (100 mL) (internal temperature dopped to 64° C.). The resulting solution was stirred at 65° C. for 40 min. The resulting mixture was slowly cooled to RT and stirred over 3 h. The solid was collected by filtration, washed with MeCN (250 mL×2), air-dried (1 h) and then dried in an oven under vacuum at 50° C. overnight (24 h) to afford N-cyclopentyl-4-((2R,3S)-1-(2-fluoro-6-methylbenzoyl)-3-((4-methyl-3-(trifluoromethyl)phenyl)-carbamoyl)piperidin-2-yl)benzenaminium naphthalene-2-sulfonate as off-white crystals, with a recovery yield of 330.3 g (92%). $^1$H NMR (400 MHz, DMSO-$d_6$) (RT) δ 10.44 (s, 1H), 8.12 (s, 1H), 8.00-7.80 (m, 4H), 7.70-7.28 (m, 8H), 7.19-7.00 (m, 3H), 6.43-6.34 (m, 1H), 4.80-4.10 (br, 2H), 3.70-3.68 (m, 1H), 3.40-2.99 (m, 3H), 2.38-2.00 (m, 5H), 1.90-1.40 (m, 14H); (65° C.) δ 10.21 (d, J=8.8 Hz, 1H), 8.13 (s, 1H), 7.99-7.78 (m, 4H), 7.75-7.20 (m, 8H), 7.18-6.64 (m, 4H), 6.42-6.36 (m, 1H), 5.80-5.20 (br, 1H), 3.25-2.98 (m, 3H), 2.40-2.00 (m, 6H), 1.96-1.40 (m, 13H). MS: (ES) m/z calculated for $C_{33}H_{36}F_4N_3O_2$ [M+H]$^+$ 582.3, found 582.2. A plot of the XRPD is shown in FIG. 18, and Table 6, below, summarizes significant peaks observed in the XRPD plot. HPLC (both achiral analytical and chiral): >99%. Elemental Analysis consistent with formular of $C_{43}H_{43}F_4N_3O_5S$; KF: 0.79%.

TABLE 6

Significant Peaks in napsylate salt Form I of Compound 1
Significant Peaks
2-theta (deg)

| | |
|---|---|
| 6.50 | 18.52 |
| 7.68 | 19.42 |
| 9.28 | 19.90 |
| 10.44 | 20.84 |
| 11.10 | 21.28 |
| 12.62 | 21.92 |
| 12.92 | 23.00 |
| 14.18 | 23.56 |
| 14.46 | 23.90 |
| 15.40 | 24.78 |
| 15.50 | 25.30 |
| 16.11 | 27.40 |
| 17.84 | 28.40 |

Figure 19:
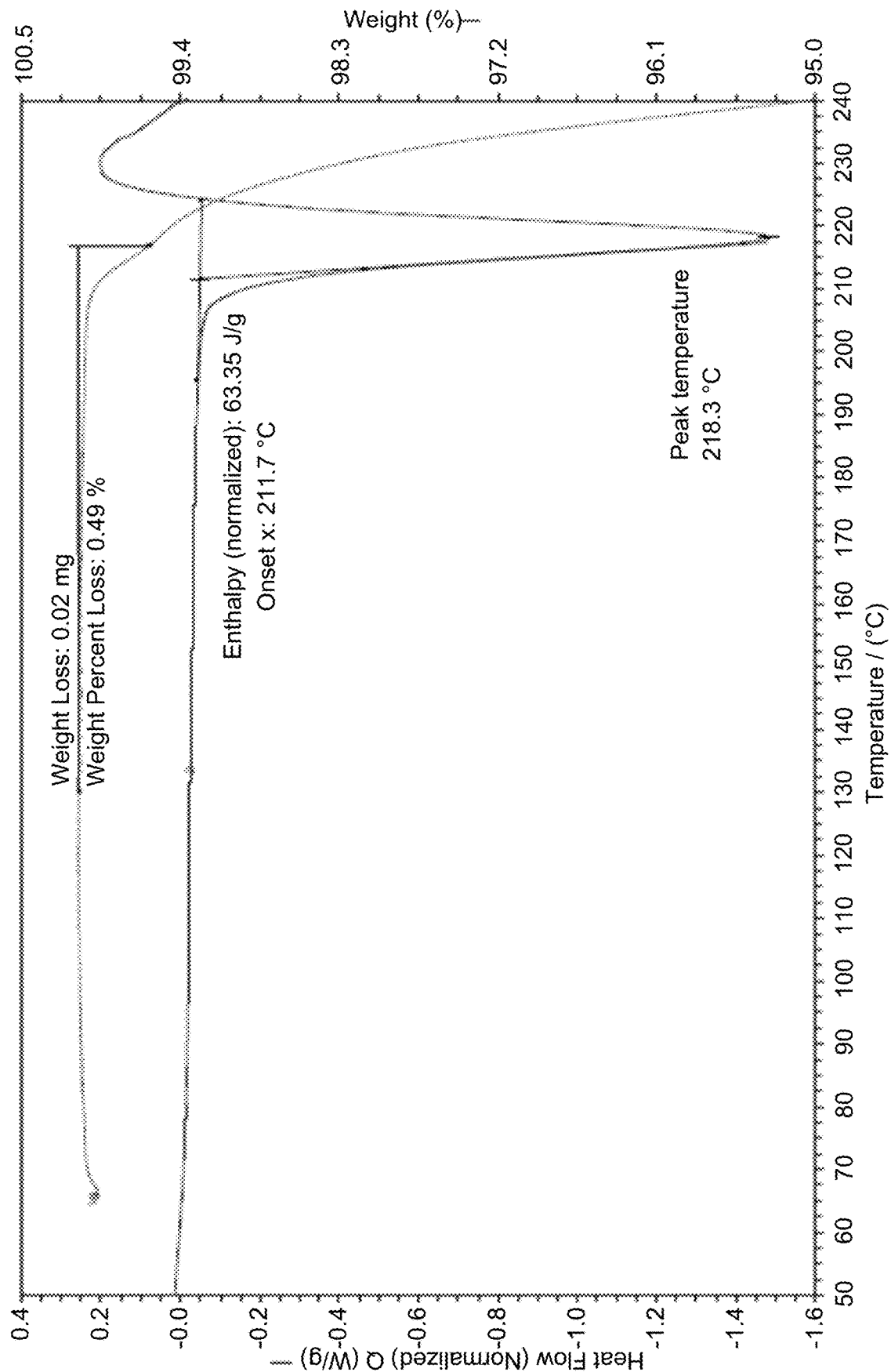
FIG. 19 shows the differential scanning calorimetry (DSC) thermogram as well as the thermal gravimetric analysis (TGA) of napsylate salt Form I of Compound 1.

Differential scanning calorimetry (DSC) was performed as described in Example 1. DSC analysis determined that the melting point (onset) is about 211.7° C. (DSC). The DSC plot also exhibits an endothermic peak at around 218.3° C. A plot of the DSC thermogram is shown in FIG. 19 (lower trace).

TGA was performed as described in Example 1. The TGA analysis determined that napsylate salt Form I of Compound 1 exhibits about a 0.49% weight loss upon heating to around 217.0° C. A plot of the TGA thermogram is shown in FIG. 19 (upper trace).

Figure 20:
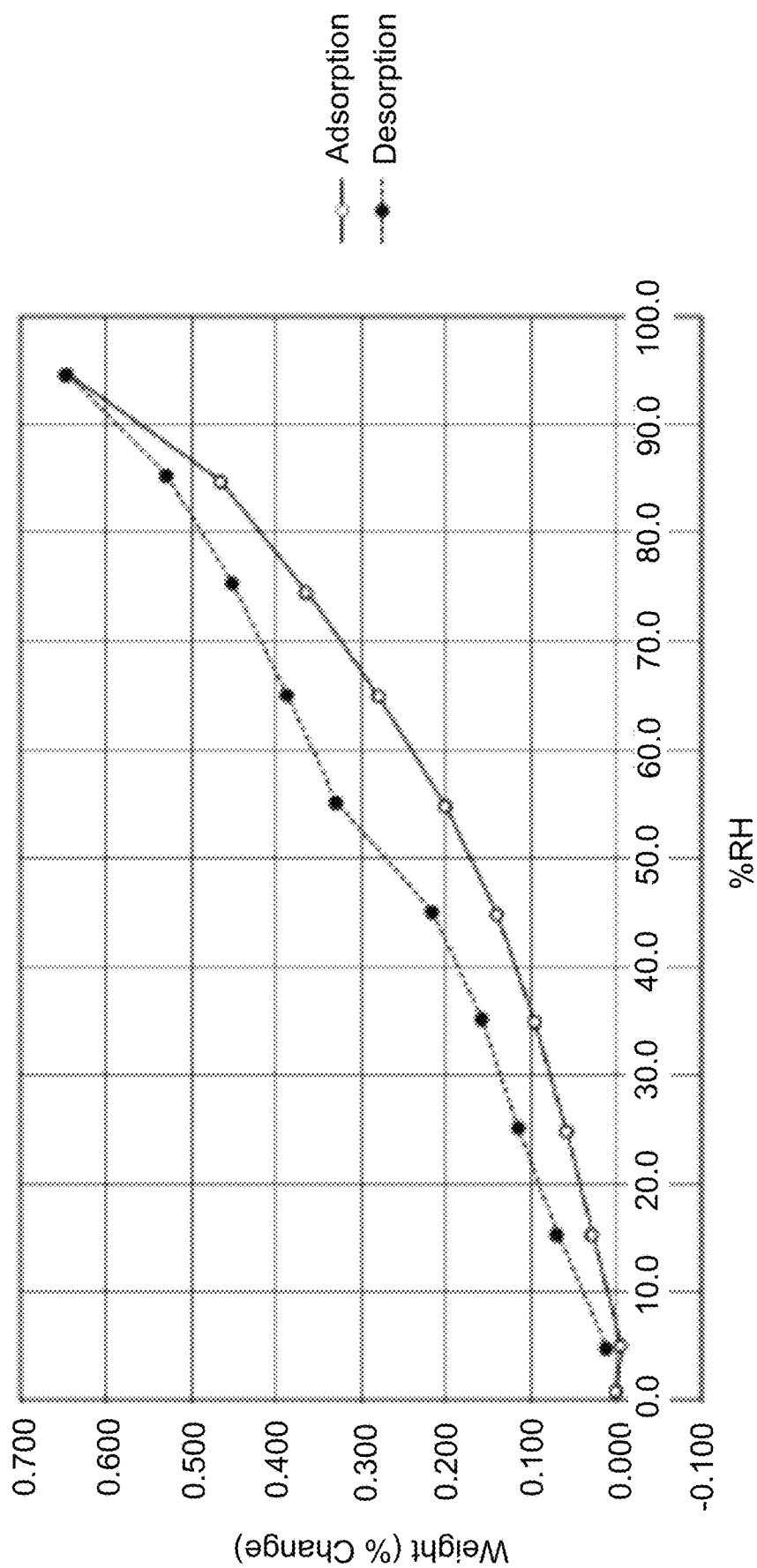
FIG. 20 shows dynamic vapor sorption (DVS) plot of napsylate salt Form I of Compound 1.

The hygroscopicity and physical stability of the collected crystals was measured using dynamic vapor sorption (DVS) as described in Example 1. A plot of the DVS measurement is shown in FIG. 20. A 0.65% weight change from 5% to 95% relative humidity (RH) was measured. A weight change of about 0.2% from about 0% relative humidity (RH) to about 55% relative humidity was also measured. No change in XRPD was observed before and after the DVS measurement (data not shown).

Figure 21:
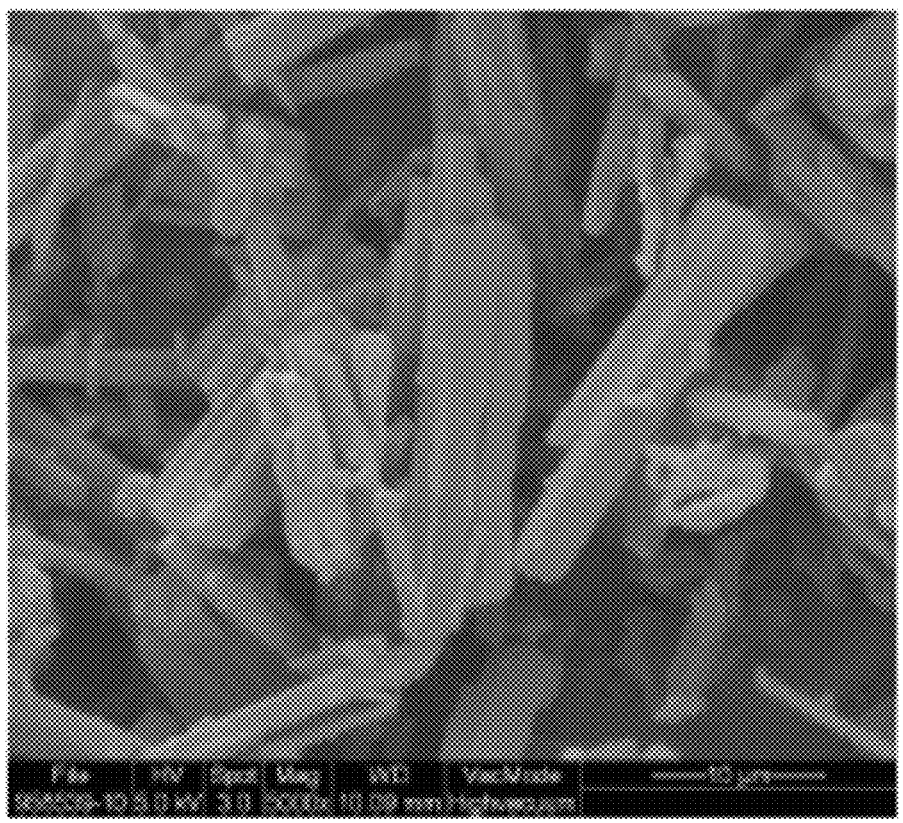
FIG. 21 shows a representative scanning electron microscopy (SEM) image of napsylate salt Form I of Compound 1. The magnification shown is 5,000×.

The collected crystals were observed using a scanning electron microscope (SEM) as described in Example 1. A representative image of the crystals is shown in FIG. 21. When observed under magnification the crystals were blades, rods, and equants ranging in size from ~1 to 150 μm.

The collected crystals were observed using polarized light microscopy (PLM) as described in Example 1. Representative images of the crystals are shown in FIG. 22. When observed under magnification the crystals were blades ranging in size from ~5 to 470 μm.

The stability of the collected crystals were tested by storing the crystals at 40° C. and 75% relative humidity for 45 days. These conditions did not result in any appreciable decomposition as shown by HPLC, LCMS and NMR analysis (data not shown). Heating at 55° C. in a vacuum oven for 24 h or 75° C. for 1 week (open to air) did not result in any appreciable decomposition as shown by HPLC, LCMS and NMR analysis (data now shown). The physical forms of both samples remained the same based on XRPD take before and after the tests (data not shown).

Example 6: A Camsylate Salt of Compound 1 (Form I)

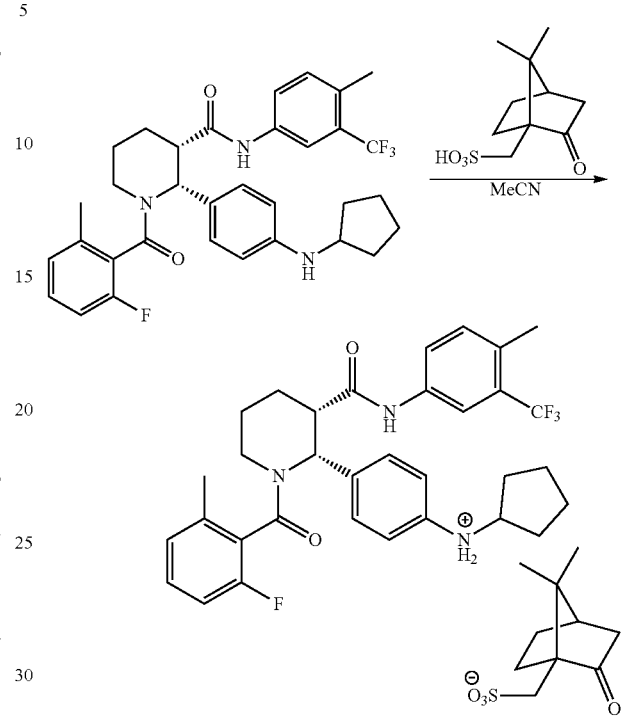

A 1-L round bottom flask equipped with a magnetic stirrer was charged with (2R,3S)-2-(4-(cyclopentylamino)phenyl)-1-(2-fluoro-6-methylbenzoyl)-N-(4-methyl-3-(trifluoromethyl)phenyl)piperidine-3-carboxamide (Compound 1, 54.5 g, 94 mmol) and MeCN (400 mL, 8 vol). The resulting mixture was stirred and heated to 75° C. (internal temperature) for 30 min to form a clear solution, cooled to 65° C. (internal temperature) and filtered through polyethylene frit filter and rinsed with MeCN (50 mL). To this solution was slowly added a pre-filtered solution of (1S)-(+)-10-camphorsulfonic acid (22.9 g, 98.06 mmol, 1.05 eq) in deionized $H_2O$ (11.5 mL, 0.5 vol) and MeCN (46 mL) over 5 min and rinsed with MeCN (23 mL) (internal temperature dopped to 60° C.). The resulting solution was cooled to 55° C., seeded with camsylate crystals of Compound 1 (~50 mg) and stirred at the same temperature for 1 h. The resulting mixture was slowly cooled to RT and stirred for 3 h. The solid was collected by filtration, washed with 2% $H_2O$ in MeCN (50 mL×2), MeCN (50 mL×2), air-dried (1 h) and then dried in an oven under vacuum at 50° C. overnight (24 h) to afford to afford N-cyclopentyl-4-((2R,3S)-1-(2-fluoro-6-methylbenzoyl)-3-((4-methyl-3-(trifluoromethyl)phenyl)-carbamoyl)piperidin-2-yl)benzenaminium (1S)-(+)-10-camphorsulfonate as off-white crystals, with a recovery yield of 69 g (90%). $^1$H NMR (400 MHz, DMSO-$d_6$) δ 10.45 (s, 1H), 7.90-7.82 (m, 1H), 7.65-7.48 (m, 3H), 7.38-7.07 (m, 6H), 6.42-6.34 (m, 1H), 5.90-5.20 (br, 1H), 3.85-3.70 (m, 1H), 3.22-3.00 (m, 3H), 2.85 (d, J=14.7 Hz, 1H), 2.71-2.58 (m, 1H), 2.40-1.98 (m, 8H), 1.94-1.40 (m, 17H), 1.31-1.18 (m, 2H), 1.02 (s, 3H), 0.71 (s, 3H); (65° C.) δ 10.22 (d, J=8.4 Hz, 1H), 7.89-7.81 (m, 1H), 7.68-7.56 (m, 1H), 7.46-7.25 (m, 4H), 7.18-6.80 (m, 5H), 6.42-6.34 (m, 1H), 3.81-3.72 (m, 1H), 3.26-2.99 (m, 3H), 2.90 (d, J=14.7 Hz, 1H), 2.75-2.62 (m, 1H), 2.48-2.00 (m, 8H), 1.94-1.40 (m, 17H), 1.35-1.20

Figure 23:
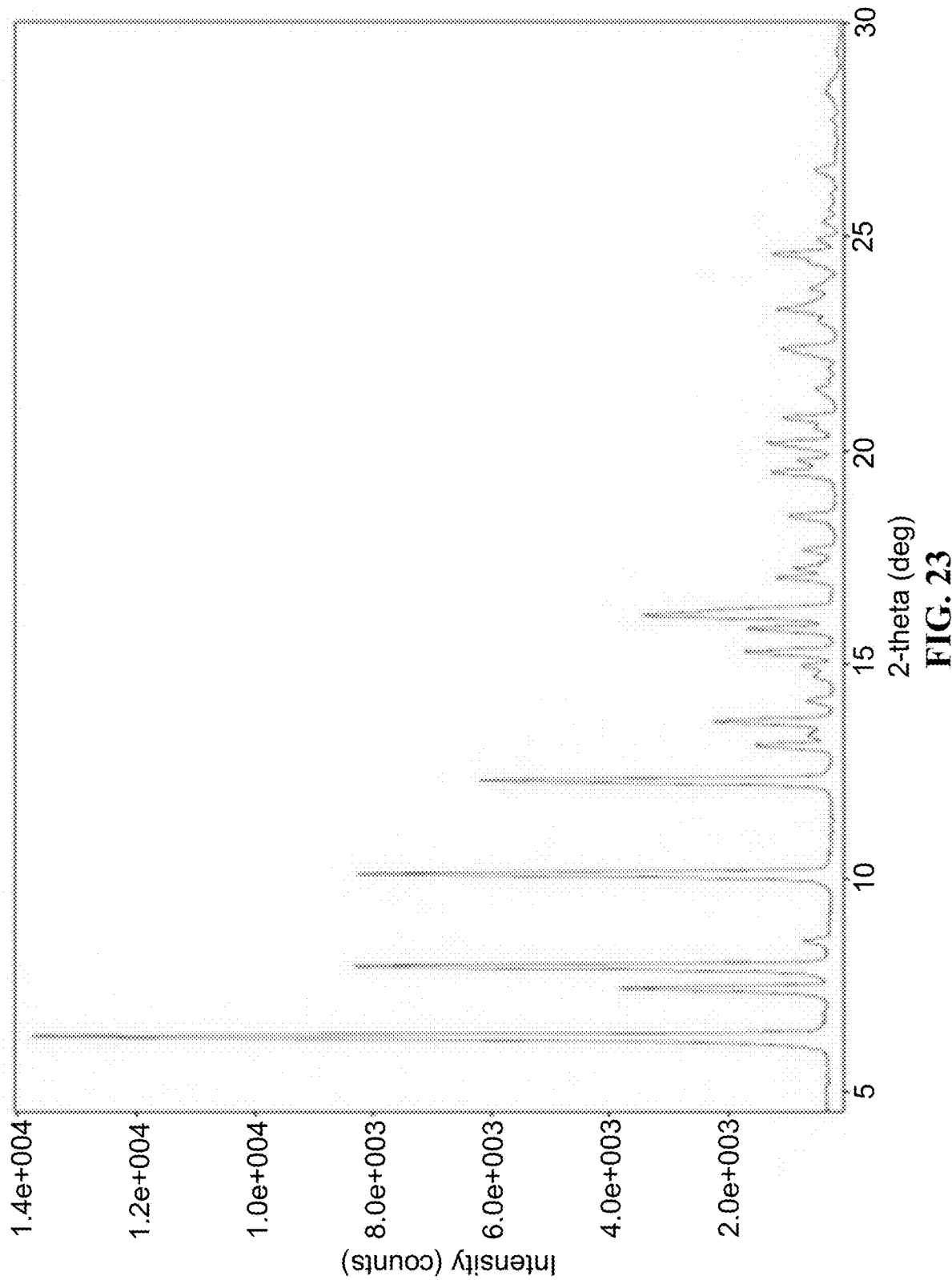
FIG. 23 shows X-ray powder diffraction (XRPD) patterns of camsylate salt Form I of Compound 1.

(m, 2H), 1.06 (s, 3H), 0.75 (s, 3H). MS: (ES) m/z calculated for $C_{33}H_{36}F_4N_3O_2$ [M+H]$^+$ 582.3, found 582.2.) (RFD: A plot of the XRPD is shown in FIG. 23, and Table 7, below, summarizes significant peaks observed in the XRPD plot. HPLC: >99%. Elemental Analysis consistent with formula of $C_{43}H_{51}F_4N_3O_6S$, KF: 1.09%.

TABLE 7

Significant Peaks in camsylate salt Form I of Compound 1
Significant Peaks
2-theta (deg)

| | |
|---|---|
| 6.26 | 17.66 |
| 7.40 | 18.45 |
| 7.92 | 19.47 |
| 8.52 | 19.74 |
| 10.08 | 20.13 |
| 12.24 | 20.51 |
| 13.08 | 20.73 |
| 13.32 | 21.36 |
| 13.66 | 22.36 |
| 14.14 | 22.98 |
| 14.20 | 23.26 |
| 14.96 | 23.76 |
| 15.26 | 24.55 |
| 15.79 | 24.90 |
| 16.10 | 25.32 |
| 17.00 | 26.52 |
| 17.20 | |

Figure 24:
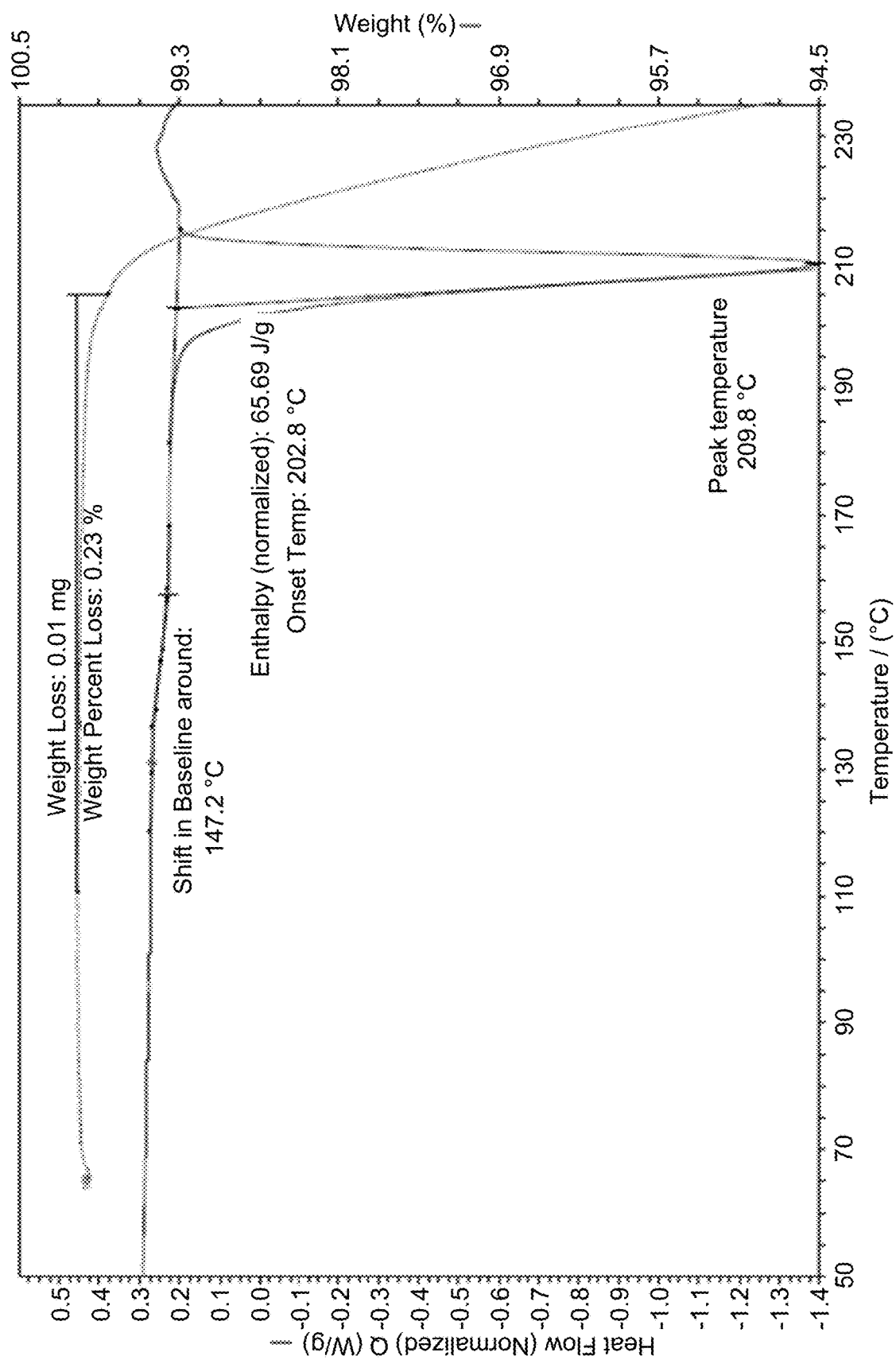
FIG. 24 shows the differential scanning calorimetry (DSC) thermogram as well as the thermal gravimetric analysis (TGA) of camsylate salt Form I of Compound 1.

Differential scanning calorimetry (DSC) was performed as described in Example 1. DSC analysis determined that the melting point (onset) is about 202.8° C. (DSC). The DSC plot also exhibits an endothermic peak at around 209.8° C. A plot of the DSC thermogram is shown in FIG. 24 (lower trace).

TGA was performed as described in Example 1. The TGA analysis determined that camsylate salt Form I of Compound 1 exhibits about a 0.23% weight loss upon heating to around 205.0° C. A plot of the TGA thermogram is shown in FIG. 24 (upper trace).

Figure 25:
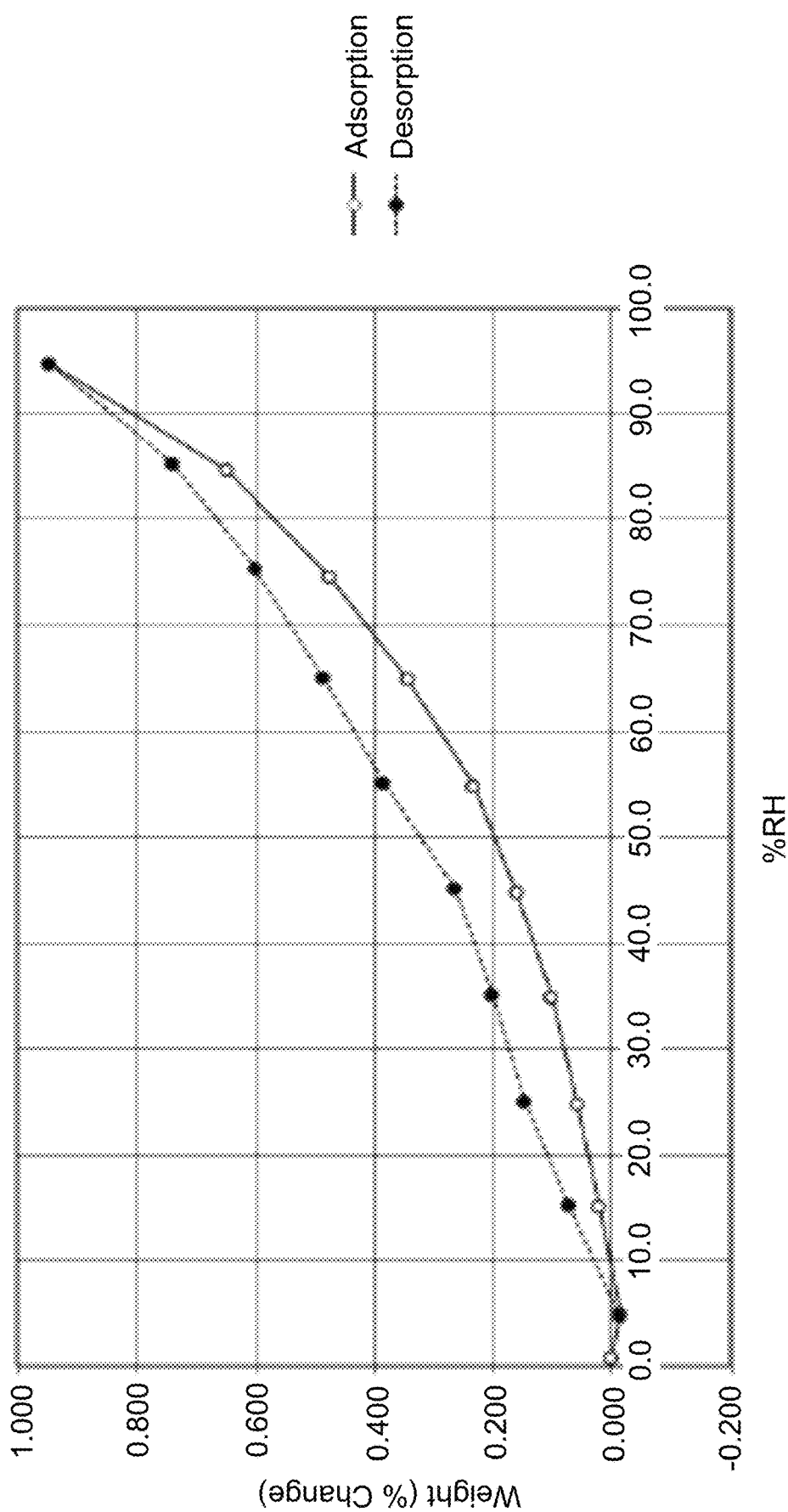
FIG. 25 shows dynamic vapor sorption (DVS) plot of camsylate salt Form I of Compound 1.

The hygroscopicity and physical stability of the collected crystals was measured using dynamic vapor sorption (DVS) as described in Example 1. A plot of the DVS measurement is shown in FIG. 25. A 0.96% weight change from 5% to 95% relative humidity (RH) was measured. A weight change of about 0.35% from about 0% relative humidity (RH) to about 65% relative humidity was also measured. No change in XRPD was observed before and after the DVS measurement (data not shown).

Figure 26:
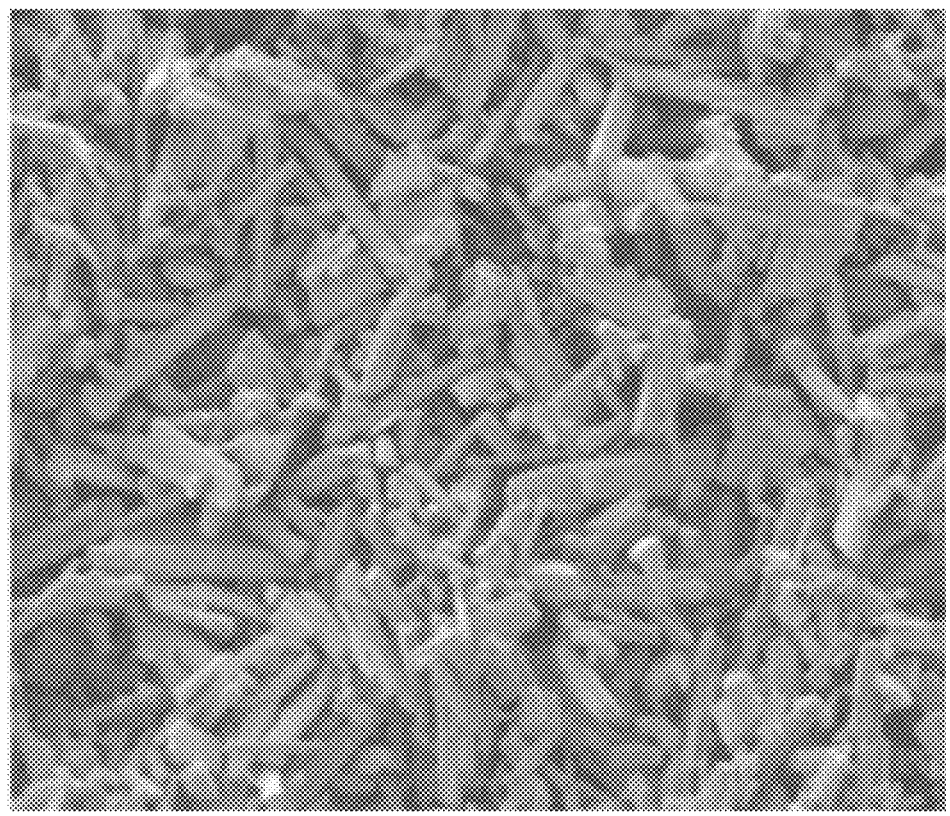
FIG. 26 shows a representative scanning electron microscopy (SEM) image of camsylate salt Form I of Compound 1. The magnification shown is 5,000×.

The collected crystals were observed using a scanning electron microscope (SEM) as described in Example 1. A representative image of the crystals is shown in FIG. 26. When observed under magnification the crystals were blunt-ended blades and rods ranging in size from ~<1 to 77 μm.

The collected crystals were observed using polarized light microscopy (PLM) as described in Example 1. Representative images of the crystals are shown in FIG. 27. When observed under magnification the crystals were soft agglomerates, acircular, blandes, and anhedral ranging in size from ~2.5 to 84 μm.

The stability of the collected crystals were tested by storing the crystals at 40° C. and 75% relative humidity for 45 days. These conditions did not result in any appreciable decomposition as shown by HPLC, LCMS and NMR analysis (data not shown). Heating at 55° C. in a vacuum oven for 24 h or 75° C. for 1 week (open to air) did not result in any appreciable decomposition as shown by HPLC, LCMS and NMR analysis (data now shown). The physical forms of both samples remained the same based on XRPD take before and after the tests (data not shown).

Example 7: An Edisylate Salt of Compound 1
(Form I)

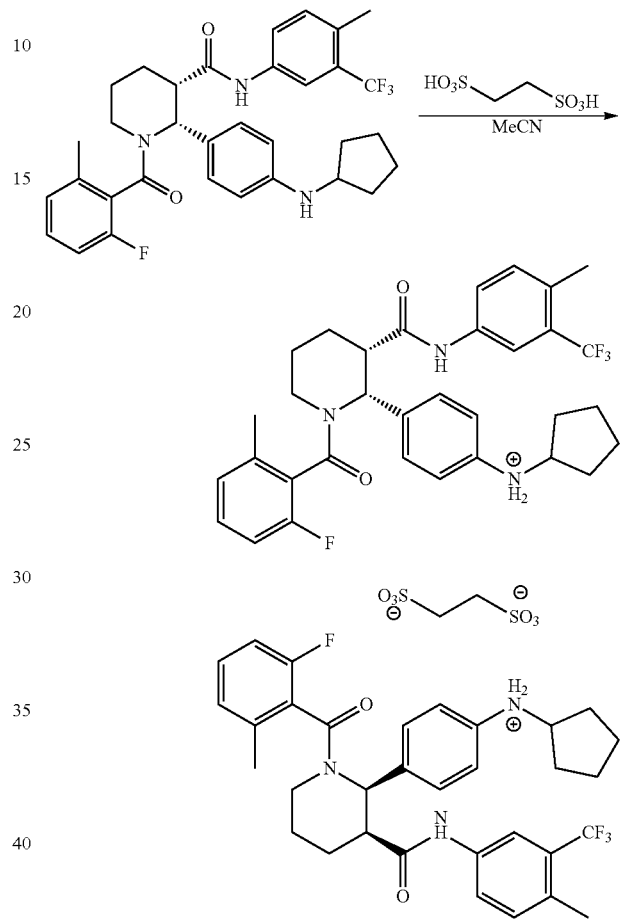

A 200 mL round bottom flask equipped with a magnetic stirrer was charged with (2R,3S)-2-(4-(cyclopentylamino)phenyl)-1-(2-fluoro-6-methylbenzoyl)-N-(4-methyl-3-(trifluoromethyl)phenyl)piperidine-3-carboxamide (CCX168 lot #D-15-012, 10 g, 17.2 mmol) and MeCN (120 mL, 12 vol). The resulting mixture was stirred and heated to 65° C. (inner temperature) for 30 min to form a clear solution. To this solution was slowly added 1,2-ethanesdisulfonic acid dihydrate (1.97 g, 8.6 mmol, 0.5 eq) portionwise. The resulting solution was stirred at the same temperature for 30 min and then cooled to room temperature. The mixture was concentrated to dryness in vacuo and then place under high vacuum overnight.

Figure 28:
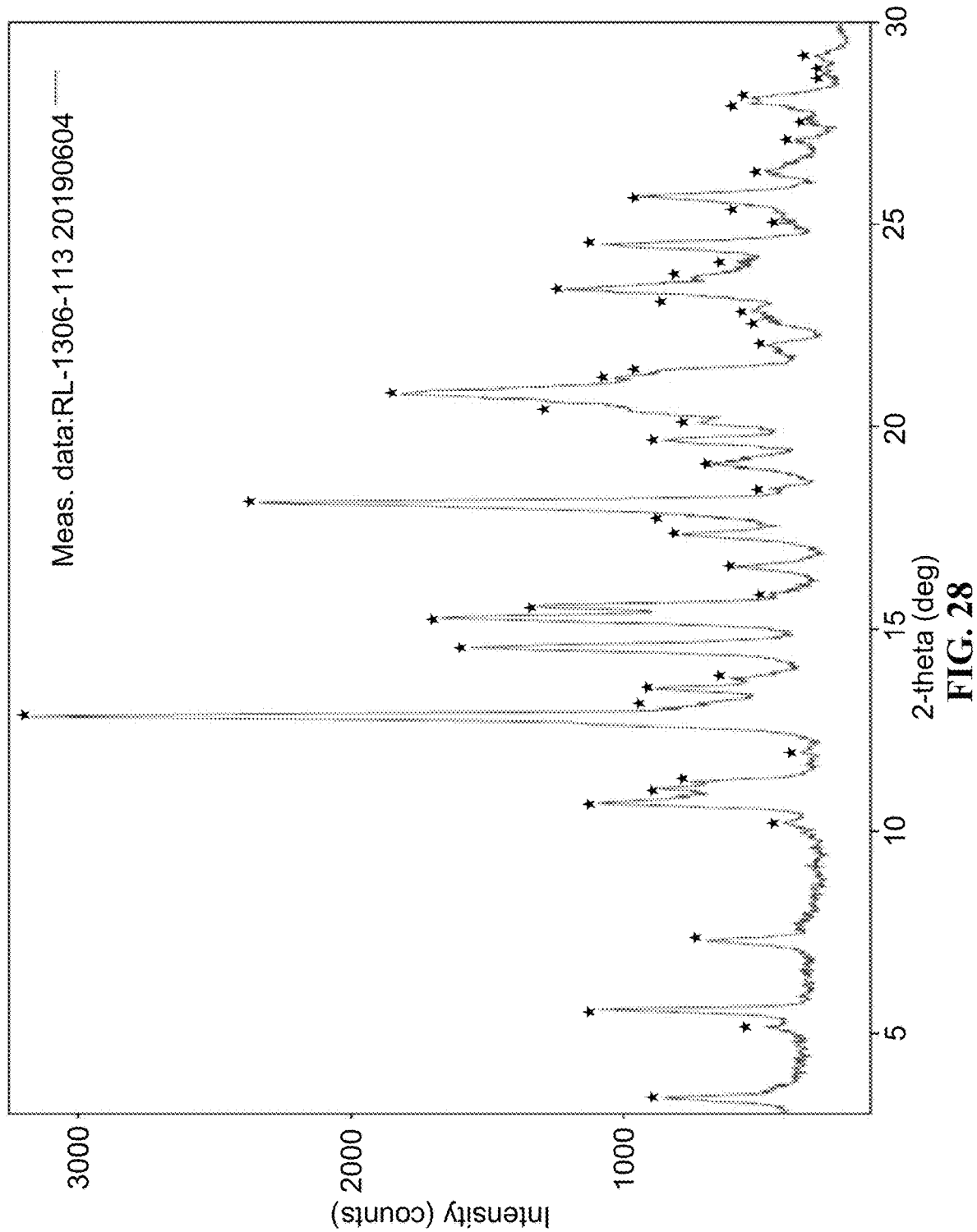
FIG. 28 shows X-ray powder diffraction (XRPD) patterns of edisylate salt Form I of Compound 1.

To the dried solid was added EtOH (100 mL, 10 V). The mixture was heated at 80° C. (inner temperature) for 1 h. The solution was slowly cooled to room temperature and stirred overnight. The solid was collected by filtration, washed with EtOH (20 mL×2) and then dried under high-vac overnight to afford N-cyclopentyl-4-((2R,3S)-1-(2-fluoro-6-methylbenzoyl)-3-((4-methyl-3-(trifluoromethyl)phenyl)carbamoyl)piperidin-2-yl)benzenaminium ethane-1,2-disulfonate as off-white crystals, with a recovery yield of 8.94 g (77%). $^1$H NMR (400 MHz, DMSO-d$_6$) δ 10.45 (s, 1H), 7.85 (dd, J=10.8, 2.2 Hz, 1H), 7.68-7.47 (m, 3H), 7.39-7.22 (m, 4H), 7.20-7.00 (m, 2H), 6.41 (dd, J=11.3, 6.2 Hz, 1H), 3.81 (m, J=6.6 Hz, 1H), 3.23-3.02 (m, 3H), 2.69 (s, 2H), 2.33 (m, 5H), 2.22-2.00 (m, 1H), 1.87 (s, 3H), 1.85-1.72 (m, 3H), 1.72-1.63 (m, 2H), 1.62-1.45 (m, 5H). MS: (ES) m/z calculated for $C_{33}H_{36}F_4N_3O_2$ $[M+H]^+$ 582.3, found 582.2. A plot of the XRPD is shown in FIG. 28, and Table 8, below, summarizes significant peaks observed in the XRPD plot. HPLC: >99%. Elemental Analysis consistent with formula of $C_{68}H_{76}F_8N_6O_{10}S_2$, KF: 1.13%.

TABLE 8

Significant Peaks in edisylate salt Form I of Compound 1
Significant Peaks
2-theta (deg)

| | |
|---|---|
| 3.42 | 20.10 |
| 5.18 | 20.38 |
| 5.60 | 20.82 |
| 7.28 | 21.20 |
| 10.21 | 21.38 |
| 10.70 | 22.02 |
| 11.06 | 22.67 |
| 11.22 | 22.88 |
| 12.84 | 23.40 |
| 13.04 | 23.69 |
| 13.51 | 24.80 |
| 13.78 | 24.51 |

TABLE 8-continued

Significant Peaks in edisylate salt Form I of Compound 1
Significant Peaks
2-theta (deg)

| | |
|---|---|
| 14.54 | 25.04 |
| 15.27 | 25.47 |
| 15.56 | 25.68 |
| 15.90 | 26.30 |
| 16.55 | 27.08 |
| 17.33 | 27.49 |
| 17.80 | 27.99 |

TABLE 8-continued

Significant Peaks in edisylate salt Form I of Compound 1
Significant Peaks
2-theta (deg)

| | |
|---|---|
| 18.12 | 28.14 |
| 18.46 | 28.70 |
| 19.08 | 28.88 |
| 19.66 | 29.16 |

Figure 29:
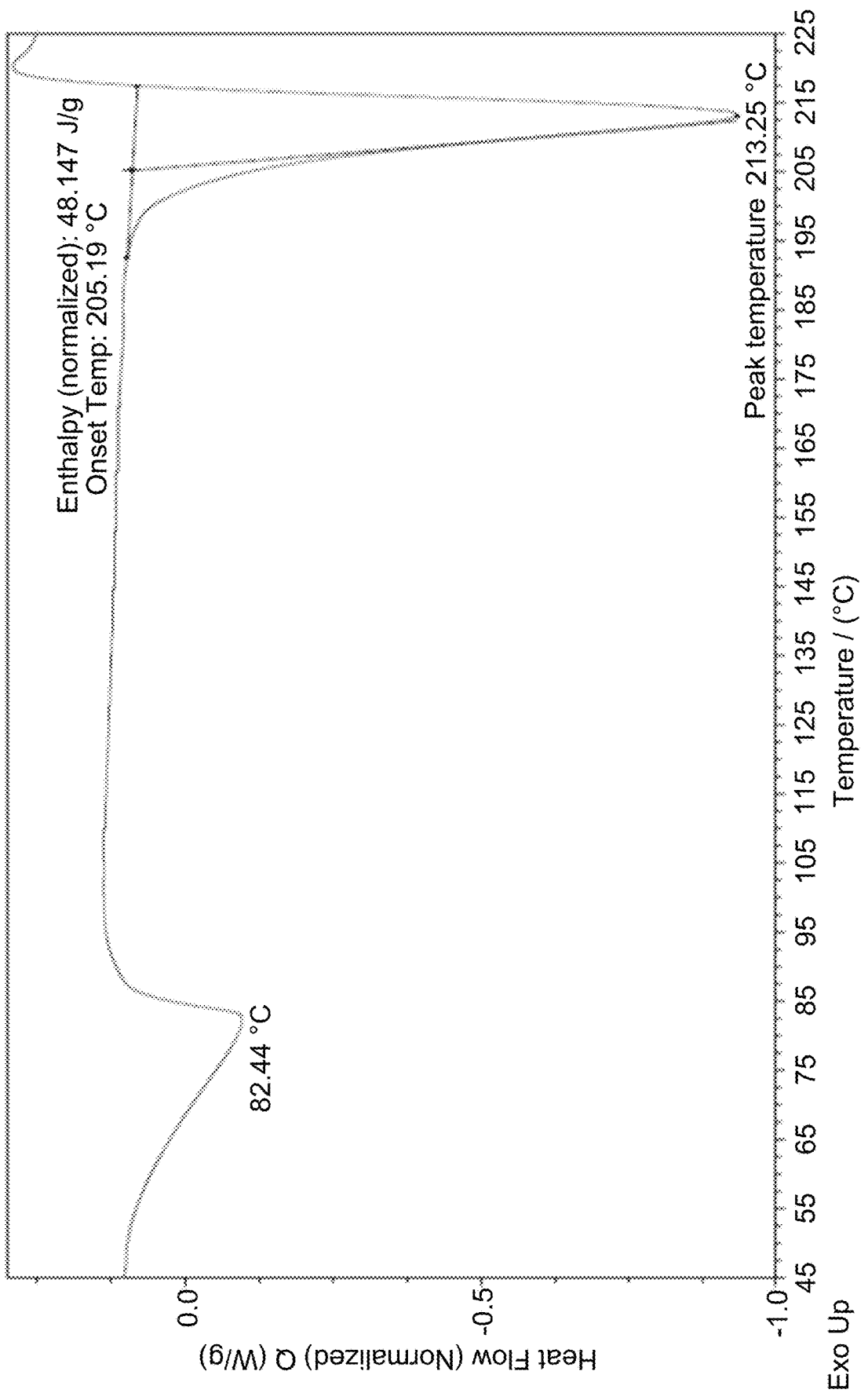
FIG. 29 shows the differential scanning calorimetry (DSC) thermogram of edisylate salt Form I of Compound 1.

Differential scanning calorimetry (DSC) was performed as described in Example 1. DSC analysis determined that the melting point (onset) is about 205.2° C. (DSC). The DSC plot also exhibits an endothermic peak at around 213.3° C. A plot of the DSC thermogram is shown in FIG. 29.

Example 8: Aqueous Suspension Formulations Using Salt Forms of Compound 1

Figure 30:
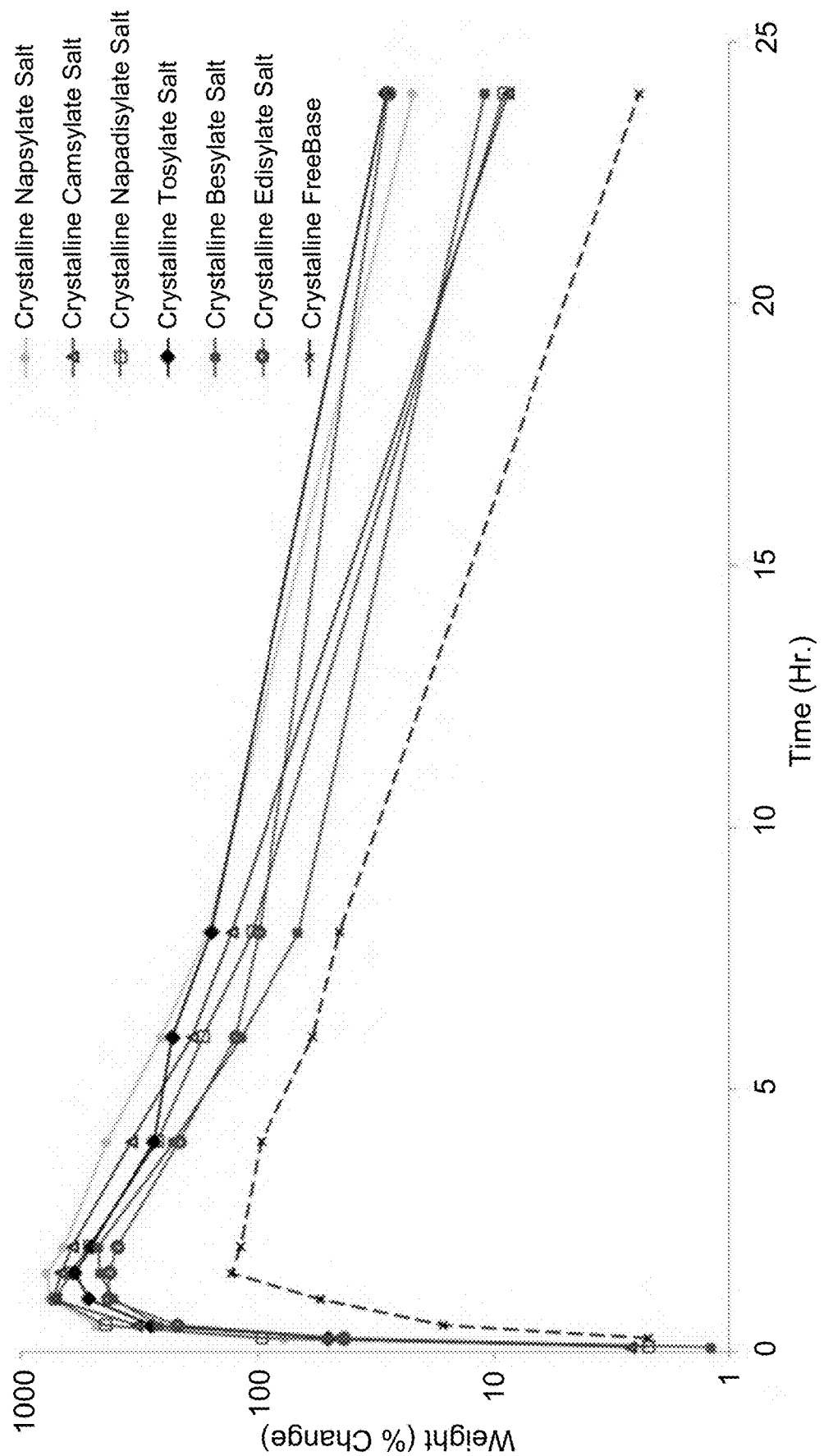
FIG. 30 displays plots of the plasma concentration over time of rats dosed with a liquid suspension formulation containing a crystalline form of Compound 1 (dashed line) and the same amount of a liquid suspension formulation containing various salt forms of Compound 1. Napsylate salt (filled circles); camsylate salt (open triangles); napadisylate salt (open squares); tosylate salt (filled diamonds), besylate salt (filled squares); edisylate salt (open circles). Further formulation details are provided in Example 8.

An in vivo rat PK study was conducted to compare the PK profile and bioavailability of the free base crystalline form of Compound 1 against various salt forms of Compound 1 in an aqueous liquid suspension formulation, which contained 0.5% w/v Hydroxypropyl Cellulose (Klucel GF grade) and 0.5% w/v Poloxamer F-68 (BASF Kolliphor P188). Each animal was orally administered 10 mg/kg of Compound 1 at 5 mL/kg dosing volume (a dosing concentration of 2 mg/mL). Table 9 summarizes the PK parameters measured. The PK profile of these formulations are shown in FIG. 30.

TABLE 9

Comparison of in vivo Rat PK Exposure

| API Lot | Crystalline Free Base | Besylate Salt (Form I) | Tosylate Salt (Form I) | Napsylate Salt (Form I) | Napadisylate Salt (Form I) | Camsylate Salt (Form I) | Edisylate Salt (Form I) |
|---|---|---|---|---|---|---|---|
| $C_{max}$ [ng/mL] | 129 | 493 | 591 | 778 | 718 | 738 | 435 |
| $AUC_{inf}$ [ng · hr/mL] | 996 | 2603 | 4149 | 5057 | 3478 | 3922 | 3197 |
| $AUC_{0-t}$ [ng · hr/mL] | 983 | 2508 | 4045 | 4876 | 3417 | 3870 | 2839 |

Example 9: Aqueous Suspension Formulations Using Salt Forms of Compound 1

Figure 31:
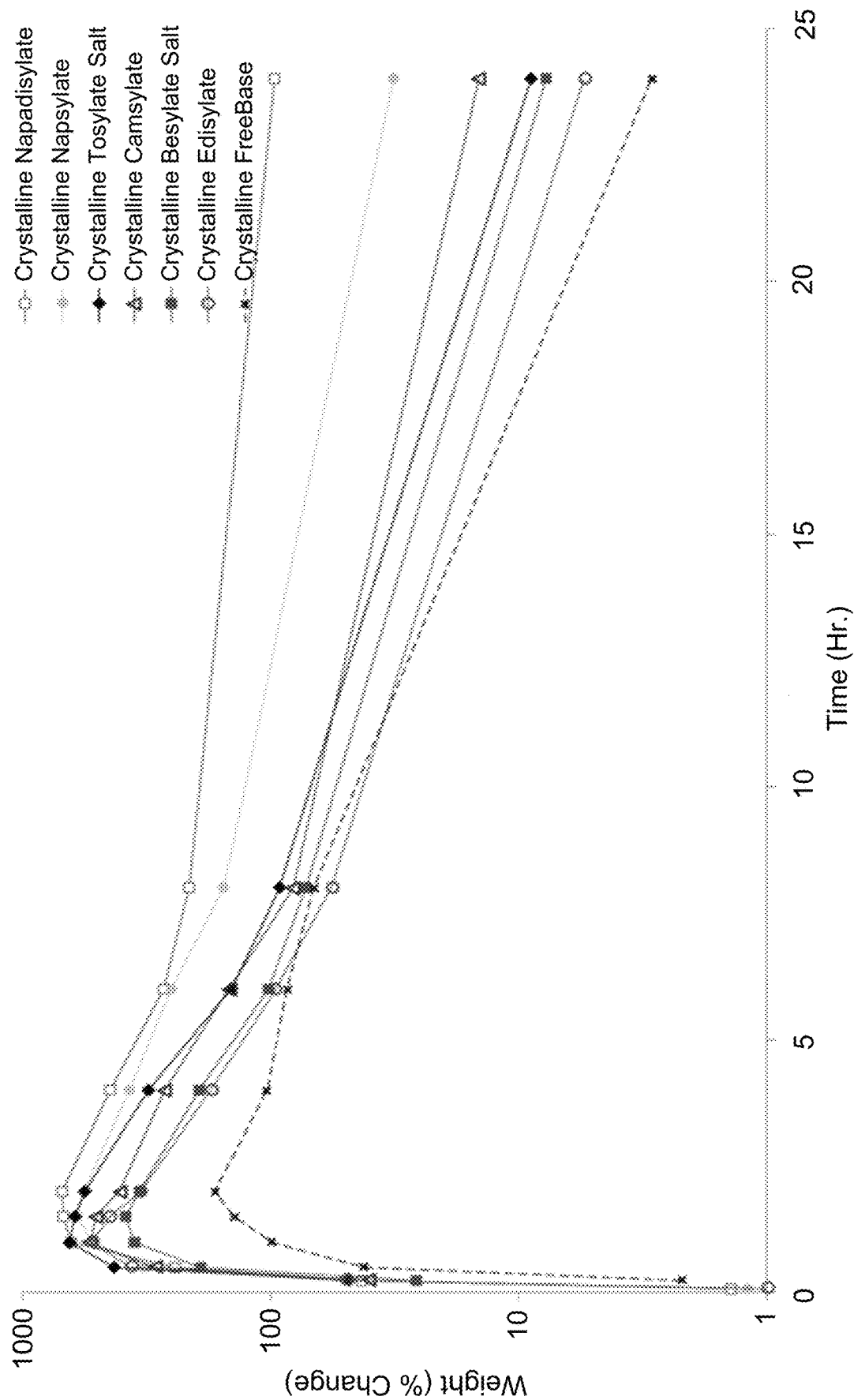
FIG. 31 displays plots of the plasma concentration over time of rats dosed with a liquid suspension formulation containing a crystalline form of Compound 1 (dashed line) and the same amount of a liquid suspension formulation containing various salt forms of Compound 1. Napsylate salt (filled circles); camsylate salt (open triangles); napadisylate salt (open squares); tosylate salt (filled diamonds), besylate salt (filled squares); edisylate salt (open circles). Further formulation details are provided in Example 9.

An in vivo rat PK study was conducted to compare the PK profile and bioavailability of the free base crystalline form of Compound 1 against various salt forms of Compound 1 in an aqueous liquid suspension formulation, which contained 1% HPMC. Each animal was orally administered 10 mg/kg of Compound 1 at 5 mL/kg dosing volume (a dosing concentration of 2 mg/mL). Table 10 summarizes the PK parameters measured. The PK profile of these formulations are shown in FIG. 31.

TABLE 10

Comparison of in vivo Rat PK Exposure

| API Lot | Crystalline Free Base | Crystalline Besylate Salt | Crystalline Tosylate Salt | Crystalline Napsylate | Crystalline Napadisylate | Crystalline Camsylate | Crystalline Edisylate |
|---|---|---|---|---|---|---|---|
| $C_{max}$ [ng/mL] | 168 | 390 | 649 | 601 | 753 | 553 | 525 |
| $AUC_{inf}$ [ng · hr/mL] | 1377 | 2222 | 3369 | 4589 | 7743 | 3005 | 2162 |
| $AUC_{0-t}$ [ng · hr/mL] | 1361 | 2168 | 3309 | 4277 | 5856 | 2877 | 2126 |

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A besylate salt Form I of Compound 1

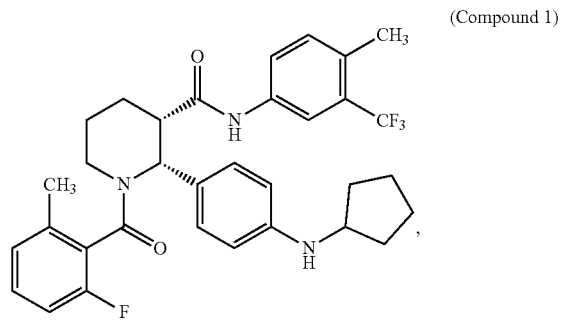 [SMILES: Cc1ccc(NC(=O)[C@H]2CCCN(C(=O)c3c(C)cccc3F)[C@H]2c2ccc(NC3CCCC3)cc2)cc1C(F)(F)F]

(Compound 1)

in a single crystalline form which is substantially free of other crystalline or amorphous forms,
characterized by an X-ray powder diffraction (XRPD) pattern comprising peaks at 10.9, 13.3, 16.2, 17.6 and 21.8 degrees 2θ (±0.2 degrees 2θ).

2. The besylate salt Form I, according to claim 1, further characterized by XRPD peaks at 6.6, 7.6, 14.5, 16.2, and 28.2 degrees 2θ (±0.2 degrees 2θ).

3. The besylate salt Form I, according to claim 1, characterized by an X-ray powder diffraction pattern substantially in accordance with FIG. 1.

4. The besylate salt Form I, according to claim 1, further characterized by a differential scanning calorimetry thermogram (DSC) comprising an endothermic peak at around 207.2° C.

5. The besylate salt Form I, according to claim 1, further characterized by a melting point onset of about 200.6° C. as determined by differential scanning calorimetry thermogram (DSC).

6. The besylate salt Form I, according to claim 1, wherein said DSC thermogram is substantially in accordance with FIG. 2.

7. The besylate salt Form I, according to claim 1, further characterized by a weight loss of about 0.14% upon heating to around 202.9° C., as measured by thermal gravimetric analysis (TGA).

8. The besylate salt Form I, according to claim 1, further characterized a thermal gravimetric analysis (TGA) thermogram substantially in accordance with FIG. 2.

9. The besylate salt Form I, according to claim 1, further characterized by a weight gain of about 0.5% after undergoing a dynamic vapor sorption cycle from about 0% relative humidity (RH) to about 75% RH at 25° C.

10. The besylate salt Form I, according to claim 1, further characterized by a weight gain of about 0.73% after undergoing a dynamic vapor sorption cycle from about 5% relative humidity (RH) to about 95% RH at 25° C.

11. The besylate salt Form I, according to claim 1, having a dynamic vapor sorption profile substantially as shown in FIG. 3.

12. The besylate salt Form I, according to claim 1, further characterized by a scanning electron microscopy (SEM) image having predominantly prismatic or anhedral particles.

13. The besylate salt Form I, according to claim 12, wherein particle sizes are about 1 μm to 73 μm as determined by scanning electron microscopy (SEM).

14. The besylate salt Form I, according to claim 1, further characterized by scanning electron microscopy (SEM) image substantially in accordance with FIG. 4.

15. The besylate salt Form I, according to claim 1, further characterized by particles ranging in size from about 2.5 to 83 μm as determined by polarized light microscope (PLM).

16. The besylate salt Form I, according to claim 1, further characterized by a polarized light microscope (PLM) profile substantially as shown in FIG. 5.

17. A besylate salt Form II of Compound 1

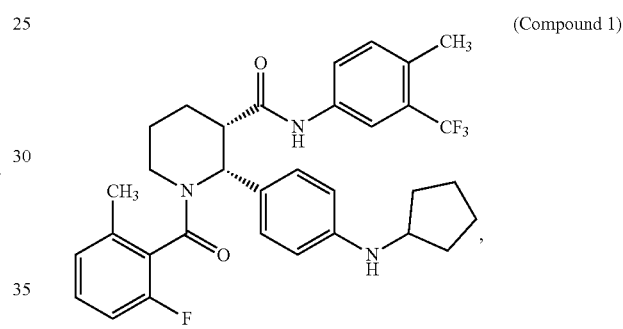

(Compound 1)

in a single crystalline form which is substantially free of other crystalline or amorphous forms,
characterized by an X-ray powder diffraction (XRPD) pattern comprising peaks at 3.6, 7.1, 12.3, 12.8, and 16.7 degrees 2θ (±0.2 degrees 2θ).

18. A tosylate salt Form I of Compound 1

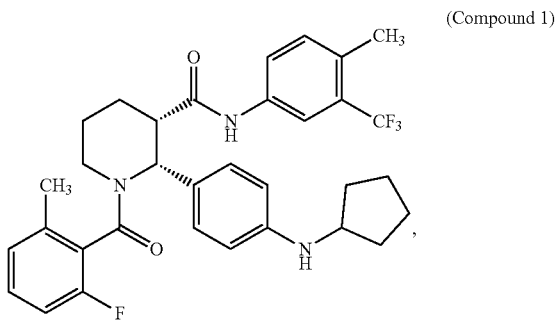 [SMILES: Cc1ccc(NC(=O)[C@H]2CCCN(C(=O)c3c(C)cccc3F)[C@H]2c2ccc(NC3CCCC3)cc2)cc1C(F)(F)F]

(Compound 1)

in a single crystalline form which is substantially free of other crystalline or amorphous forms,
characterized by an X-ray powder diffraction (XRPD) pattern comprising peaks at 7.6, 10.8, 13.1, 16.5, 19.7, 21.6 degrees 2θ (±0.2 degrees 2θ).

19. A napadislyate salt Form I of Compound 1

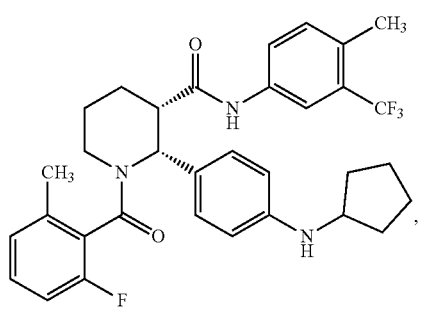
(Compound 1)

in a single crystalline form which is substantially free of other crystalline or amorphous forms,
characterized by an X-ray powder diffraction (XRPD) pattern comprising peaks at 6.5, 7.0, 12.4, 14.7, 15.2, and 18.0 degrees 2θ (±0.2 degrees 2θ).

20. A napsylate salt Form I of Compound 1

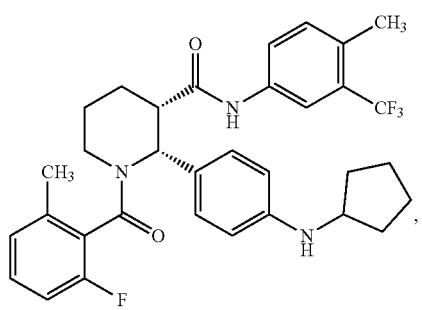
(Compound 1)

in a single crystalline form which is substantially free of other crystalline or amorphous forms,
characterized by an X-ray powder diffraction (XRPD) pattern comprising peaks at 6.5, 7.7, 10.4, 12.9, and 16.1 degrees 2θ (±0.2 degrees 2θ).

21. A camsylate salt Form of Compound 1

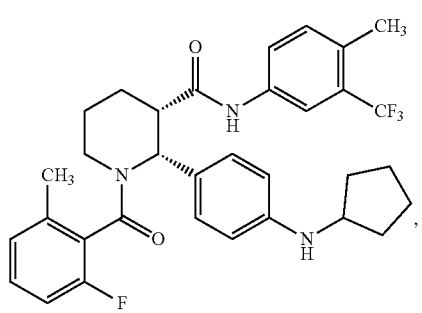
(Compound 1)

in a single crystalline form which is substantially free of other crystalline or amorphous forms,
characterized by an X-ray powder diffraction (XRPD) pattern comprising peaks at 6.3, 7.9, 10.8, 12.2, and 16.1 degrees 2θ (±0.2 degrees 2θ).

22. An edisylate salt Form I of Compound 1

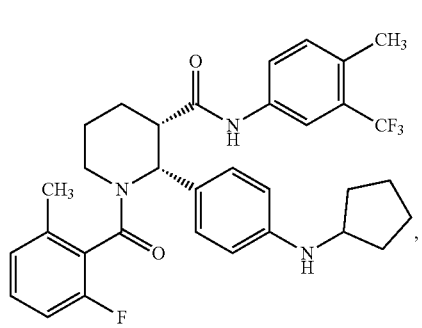
(Compound 1)

in a single crystalline form which is substantially free of other crystalline or amorphous forms,
characterized by an X-ray powder diffraction (XRPD) pattern comprising peaks at 3.4, 5.6, 12.9, 15.3, 18.1, and 20.8 degrees 2θ (±0.2 degrees 2θ).

23. A pharmaceutical composition comprising a salt form of Compound 1 according to claim 1 and at least one pharmaceutically acceptable excipient.

24. An aqueous suspension comprising a salt form of Compound 1 according to claim 1 and at least one excipient.

25. An injectable or infusible solution comprising Compound 1 and at least one wetting agent or solvent, wherein the injectable or infusible solution is prepared using a salt form of Compound 1 according to claim 1.

26. A method for treating an individual suffering from or susceptible to a disease or disorder involving pathologic activation of C5a receptors, comprising administering to the individual an effective amount of a salt form of Compound 1 according to claim 1, wherein the disease or disorder involving pathologic activation of C5a receptors is an autoimmune disorder, inflammatory disorder, cardiovascular and cerebrovascular, diseases of vasculitis, HIV infection and AIDS, neurodegenerative disorder, and cancer.

27. The besylate salt Form II, according to claim 17, characterized by an X-ray powder diffraction pattern substantially in accordance with FIG. 6.

28. The tosylate salt Form I according to claim 18, characterized by an X-ray powder diffraction pattern substantially in accordance with FIG. 8.

29. The napadisylate salt Form I according to claim 19, characterized by an X-ray powder diffraction pattern substantially in accordance with FIG. 13.

30. The napsylate salt Form I according to claim 20, characterized by an X-ray powder diffraction pattern substantially in accordance with FIG. 18.

31. The camsylate salt Form I according to claim 21, characterized by an X-ray powder diffraction pattern substantially in accordance with FIG. 23.

32. The edisylate salt Form I according to claim 22, characterized by an X-ray powder diffraction pattern substantially in accordance with FIG. 28.

* * * * *